(12) United States Patent
Kanouni

(10) Patent No.: US 11,453,676 B2
(45) Date of Patent: Sep. 27, 2022

(54) INHIBITORS OF PROTEIN ARGININE DEIMINASES

(71) Applicant: Forward Therapeutics, Inc., Rancho Santa Fe, CA (US)

(72) Inventor: Toufike Kanouni, Rancho Santa Fe, CA (US)

(73) Assignee: FORWARD THERAPEUTICS, INC., Rancho Santa Fe, CA (US)

( * ) Notice: Subject to any disclaimer, the term of this patent is extended or adjusted under 35 U.S.C. 154(b) by 0 days.

(21) Appl. No.: 16/962,710

(22) PCT Filed: Feb. 1, 2019

(86) PCT No.: PCT/US2019/016412
§ 371 (c)(1),
(2) Date: Jul. 16, 2020

(87) PCT Pub. No.: WO2019/152883
PCT Pub. Date: Aug. 8, 2019

(65) Prior Publication Data
US 2021/0053975 A1    Feb. 25, 2021

Related U.S. Application Data

(60) Provisional application No. 62/625,899, filed on Feb. 2, 2018.

(51) Int. Cl.
| | | |
|---|---|---|
| *C07D 487/10* | (2006.01) | |
| *C07D 209/42* | (2006.01) | |
| *C07D 401/06* | (2006.01) | |
| *C07D 401/12* | (2006.01) | |
| *C07D 403/06* | (2006.01) | |
| *C07D 403/12* | (2006.01) | |
| *C07D 405/12* | (2006.01) | |
| *C07D 487/04* | (2006.01) | |

(52) U.S. Cl.
CPC ......... *C07D 487/10* (2013.01); *C07D 209/42* (2013.01); *C07D 401/06* (2013.01); *C07D 401/12* (2013.01); *C07D 403/06* (2013.01); *C07D 403/12* (2013.01); *C07D 405/12* (2013.01); *C07D 487/04* (2013.01)

(58) Field of Classification Search
CPC .. C07D 487/04; C07D 405/12; C07D 487/10; C07D 209/42; C07D 403/06; C07D 401/12; C07D 403/12
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 7,544,698 B2 * | 6/2009 | Edwards | ................. A61P 15/00 548/468 |
| 2004/0132715 A1 | 7/2004 | Dunford et al. | |
| 2007/0238771 A1 | 10/2007 | Edwards et al. | |
| 2016/0000777 A1 | 1/2016 | Beck et al. | |

FOREIGN PATENT DOCUMENTS

| | | |
|---|---|---|
| EP | 1445250 A1 | 8/2004 |
| EP | 2046789 A2 | 4/2009 |
| JP | H01132579 A | 5/1989 |
| WO | WO-2004022061 A1 | 3/2004 |
| WO | WO-2006056848 A1 | 6/2006 |
| WO | WO-2009158375 A1 | 12/2009 |
| WO | WO-2014188193 A1 | 11/2014 |
| WO | WO-2015048570 A2 | 4/2015 |
| WO | WO-2016185279 A1 | 11/2016 |
| WO | WO-2018119395 A1 | 6/2018 |
| WO | WO-2019152883 A1 | 8/2019 |

OTHER PUBLICATIONS

Berge et al. Pharmaceutical Salts. Journal of Pharmaceutical Sciences 66(1): 1-19 (Jan. 1977).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
PCT/US2019/016412 International Search Report and Written Opinion dated May 31, 2019.
PCT/US2019/016412 Invitation to Pay Additional Fees dated Apr. 3, 2019.
Pubchem CID 39732693 (Pubchem-693).
Aurora Fine Chemicals LLC. RN 10360385-63-2. Database Registry [Online] Chemical Abstracts Service, Columbus, Ohio, US; Mar. 7, 2012 (Mar. 7, 2012), & Aurora Bildings Block 7, Apr. 19, 2021 (2021-04-19) DOI: https://www.aurorfinechemicals.com.
Christopher et al. A Bioinformatics Search for Selective Histamine H4 Receptor Antagonists Through Structure- Based Virtual Screening Strategies. Chem Biol Drug Des 79(5):749-759 (2012).
Engelhardt et al. Detailed structure-activity relationship of indolecarboxamides as H4receptor ligands. Eur J Med Chem 54:660-668 (2012).
Mochizuki et al. Design, synthesis, and biological activity of piperidine diamine derivatives as factor Xa inhibitor. Bioorg Med Chem Lett 18(2):782-787 (2008).
Pontiki et al. QSAR models on H 4 receptor antagonists associated with inflammation and anaphylaxis. J Biomol Struct Dyn 35(5):968-1005 (2017).
Terzioglu et al. Synthesis and structure-activity relationships of indole and benzimidazole piperazines as histamine H4 receptor antagonists. Bioorg Med Chem Lett 14(21):5251-5256 (2004).

\* cited by examiner

*Primary Examiner* — Rebecca L Anderson
(74) *Attorney, Agent, or Firm* — Wilson Sonsini Goodrich & Rosati

(57) ABSTRACT

Provided herein are inhibitors of protein arginine deiminases (PADs), pharmaceutical compositions comprising said the compounds, and methods for using the compounds for the treatment of diseases.

17 Claims, No Drawings

INHIBITORS OF PROTEIN ARGININE DEIMINASES

CROSS-REFERENCE TO RELATED APPLICATION

This application is the U.S. National Stage application of International Application No. PCT/US2019/016412, filed on Feb. 1, 2019, and claims the benefit of U.S. Provisional Patent Application No. 62/625,899, filed on Feb. 2, 2018, which is hereby incorporated by reference in its entirety.

BACKGROUND

Peptidylarginine deiminases (PADs) are a family of enzymes that mediate posttranslational modifications of protein arginine residues by deimination or demethylimination to produce citrulline. The activity of PADs is dependent on calcium and reductive reagents carrying a free sulfhydryl group. The deregulation of PADs is involved in the etiology of multiple human diseases, including cancers and autoimmune disorders.

BRIEF SUMMARY OF THE INVENTION

Provided herein are inhibitors of protein arginine deiminases (PADs), pharmaceutical compositions comprising said compounds, and methods for using said compounds for the treatment of diseases.

One embodiment provides a compound, or pharmaceutically acceptable salt or solvate thereof, having the structure of Formula (I):

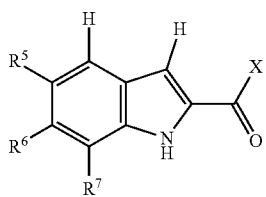

(I)

wherein, $R^5$ is selected from halogen;

$R^6$ is selected from hydrogen, or halogen;

$R^7$ is selected from hydrogen, or halogen;

X is selected from:

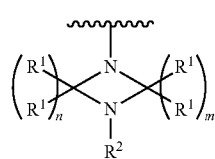

(a)

wherein n is 2, 3, or 4; m is 2, 3, or 4; each $R^1$ is independently selected from hydrogen or optionally substituted alkyl; and $R^2$ is hydrogen or optionally substituted alkyl;

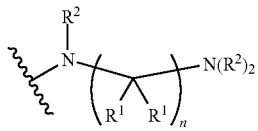

(b)

wherein n is 2, 3, or 4; each $R^1$ is independently selected from hydrogen, optionally substituted alkyl, optionally substituted cycloalkyl, or optionally substituted cycloalkylalkyl; and each $R^2$ is independently hydrogen or optionally substituted alkyl;

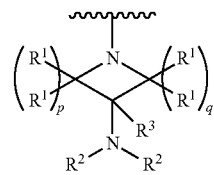

(c)

wherein p is 1, 2, 3, or 4; q is 1, 2, 3, or 4; each $R^1$ is independently selected from hydrogen, halogen, —OH, —NH₂, optionally substituted alkyl, or optionally substituted alkoxy; each $R^2$ is hydrogen or optionally substituted alkyl; and $R^3$ is hydrogen or optionally substituted alkyl;

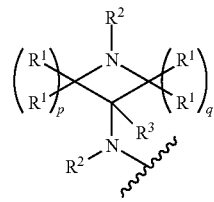

(d)

wherein p is 0, 1, 2, 3, or 4; q is 1, 2, 3, or 4; each $R^1$ is independently selected from hydrogen, halogen, —OH, —NH₂, optionally substituted alkyl, or optionally substituted alkoxy; each $R^2$ is hydrogen or optionally substituted alkyl; and $R^3$ is hydrogen or optionally substituted alkyl;

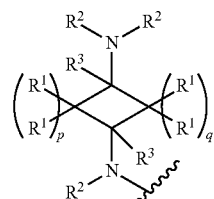

(d)

wherein p is 0, 1, 2, 3, or 4; q is 1, 2, 3, or 4; each $R^1$ is independently selected from hydrogen, halogen, —OH, —NH₂, optionally substituted alkyl, or optionally substituted alkoxy; each $R^2$ is hydrogen or optionally substituted alkyl, and $R^3$ is hydrogen or optionally substituted alkyl.

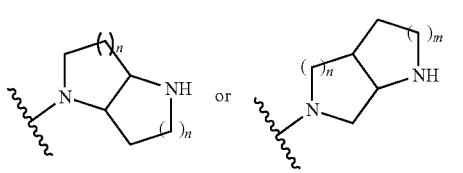

wherein m is 0, 1, 2, 3, or 4; and n is 0, 1, 2, 3, or 4;

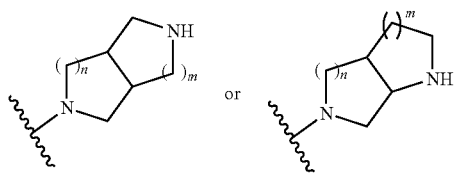

wherein m is 0, 1, 2, 3, or 4; and n is 0, 1, 2, 3, or 4;

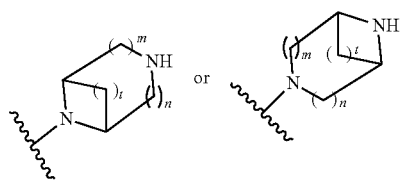

wherein m is 1, 2, or 3; n is 0, 1, 2, or 3; and t is 0, 1, 2, or 3;

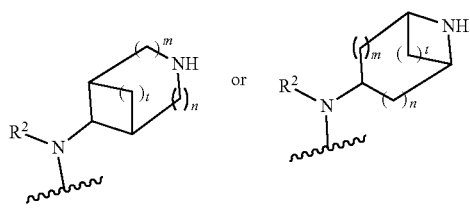

wherein $R^2$ is hydrogen; m is 1, 2, or 3; n is 0, 1, 2, or 3; and t is 0, 1, 2 or 3;

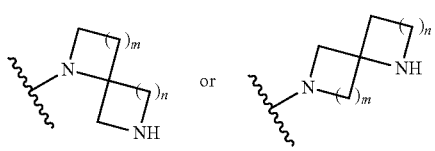

wherein m is 0, 1, 2, 3, or 4; and n is 0, 1, 2, 3, or 4; or

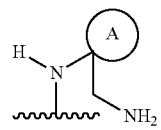

wherein ring A is an optionally substituted 4-, 5-, or 6-membered heterocyclic ring with an oxygen atom or a nitrogen atom.

One embodiment provides a pharmaceutical composition comprising a compound of Formula (I), or pharmaceutically acceptable salt or solvate thereof, and at least one pharmaceutically acceptable excipient.

One embodiment provides a method of treating an autoimmune disease or disorder in a patient in need thereof comprising administering to the patient a compound of Formula (I), or pharmaceutically acceptable salt or solvate thereof. Another embodiment provides the method wherein the autoimmune disease or disorder is rheumatoid arthritis.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.

"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$), —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$), —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —$R^b$—S(O)N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

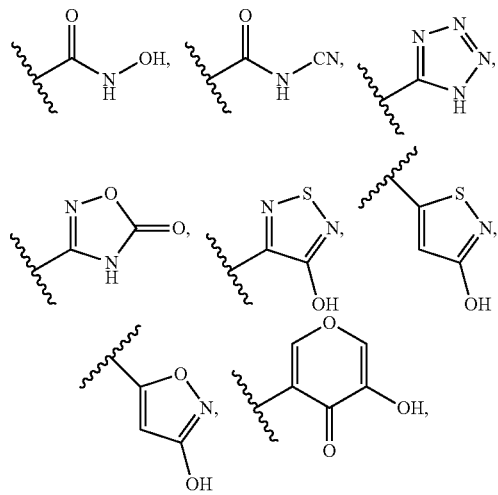

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—OR, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)R^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

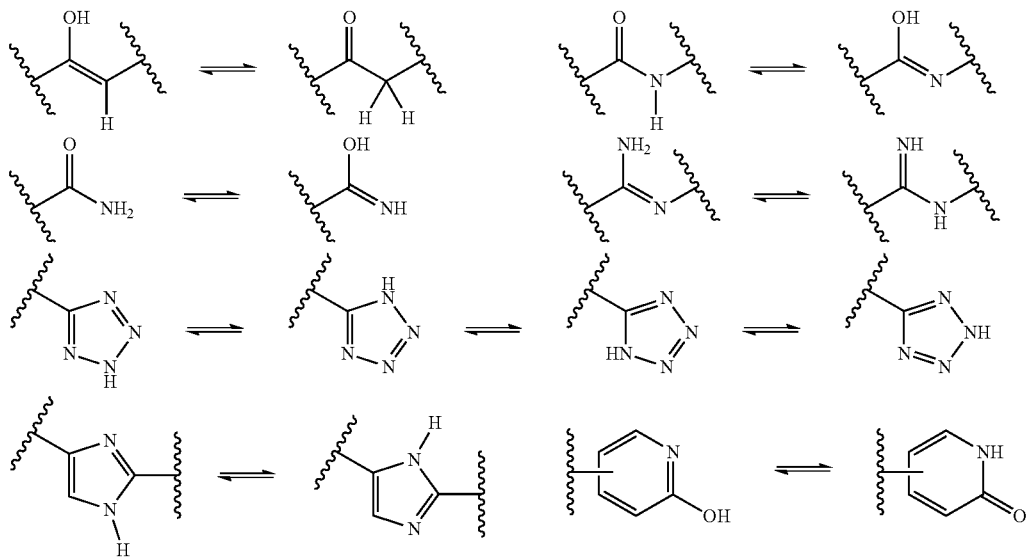

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium ($^{3}H$), iodine-125 ($^{125}I$) or carbon-14 (14C). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

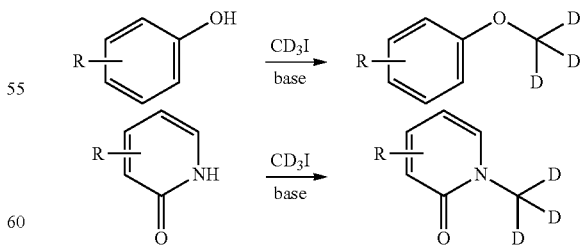

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

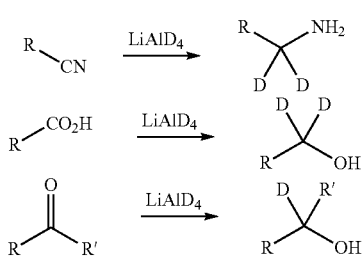

Deuterium gas and palladium catalyst are employed to reduce unsaturated carbon-carbon linkages and to perform a reductive substitution of aryl carbon-halogen bonds as illustrated, by way of example only, in the reaction schemes below.

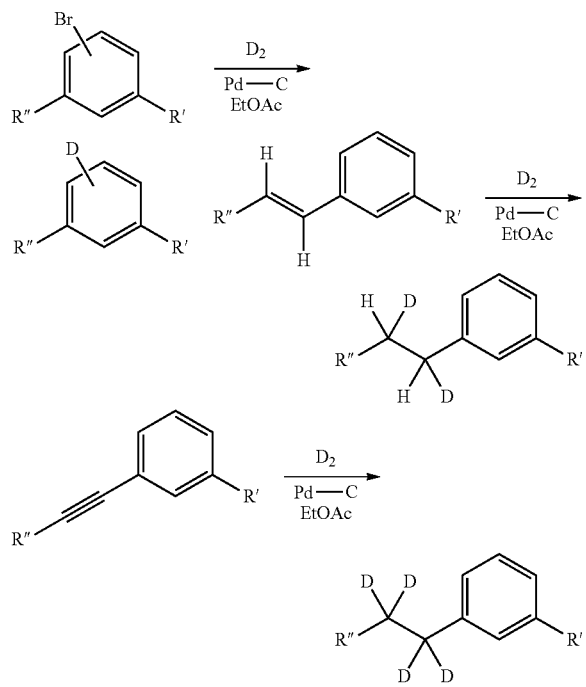

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the inhibitor of protein arginine deiminases (PADs) compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to composition of matter that is the solvent addition form. In some embodiments, solvates contain either stoichiometric or nonstoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Inhibitors of Protein Arginine Deiminases (PADs)

Peptidylarginine deiminases (PADs) are a family of enzymes that mediate posttranslational modifications of protein arginine residues by deimination or demethylimination to produce citrulline. In vitro, the activity of PADs is dependent on calcium and reductive reagents carrying a free sulfhydryl group. The deregulation of PADs is involved in the etiology of multiple human diseases, including cancers and autoimmune disorders. PADs are involved in normal functions in the immune and reproduction systems as well as in the skin. In each of the mammalian vertebrate genomes, five highly conserved PADs exist, including PAD1, 2, 3, 4 and 6. Human PAD4 can bind five calcium ions. Several flexible parts of PAD4 form stable secondary structures after the binding of calcium and substrate, indicating that calcium stabilizes the conformation of PAD4 and may facilitate the formation of the active site cleft. The calcium binding sites in PAD4 are conserved in PAD1, -2, and-3 except for PAD6. Thus, calcium is an important regulator of the active PAD enzymes.

PAD1 is mainly expressed in epidermis and uterus. PAD1 deiminates keratin K1 and is involved in the cornification of epidermal tissues.

PAD2 is widely expressed in multiple tissues, including secretory glands, brain, uterus, spleen, pancreas, skeletal muscle. The expression of PAD2 can be regulated at both mRNA splicing and protein translation levels. Myelin basic protein of the central nervous system and vimentin in skeletal muscle and macrophages are long known substrates of PAD2. Recently, R and γ-actins were identified as PAD2 substrates in human neutrophils. PAD2 is mainly a cytoplasmic protein, but a fraction of PAD2 may become nuclear in canine and human mammary epithelial cells. Nuclear PAD2 may citrullinate histones H3 and H4, suggesting a role of this protein in gene regulation.

PAD3 is localized to epidermis and hair follicles. PAD3 is colocalized with trichohyalin, a structural protein in the inner root sheath and medulla of hair follicles. In addition, PAD3 colocalizes with profilaggrin and filaggrin in the epidermis. PAD3 targets filaggrin, which interacts with keratin intermediate filament to regulate epidermal homeostasis in the granular layer and lower stratum corneum of human epidermis. Deimination of filaggrin and trichohyalin in vitro by recombinant PAD3 further supports that PAD3 is involved in regulating epidermis functions.

PAD4 (also called PADV and PADI4) is detected mainly in white blood cells including granulocytes and monocytes under normal physiological conditions. However, in a wide range of tumors of various tissue origins, the overexpression of PAD4 was detected, suggesting that PAD4 plays a role in tumorigenesis. PAD4 is localized primarily in the nucleus and contains a nuclear localization signal sequence at its N-terminus. PAD4 citrullinates a range of nuclear proteins, such as histones H2A, H3 and H4, ING4, p300/CBP, nucleophosmin and nuclear lamin C, thereby playing an important role in nuclear functions.

PAD6 was originally identified from mouse eggs and embryos and was named ePAD (egg PAD). PAD6 regulates oocyte cytoskeletal sheet formation and female fertility. It is found that PAD6 localizes to the cytoplasmic lattices and regulates the function of microtubules during early embryo development. In human tissues, PAD6 is mainly restricted to ovary, testis and peripheral blood leucocytes. Interestingly, unlike the other PADs, PAD6 have lost some of the conserved Ca2+ binding residues and the active center cysteine residue is also different from other PADs, suggesting that PAD6 is likely not an active deiminase.

Among PADs, PAD2 and PAD4 are of particular importance in gene regulation and cellular function. Thus, the ability of PAD2 to citrullinate histone H4 Arg3 in vitro raises a role of PAD2-mediated histone citrullination in transcriptional regulation. The expression of PAD2 is regulated by estrogen in vertebrate uterus and pituitary gland. It was recently shown that PAD2 responses to cellular signals are able to regulate transcription via histone citrullination. Only during the diestrus phase of the reproduction cycle, PAD2 in mammary gland epithelial cells was found to citrullinate the histone H3 N-terminus. Moreover, PAD2 is detected in human breast luminal epithelial cells, and associates with target gene promoters in the ERa positive breast cancer MCF-7 cells to regulate histone H3 Arg26 citrullination and transcription. Estradiol stimulates the recruitment of PAD2 to the estrogen-response element of estrogen receptor alpha (ERa) target gene promoters. Since PAD2 does not have a nuclear localization signal, its association with ERa may facilitate its translocation from the cytosolic to the nuclear compartment. As such, PAD2 likely mediates chromatin decondensation and activation of target gene transcription during cellular response to estrogen stimulation. These studies indicate that PAD2 functions as an epigenetic regulator of gene activity.

PAD4 antagonizes CARM1 (also called PRMT4) and PRMT1 mediated histone H3 and H4 Arg methylation through a reaction dubbed as demethylimination in reflecting the removal of the methyl-imine group from monomethyl-arginine residues. CARM1 and PRMT1 function as transcription coactivators by catalyzing histone Arg monomethylation and asymmetrical dimethylation. By antagonizing Arg methylation, PAD4 functions as a transcription corepressor. In the case of ER (estrogen receptor) target genes in the breast cancer MCF-7 cells, it was found that PAD4 regulates histone Arg methylation via its citrullination activity on the gene promoters. In addition to the ER target genes, it was found that PAD4 interacts with the tumor suppressor and transcription factor p53 and functions as a corepressor to regulate the expression of multiple p53 target genes. Before DNA damage, a high level of histone citrullination and PAD4 is detected on the promoter of p53 target genes, such as p21/CIP1/WAF1, GADD45 and PUMA. After DNA damage, PAD4 association and histone citrullination decreases on these gene promoters with a concomitant increase in histone Arg methylation, suggesting that citrullination and arginine methylation counteract each other's function to regulate gene expression.

Based on the role of PADs in posttranslational modification of positively charged protein-bound arginine and methylarginine residues, which plays an important part in the gene regulation and cellular function, the compounds which alter PADs activity are considered to be useful in treating or preventing various disorders, including rheumatoid arthritis, vasculitis, systemic lupus erythematosus, ulcerative colitis, cancer, cystic fibrosis, asthma, cutaneous lupus erythematosus, and psoriasis. In some embodiments, described herein is a small molecule inhibitor of protein arginine deiminases (PADs). In other embodiments, a small molecule inhibitor of protein arginine deiminases (PADs) is used to treat or prevent a disease or condition in a subject in need thereof.

Rheumatoid Arthritis

Rheumatoid arthritis (RA) is a chronic autoimmune disease featured with inflammatory synovium and infiltration of activated macrophages. The anti-citrullinated protein antibodies are the most specific autoantibodies present in the RA sera. Most of these autoantibodies can be detected in the early stage of the disease, which makes them useful diagnostic markers of RA. Those citrullinated proteins, including fibrin, fibrinogen and vimentin, were produced in synovial fluid of the inflammatory joints. The presence of citrulline residues in these proteins sends the immune cells a false alarm and initiates immune responses to generate anti-citrulline antibodies against these proteins. Many PAD2 and PAD4 expressing leucocytes infiltrate into the inflammatory synovial tissues in RA patients and release large amount of PAD2 and PAD4 in the synovial fluid, which in turn produce high levels of citrullinated proteins. Since the calcium concentration in the extracellular space is at the millimolar levels, PAD4 released from the dying neutrophils during the neutrophil extracellular traps (NETs; NETosis) formation process can be super-activated to citrullinate joint proteins. In addition to these pathology links, the involvement of PAD4 in rheumatoid arthritis is also supported by human genetic studies.

In some embodiments, a heterocyclic PAD4 inhibitory compound as described herein is used to treat or prevent rheumatoid arthritis in a subject in need thereof. In some embodiments, a pharmaceutical composition comprising a heterocyclic PAD4 inhibitory compound as described herein is used to treat or prevent rheumatoid arthritis in a subject in need thereof. In some embodiments is a method of treating rheumatoid arthritis comprising administering to a subject in need thereof a therapeutically effective amount of a heterocyclic PAD4 inhibitory compound as described herein. In some embodiments is a method of treating rheumatoid arthritis comprising administering to a subject in need thereof a therapeutically effective amount of a pharmaceutical composition comprising a heterocyclic PAD4 inhibitory compound as described herein. In some embodiments is a method of treating rheumatoid arthritis comprising administering to a subject having been previously diagnosed with rheumatoid arthritis a therapeutically effective amount of a heterocyclic PAD4 inhibitory compound as described herein.

Heterocyclic PAD4 Inhibitory Compounds

In one aspect, provided herein is a heterocyclic PAD4 inhibitory compound.

In another aspect is provided a compound, or pharmaceutically acceptable salt or solvate thereof, having the structure of Formula (I):

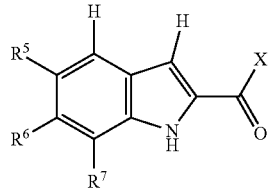

(I)

wherein,
$R^5$ is selected from halogen;
$R^6$ is selected from hydrogen, or halogen;
$R^7$ is selected from hydrogen, or halogen;
X is selected from:

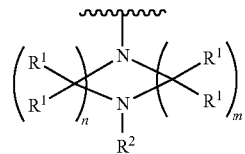

(a)

wherein n is 2, 3, or 4; m is 2, 3, or 4; each $R^1$ is independently selected from hydrogen or optionally substituted alkyl; and $R^2$ is hydrogen or optionally substituted alkyl;

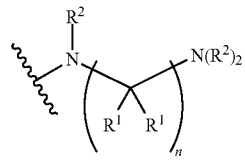

(b)

wherein n is 2, 3, or 4; each $R^1$ is independently selected from hydrogen, optionally substituted alkyl, optionally substituted cycloalkyl, or optionally substituted cycloalkylalkyl; and each $R^2$ is independently hydrogen or optionally substituted alkyl;

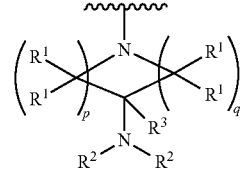

(c)

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl;

(d)
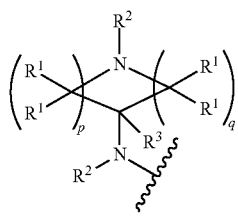

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl;

(e)
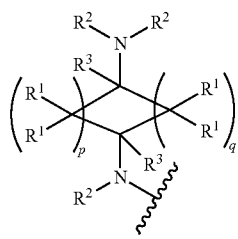

wherein p is 0, 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl;

(f)
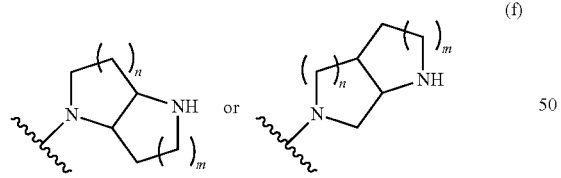

wherein m is 0, 1, 2, 3, or 4; and n is 0, 1, 2, 3, or 4;

(g)
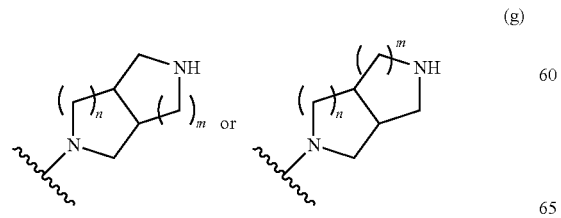

wherein m is 0, 1, 2, 3, or 4; and n is 0, 1, 2, 3, or 4;

(h)
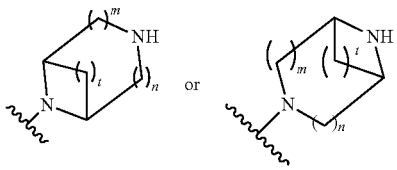

wherein m is 1, 2, or 3; n is 0, 1, 2, or 3; and t is 0, 1, 2, or 3;

(i)
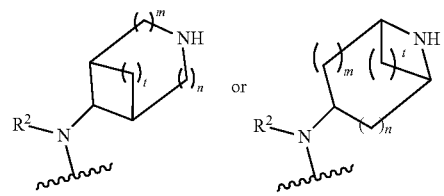

wherein $R^2$ is hydrogen; m is 1, 2, or 3; n is 0, 1, 2, or 3; and t is 0, 1, 2, or 3;

(j)
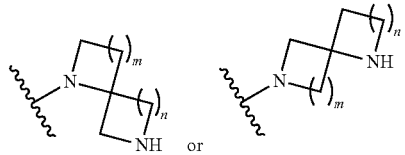

wherein m is 0, 1, 2, 3, or 4; and n is 0, 1, 2, 3, or 4; or (k)
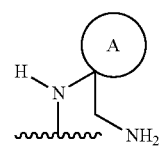

wherein ring A is an optionally substituted 4-, 5-, or 6-membered heterocyclic ring with an oxygen atom or a nitrogen atom.

Another embodiment provides the compound of Formula (I), or pharmaceutically acceptable salt or solvate thereof, wherein X is:

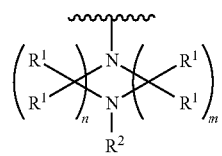

wherein n is 2, 3, or 4; m is 2, 3, or 4; each $R^1$ is independently selected from hydrogen or optionally substituted alkyl; and R² is hydrogen or optionally substituted alkyl. Another embodiment provides the compound, or pharmaceutically acceptable salt or solvate thereof, wherein R² is hydrogen. Another embodiment provides the compound, or pharmaceutically acceptable salt or solvate thereof, wherein R¹ is hydrogen. Another embodiment provides the compound, or pharmaceutically acceptable salt or solvate thereof, wherein n is 2 or 3; and m is 2 or 3.

Another embodiment provides the compound of Formula (I), or pharmaceutically acceptable salt or solvate thereof, wherein X is:

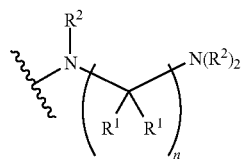

wherein n is 2, 3, or 4; each R¹ is independently selected from hydrogen, optionally substituted alkyl, optionally substituted cycloalkyl, or optionally substituted cycloalkylalkyl; and each R² is independently hydrogen or optionally substituted alkyl. Another embodiment provides the compound, or pharmaceutically acceptable salt or solvate thereof, wherein each R¹ is independently selected from hydrogen, optionally substituted alkyl. Another embodiment provides the compound, or pharmaceutically acceptable salt or solvate thereof, wherein each R² is hydrogen. Another embodiment provides the compound, or pharmaceutically acceptable salt or solvate thereof, wherein n is 2 or 3.

Another embodiment provides the compound of Formula (I), or pharmaceutically acceptable salt or solvate thereof, wherein X is:

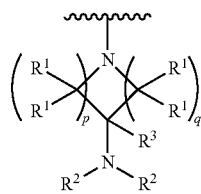

wherein p is 1, 2, 3, or 4; q is 1, 2, 3, or 4; each R¹ is independently selected from hydrogen, halogen, —OH, —NH₂, optionally substituted alkyl, or optionally substituted alkoxy; each R² is hydrogen or optionally substituted alkyl; and R³ is hydrogen or optionally substituted alkyl. Another embodiment provides the compound, or pharmaceutically acceptable salt or solvate thereof, wherein R² is hydrogen, and R³ is hydrogen. Another embodiment provides the compound, or pharmaceutically acceptable salt or solvate thereof, wherein R¹ is hydrogen. Another embodiment provides the compound, or pharmaceutically acceptable salt or solvate thereof, wherein p is 1, and q is 1. Another embodiment provides the compound, or pharmaceutically acceptable salt or solvate thereof, wherein p is 2, and q is 1. Another embodiment provides the compound, or pharmaceutically acceptable salt or solvate thereof, wherein p is 1, and q is 2. Another embodiment provides the compound, or pharmaceutically acceptable salt or solvate thereof, wherein p is 1, and q is 3. Another embodiment provides the compound, or pharmaceutically acceptable salt or solvate thereof, wherein p is 2, and q is 2.

Another embodiment provides the compound of Formula (I), or pharmaceutically acceptable salt or solvate thereof, wherein X is:

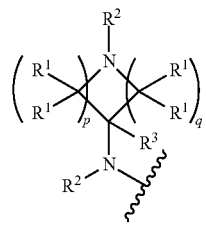

wherein p is 1, 2, 3, or 4; q is 1, 2, 3, or 4; each R¹ is independently selected from hydrogen, halogen, —OH, —NH₂, optionally substituted alkyl, or optionally substituted alkoxy; each R² is hydrogen or optionally substituted alkyl; and R³ is hydrogen or optionally substituted alkyl. Another embodiment provides the compound, or pharmaceutically acceptable salt or solvate thereof, wherein R² is hydrogen, and R³ is hydrogen. Another embodiment provides the compound, or pharmaceutically acceptable salt or solvate thereof, wherein R¹ is hydrogen. Another embodiment provides the compound, or pharmaceutically acceptable salt or solvate thereof, wherein p is 1, and q is 1. Another embodiment provides the compound, or pharmaceutically acceptable salt or solvate thereof, wherein p is 2, and q is 1. Another embodiment provides the compound, or pharmaceutically acceptable salt or solvate thereof, wherein p is 1, and q is 2. Another embodiment provides the compound, or pharmaceutically acceptable salt or solvate thereof, wherein p is 1, and q is 3. Another embodiment provides the compound, or pharmaceutically acceptable salt or solvate thereof, wherein p is 2, and q is 2.

Another embodiment provides the compound of Formula (I), or pharmaceutically acceptable salt or solvate thereof, wherein X is:

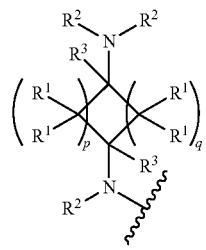

wherein p is 0, 1, 2, 3, or 4; q is 1, 2, 3, or 4; each R¹ is independently selected from hydrogen, halogen, —OH, —NH₂, optionally substituted alkyl, or optionally substituted alkoxy; each R² is hydrogen or optionally substituted alkyl; and R³ is hydrogen or optionally substituted alkyl. Another embodiment provides the compound, or pharmaceutically acceptable salt or solvate thereof, wherein R² is hydrogen, and R³ is hydrogen. Another embodiment provides the compound, or pharmaceutically acceptable salt or solvate thereof, wherein R¹ is hydrogen. Another embodiment provides the compound, or pharmaceutically acceptable salt or solvate thereof, wherein p is 1, and q is 1. Another embodiment provides the compound, or pharmaceutically acceptable salt or solvate thereof, wherein p is 2, and q is 1. Another embodiment provides the compound, or pharmapharmaceutically acceptable salt or solvate thereof, wherein p is 1, and q is 2. Another embodiment provides the compound, or pharmaceutically acceptable salt or solvate thereof, wherein p is 1, and q is 3. Another embodiment provides the compound, or pharmaceutically acceptable salt or solvate thereof, wherein p is 2, and q is 2.

Another embodiment provides the compound of Formula (I), or pharmaceutically acceptable salt or solvate thereof, wherein X is:

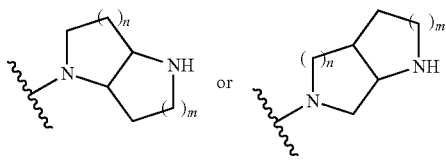

wherein m is 0, 1, 2, 3, or 4; and n is 0, 1, 2, 3, or 4. Another embodiment provides the compound, or pharmaceutically acceptable salt or solvate thereof, wherein X is:

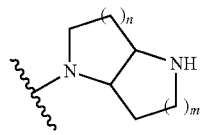

wherein m is 0, 1, 2, 3, or 4; and n is 0, 1, 2, 3, or 4. Another embodiment provides the compound, or pharmaceutically acceptable salt or solvate thereof, wherein X is:

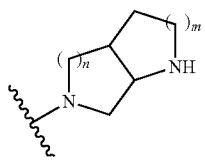

wherein m is 0, 1, 2, 3, or 4; and n is 0, 1, 2, 3, or 4. Another embodiment provides the compound, or pharmaceutically acceptable salt or solvate thereof, wherein n is 1, and m is 1. Another embodiment provides the compound, or pharmaceutically acceptable salt or solvate thereof, wherein n is 2, and m is 1. Another embodiment provides the compound, or pharmaceutically acceptable salt or solvate thereof, wherein n is 1, and m is 2. Another embodiment provides the compound, or pharmaceutically acceptable salt or solvate thereof, wherein n is 0, and m is 1. Another embodiment provides the compound, or pharmaceutically acceptable salt or solvate thereof, wherein n is 1, and m is 0.

Another embodiment provides the compound of Formula (I), or pharmaceutically acceptable salt or solvate thereof, wherein X is:

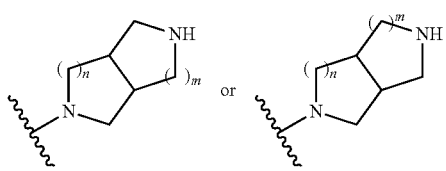

wherein m is 0, 1, 2, 3, or 4; and n is 0, 1, 2, 3, or 4. Another embodiment provides the compound, or pharmaceutically acceptable salt or solvate thereof, wherein X is:

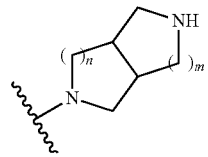

wherein m is 0, 1, 2, 3, or 4; and n is 0, 1, 2, 3, or 4. Another embodiment provides the compound, or pharmaceutically acceptable salt or solvate thereof, wherein X is:

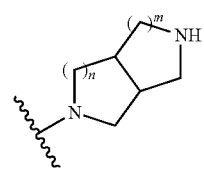

wherein m is 0, 1, 2, 3, or 4; and n is 0, 1, 2, 3, or 4. Another embodiment provides the compound, or pharmaceutically acceptable salt or solvate thereof, wherein n is 1, and m is 1. Another embodiment provides the compound, or pharmaceutically acceptable salt or solvate thereof, wherein n is 2, and m is 1. Another embodiment provides the compound, or pharmaceutically acceptable salt or solvate thereof, wherein n is 1, and m is 2. Another embodiment provides the compound, or pharmaceutically acceptable salt or solvate thereof, wherein n is 0, and m is 1. Another embodiment provides the compound, or pharmaceutically acceptable salt or solvate thereof, wherein n is 1, and m is 0.

Another embodiment provides the compound of Formula (I), or pharmaceutically acceptable salt or solvate thereof, wherein X is:

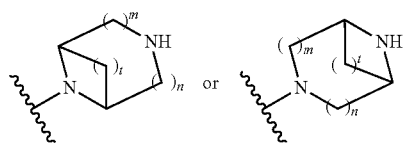

wherein m is 1, 2, or 3; n is 0, 1, 2, or 3; and t is 0, 1, 2, or 3. Another embodiment provides the compound, or pharmaceutically acceptable salt or solvate thereof, wherein X is:

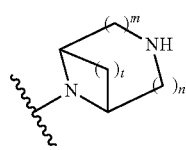

wherein m is 1, 2, or 3; n is 0, 1, 2, or 3; and t is 0, 1, 2, or 3. Another embodiment provides the compound, or pharmaceutically acceptable salt or solvate thereof, wherein X is:

wherein m is 1, 2, or 3; n is 0, 1, 2, or 3; and t is 0, 1, 2, or 3. Another embodiment provides the compound, or pharmaceutically acceptable salt or solvate thereof, wherein m is 1. Another embodiment provides the compound, or pharmaceutically acceptable salt or solvate thereof, wherein m is 2. Another embodiment provides the compound, or pharmaceutically acceptable salt or solvate thereof, wherein n is 0. Another embodiment provides the compound, or pharmaceutically acceptable salt or solvate thereof, wherein n is 1. Another embodiment provides the compound, or pharmaceutically acceptable salt or solvate thereof, wherein n is 2. Another embodiment provides the compound, or pharmaceutically acceptable salt or solvate thereof, wherein t is 0. Another embodiment provides the compound, or pharmaceutically acceptable salt or solvate thereof, wherein t is 1. Another embodiment provides the compound, or pharmaceutically acceptable salt or solvate thereof, wherein t is 2.

Another embodiment provides the compound of Formula (I), or pharmaceutically acceptable salt or solvate thereof, wherein X is:

wherein $R^2$ is hydrogen; m is 1, 2, or 3; n is 0, 1, 2, or 3; and t is 0, 1, 2, or 3. Another embodiment provides the compound, or pharmaceutically acceptable salt or solvate thereof, wherein X is:

wherein $R^2$ is hydrogen; m is 1, 2, or 3; n is 0, 1, 2, or 3; and t is 0, 1, 2, or 3. Another embodiment provides the compound, or pharmaceutically acceptable salt or solvate thereof, wherein X is:

wherein $R^2$ is hydrogen; m is 1, 2, or 3; n is 0, 1, 2, or 3; and t is 0, 1, 2, or 3. Another embodiment provides the compound, or pharmaceutically acceptable salt or solvate thereof, wherein $R^2$ is hydrogen. Another embodiment provides the compound, or pharmaceutically acceptable salt or solvate thereof, wherein m is 1. Another embodiment provides the compound, or pharmaceutically acceptable salt or solvate thereof, wherein m is 2. Another embodiment provides the compound, or pharmaceutically acceptable salt or solvate thereof, wherein n is 0. Another embodiment provides the compound, or pharmaceutically acceptable salt or solvate thereof, wherein n is 1. Another embodiment provides the compound, or pharmaceutically acceptable salt or solvate thereof, wherein n is 2. Another embodiment provides the compound, or pharmaceutically acceptable salt or solvate thereof, wherein t is 0. Another embodiment provides the compound, or pharmaceutically acceptable salt or solvate thereof, wherein t is 1. Another embodiment provides the compound, or pharmaceutically acceptable salt or solvate thereof, wherein t is 2.

Another embodiment provides the compound of Formula (I), or pharmaceutically acceptable salt or solvate thereof, wherein X is:

wherein m is 0, 1, 2, 3, or 4; and n is 0, 1, 2, 3, or 4. Another embodiment provides the compound, or pharmaceutically acceptable salt or solvate thereof, wherein X is:

wherein m is 0, 1, 2, 3, or 4; and n is 0, 1, 2, 3, or 4. Another embodiment provides the compound, or pharmaceutically acceptable salt or solvate thereof, wherein X is:

wherein m is 0, 1, 2, 3, or 4; and n is 0, 1, 2, 3, or 4. Another embodiment provides the compound, or pharmaceutically acceptable salt or solvate thereof, wherein n is 0. Another embodiment provides the compound, or pharmaceutically acceptable salt or solvate thereof, wherein n is 1. Another embodiment provides the compound, or pharmaceutically acceptable salt or solvate thereof, wherein n is 2. Another embodiment provides the compound, or pharmaceutically acceptable salt or solvate thereof, wherein m is 0. Another embodiment provides the compound, or pharmaceutically acceptable salt or solvate thereof, wherein m is 1. Another embodiment provides the compound, or pharmaceutically acceptable salt or solvate thereof, wherein m is 2.

Another embodiment provides the compound of Formula (I), or pharmaceutically acceptable salt or solvate thereof, wherein X is:

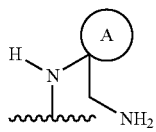

wherein ring A is an optionally substituted 4-, 5-, or 6-membered heterocyclic ring with an oxygen atom or a nitrogen atom. Another embodiment provides the compound, or pharmaceutically acceptable salt or solvate thereof, wherein ring A comprises a heterocyclic ring with an oxygen atom. Another embodiment provides the compound, or pharmaceutically acceptable salt or solvate thereof, wherein ring A comprises a heterocyclic ring with a nitrogen atom. Another embodiment provides the compound, or pharmaceutically acceptable salt or solvate thereof, wherein ring A is an optionally substituted 4-membered heterocyclic ring. Another embodiment provides the compound, or pharmaceutically acceptable salt or solvate thereof, wherein ring A is an optionally substituted 5-membered heterocyclic ring. Another embodiment provides the compound, or pharmaceutically acceptable salt or solvate thereof, wherein ring A is an optionally substituted 6-membered heterocyclic ring.

Another embodiment provides the compound of Formula (I), or pharmaceutically acceptable salt or solvate thereof, wherein $R^5$ is chloro. Another embodiment provides the compound, or pharmaceutically acceptable salt or solvate thereof, wherein $R^6$ is fluoro. Another embodiment provides the compound, or pharmaceutically acceptable salt or solvate thereof, wherein $R^7$ is fluoro. Another embodiment provides the compound, or pharmaceutically acceptable salt or solvate thereof, wherein $R^6$ is fluoro, and $R^7$ is fluoro. Another embodiment provides the compound, or pharmaceutically acceptable salt or solvate thereof, wherein $R^5$ is chloro, $R^6$ is fluoro, and $R^7$ is fluoro.

In another aspect is provided a compound, or pharmaceutically acceptable salt or solvate thereof, having the structure of Formula (II):

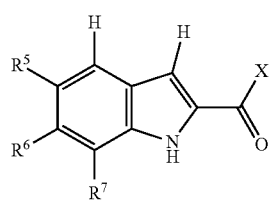

wherein, $R^5$ is selected from halogen;

$R^6$ is selected from hydrogen, or halogen;

$R^7$ is selected from hydrogen, or halogen;

X is selected from:

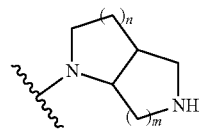

wherein m is 2, 3, or 4; and n is 0, 1, 2, 3, or 4;

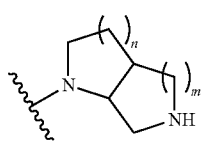

wherein m is 0, 1, 2, 3, or 4; and n is 0, 1, 2, 3, or 4;

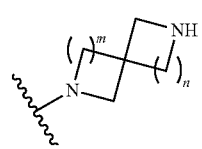

wherein m is 0, 1, 2, 3, or 4; and n is 2, 3, or 4; or

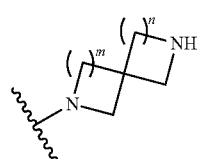

wherein m is 0, 1, 2, 3, or 4; and n is 0, 1, 2, 3, or 4.

Another embodiment provides the compound of Formula (II), or pharmaceutically acceptable salt or solvate thereof, wherein X is:

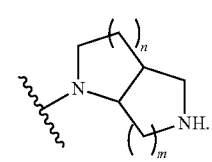

Another embodiment provides the compound, or pharmaceutically acceptable salt or solvate thereof, wherein n is 1, and m is 2. Another embodiment provides the compound, or pharmaceutically acceptable salt or solvate thereof, wherein n is 2, and m is 2. Another embodiment provides the compound, or pharmaceutically acceptable salt or solvate thereof, wherein n is 0, and m is 2.

Another embodiment provides the compound of Formula (II), or pharmaceutically acceptable salt or solvate thereof, wherein X is:

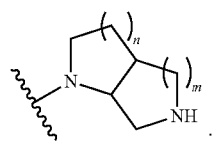

Another embodiment provides the compound, or pharmaceutically acceptable salt or solvate thereof, wherein n is 1, and m is 1. Another embodiment provides the compound, or pharmaceutically acceptable salt or solvate thereof, wherein n is 2, and m is 1. Another embodiment provides the compound, or pharmaceutically acceptable salt or solvate thereof, wherein n is 1, and m is 2. Another embodiment provides the compound, or pharmaceutically acceptable salt or solvate thereof, wherein n is 0, and m is 1. Another embodiment provides the compound, or pharmaceutically acceptable salt or solvate thereof, wherein n is 0, and m is 0.

Another embodiment provides the compound of Formula (II), or pharmaceutically acceptable salt or solvate thereof, wherein X is:

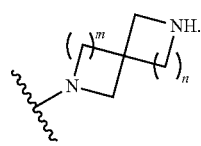

Another embodiment provides the compound, or pharmaceutically acceptable salt or solvate thereof, wherein n is 2, and m is 1. Another embodiment provides the compound, or pharmaceutically acceptable salt or solvate thereof, wherein n is 2, and m is 2.

Another embodiment provides the compound of Formula (II), or pharmaceutically acceptable salt or solvate thereof, wherein X is:

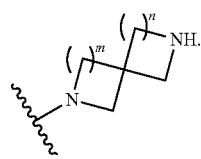

Another embodiment provides the compound, or pharmaceutically acceptable salt or solvate thereof, wherein n is 1, and m is 1. Another embodiment provides the compound, or pharmaceutically acceptable salt or solvate thereof, wherein n is 2, and m is 1. Another embodiment provides the compound, or pharmaceutically acceptable salt or solvate thereof, wherein n is 1, and m is 2. Another embodiment provides the compound, or pharmaceutically acceptable salt or solvate thereof, wherein n is 0, and m is 1.

Another embodiment provides the compound of Formula (II), or pharmaceutically acceptable salt or solvate thereof, wherein $R^5$ is chloro. Another embodiment provides the compound, or pharmaceutically acceptable salt or solvate thereof, wherein $R^6$ is fluoro. Another embodiment provides the compound, or pharmaceutically acceptable salt or solvate thereof, wherein $R^7$ is fluoro. Another embodiment provides the compound, or pharmaceutically acceptable salt or solvate thereof, wherein $R^6$ is fluoro, and $R^7$ is fluoro.

Another embodiment provides the compound, or pharmaceutically acceptable salt or solvate thereof, wherein $R^5$ is chloro, $R^6$ is fluoro, and $R^7$ is fluoro.

In another aspect is provided a compound, or pharmaceutically acceptable salt or solvate thereof, having the structure of Formula (III):

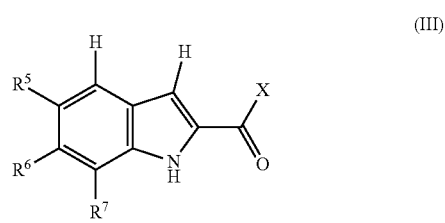

(III)

wherein,
$R^5$ is selected from halogen;
$R^6$ is selected from hydrogen, or halogen;
$R^7$ is selected from hydrogen, or halogen;
X is

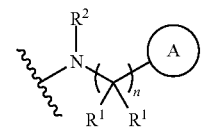

wherein n is 1, 2 or 3;
each $R^1$ is independently selected from hydrogen, optionally substituted alkyl, optionally substituted cycloalkyl, or optionally substituted cycloalkylalkyl;
$R^2$ is independently hydrogen or optionally substituted alkyl; and
Ring A is an optionally substituted 4, 5, 6, or 7-membered nitrogen containing heterocyclyl.

In some embodiments is provided a compound of Formula (III), or pharmaceutically acceptable salt or solvate thereof, having the structure of Formula (IIIa):

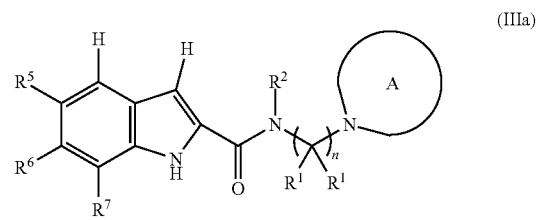

(IIIa)

wherein,
$R^5$ is selected from halogen;
$R^6$ is selected from hydrogen, or halogen;
$R^7$ is selected from hydrogen, or halogen;
Ring A is an optionally substituted 4, 5, 6, or 7-membered nitrogen containing N-linked heterocyclyl;
n is 1, 2 or 3;
each $R^1$ is independently selected from hydrogen, optionally substituted alkyl, optionally substituted cycloalkyl, or optionally substituted cycloalkylalkyl; and
$R^2$ is independently hydrogen or optionally substituted alkyl.

In some embodiments is provided a compound of Formula (III), or pharmaceutically acceptable salt or solvate thereof, having the structure of Formula (IIIb):

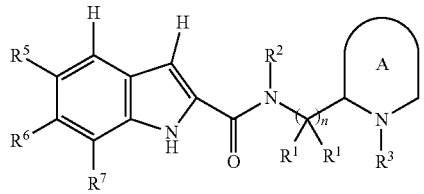

(IIIb)

wherein,
R⁵ is selected from halogen;
R⁶ is selected from hydrogen, or halogen;
R⁷ is selected from hydrogen, or halogen;
Ring A is an optionally substituted 4, 5, 6, or 7-membered nitrogen containing heterocyclyl;
n is 1, 2 or 3;
each R¹ is independently selected from hydrogen, optionally substituted alkyl, optionally substituted cycloalkyl, or optionally substituted cycloalkylalkyl;
R² is independently hydrogen or optionally substituted alkyl; and
R³ is independently hydrogen or optionally substituted alkyl.

In some embodiments is provided a compound of Formula (III), or pharmaceutically acceptable salt or solvate thereof, having the structure of Formula (IIIc):

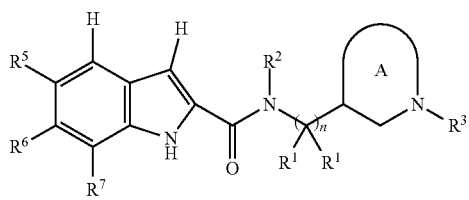

(IIIc)

wherein,
R⁵ is selected from halogen;
R⁶ is selected from hydrogen, or halogen;
R⁷ is selected from hydrogen, or halogen;
Ring A is an optionally substituted 4, 5, 6, or 7-membered nitrogen containing heterocyclyl;
n is 1, 2 or 3;
each R¹ is independently selected from hydrogen, optionally substituted alkyl, optionally substituted cycloalkyl, or optionally substituted cycloalkylalkyl;
R² is independently hydrogen or optionally substituted alkyl; and
R³ is independently hydrogen or optionally substituted alkyl.

Another embodiment provides the compound of Formula (IIIa-c), or pharmaceutically acceptable salt or solvate thereof, wherein each $R^1$ is independently selected from hydrogen, optionally substituted alkyl. Another embodiment provides the compound of Formula (IIIa-c), or pharmaceutically acceptable salt or solvate thereof, wherein each $R^2$ is hydrogen. Another embodiment provides the compound of Formula (IIIa), or pharmaceutically acceptable salt or solvate thereof, wherein n is 2. Another embodiment provides the compound of Formula (IIIb or c), or pharmaceutically acceptable salt or solvate thereof, wherein n is 1. Another embodiment provides the compound of Formula (IIIb or c), or pharmaceutically acceptable salt or solvate thereof, wherein $R^3$ is H.

Another embodiment provides the compound of Formula (IIIa-c), or pharmaceutically acceptable salt or solvate thereof, wherein $R^5$ is chloro. Another embodiment provides the compound, or pharmaceutically acceptable salt or solvate thereof, wherein $R^6$ is fluoro. Another embodiment provides the compound, or pharmaceutically acceptable salt or solvate thereof, wherein $R^7$ is fluoro. Another embodiment provides the compound, or pharmaceutically acceptable salt or solvate thereof, wherein $R^6$ is fluoro, and $R^7$ is fluoro. Another embodiment provides the compound, or pharmaceutically acceptable salt or solvate thereof, wherein $R^5$ is chloro, $R^6$ is fluoro, and $R^7$ is fluoro.

In some embodiments, the heterocyclic PAD4 inhibitory compound of Formula (I) or (II) described herein has a structure provided in Table 1.

TABLE 1

| Synthetic Chemistry Example | Compound Structure | Compound Name |
|---|---|---|
| 1 | 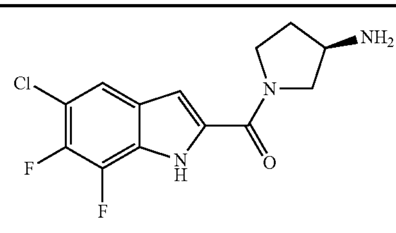 | (R)-(3-Aminopyrrolidin-1-yl)(5-chloro-6,7-difluoro-1H-indol-2-yl)methanone |
| 2 | 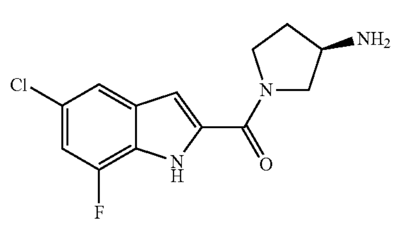 [SMILES: N[C@@H]1CCN(C(=O)c2cc3cc(Cl)cc(F)c3[nH]2)C1] | (R)-(3-Aminopyrrolidin-1-yl)(5-chloro-7-fluoro-1H-indol-2-yl)methanone |

TABLE 1-continued

| Synthetic Chemistry Example | Compound Structure | Compound Name |
|---|---|---|
| 3 | 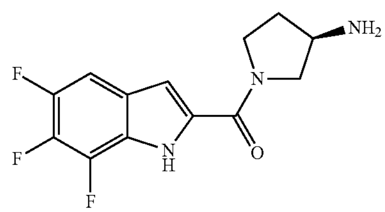 [SMILES: N[C@@H]1CCN(C(=O)c2cc3cc(F)c(F)c(F)c3[nH]2)C1] | (R)-(3-Aminopyrrolidin-1-yl)(5,6,7-trifluoro-1H-indol-2-yl)methanone |
| 4 | 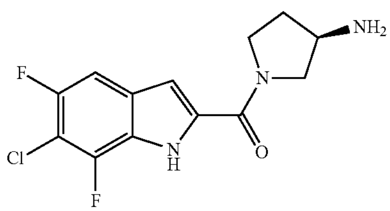 [SMILES: N[C@@H]1CCN(C(=O)c2cc3cc(F)c(Cl)c(F)c3[nH]2)C1] | (R)-(3-Aminopyrrolidin-1-yl)(6-chloro-5,7-difluoro-1H-indol-2-yl)methanone |
| 5 | 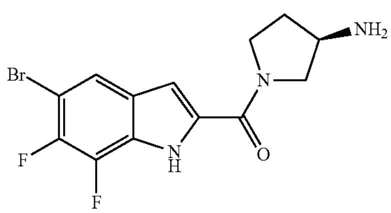 | (R)-(3-Aminopyrrolidin-1-yl)(5-bromo-6,7-difluoro-1H-indol-2-yl)methanone |
| 6 | 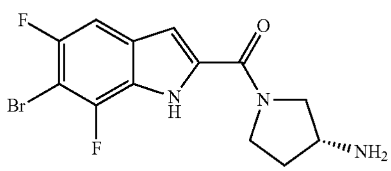 [SMILES: N[C@@H]1CCN(C(=O)c2cc3cc(F)c(Br)c(F)c3[nH]2)C1] | (R)-(3-Aminopyrrolidin-1-yl)(6-bromo-5,7-difluoro-1H-indol-2-yl)methanone |
| 7 | 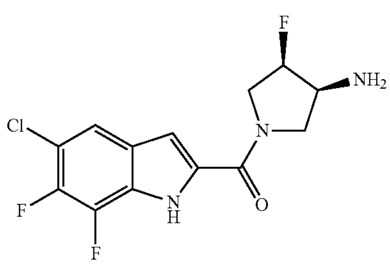 [SMILES: N[C@H]1CN(C(=O)c2cc3cc(Cl)c(F)c(F)c3[nH]2)C[C@H]1F] | ((3S,4R)-3-Amino-4-fluoro-pyrrolidin-1-yl)-(5-chloro-6,7-difluoro-1H-indol-2-yl)-methanone |
| 8 | 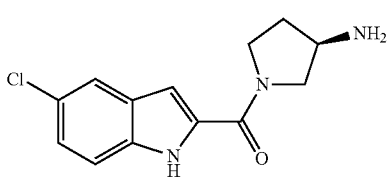 [SMILES: N[C@@H]1CCN(C(=O)c2cc3cc(Cl)ccc3[nH]2)C1] | (R)-(3-Aminopyrrolidin-1-yl)(5-chloro-1H-indol-2-yl)methanone |
| 9 | 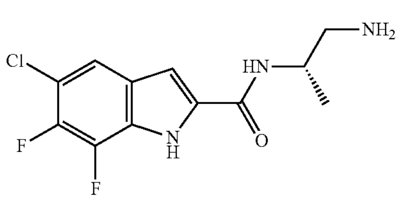 [SMILES: C[C@@H](CN)NC(=O)c1cc2cc(Cl)c(F)c(F)c2[nH]1] | (S)-N-(1-Aminopropan-2-yl)-5-chloro-6,7-difluoro-1H-indole-2-carboxamide |

TABLE 1-continued

| Synthetic Chemistry Example | Compound Structure | Compound Name |
|---|---|---|
| 10 | 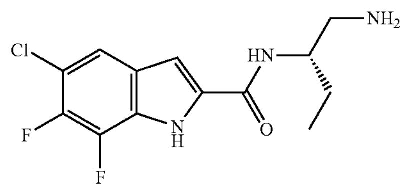 [SMILES: CC[C@@H](CN)NC(=O)c1cc2cc(Cl)c(F)c(F)c2[nH]1] | (S)-N-(1-Aminobutan-2-yl)-5-chloro-6,7-difluoro-1H-indole-2-carboxamide |
| 11 | 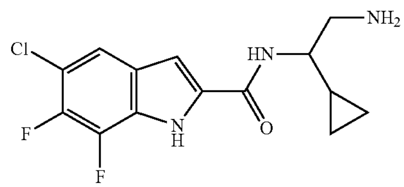 [SMILES: NCC(NC(=O)c1cc2cc(Cl)c(F)c(F)c2[nH]1)C1CC1] | N-(2-Amino-1-cyclopropylethyl)-5-chloro-6,7-difluoro-1H-indole-2-carboxamide |
| 12 | 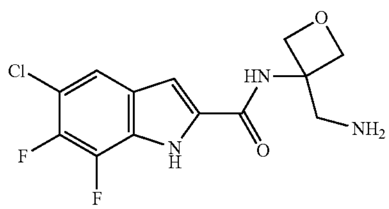 [SMILES: NCC1(NC(=O)c2cc3cc(Cl)c(F)c(F)c3[nH]2)COC1] | N-(3-(Aminomethyl)oxetan-3-yl)-5-chloro-6,7-difluoro-1H-indole-2-carboxamide |
| 13 | 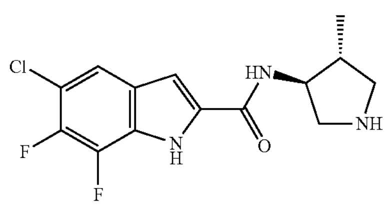 [SMILES: C[C@@H]1CNC[C@H]1NC(=O)c1cc2cc(Cl)c(F)c(F)c2[nH]1] | 5-Chloro-6,7-difluoro-N-((3S,4R)-4-methylpyrrolidin-3-yl)-1H-indole-2-carboxamide |
| 14 | 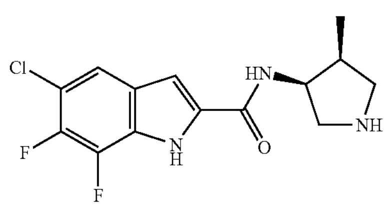 [SMILES: C[C@H]1CNC[C@H]1NC(=O)c1cc2cc(Cl)c(F)c(F)c2[nH]1] | 5-Chloro-6,7-difluoro-N-((3S,4S)-4-methylpyrrolidin-3-yl)-1H-indole-2-carboxamide |
| 15 | 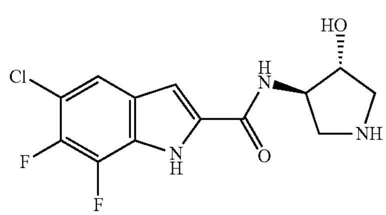 [SMILES: O=C(N[C@@H]1CNC[C@H]1O)c1cc2cc(Cl)c(F)c(F)c2[nH]1] | 5-Chloro-6,7-difluoro-N-((3R,4R)-4-hydroxypyrrolidin-3-yl)-1H-indole-2-carboxamide |
| 16 | 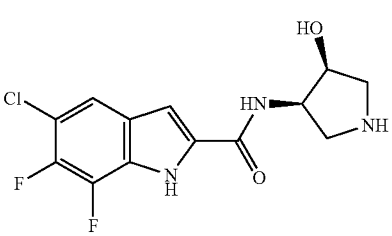 [SMILES: O=C(N[C@@H]1CNC[C@@H]1O)c1cc2cc(Cl)c(F)c(F)c2[nH]1] | 5-Chloro-6,7-difluoro-N-((3R,4S)-4-hydroxypyrrolidin-3-yl)-1H-indole-2-carboxamide |

TABLE 1-continued

| Synthetic Chemistry Example | Compound Structure | Compound Name |
|---|---|---|
| 17 | 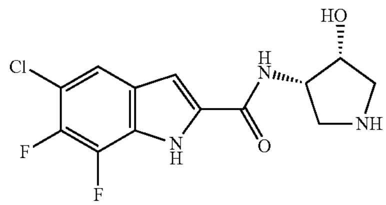 [SMILES: O=C(N[C@H]1CNC[C@H]1O)c1cc2cc(Cl)c(F)c(F)c2[nH]1] | 5-Chloro-6,7-difluoro-N-((3S,4R)-4-hydroxypyrrolidin-3-yl)-1H-indole-2-carboxamide |
| 18 | 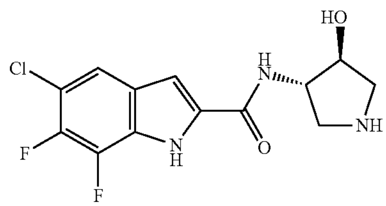 [SMILES: O=C(N[C@H]1CNC[C@@H]1O)c1cc2cc(Cl)c(F)c(F)c2[nH]1] | 5-Chloro-6,7-difluoro-N-((3S,4S)-4-hydroxypyrrolidin-3-yl)-1H-indole-2-carboxamide |
| 19 | 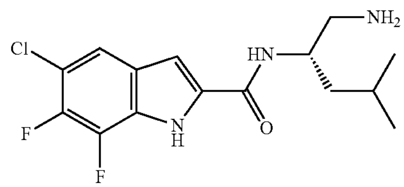 [SMILES: CC(C)C[C@@H](CN)NC(=O)c1cc2cc(Cl)c(F)c(F)c2[nH]1] | (S)-N-(1-Amino-4-methylpentan-2-yl)-5-chloro-6,7-difluoro-1H-indole-2-carboxamide |
| 20 | 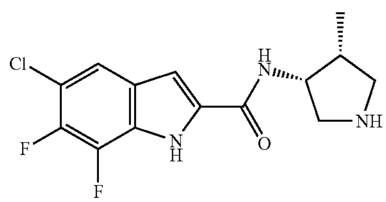 [SMILES: C[C@@H]1CNC[C@@H]1NC(=O)c1cc2cc(Cl)c(F)c(F)c2[nH]1] | 5-Chloro-6,7-difluoro-N-((3R,4R)-4-methylpyrrolidin-3-yl)-1H-indole-2-carboxamide |
| 21 | 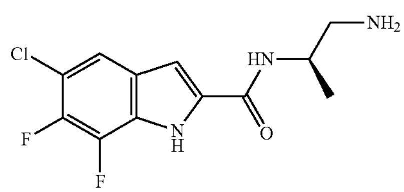 [SMILES: C[C@H](CN)NC(=O)c1cc2cc(Cl)c(F)c(F)c2[nH]1] | (R)-N-(1-Aminopropan-2-yl)-5-chloro-6,7-difluoro-1H-indole-2-carboxamide |
| 22 | 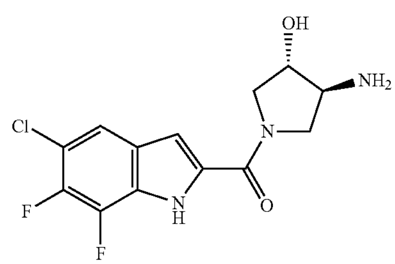 [SMILES: N[C@H]1CN(C(=O)c2cc3cc(Cl)c(F)c(F)c3[nH]2)C[C@@H]1O] | ((3S,4S)-3-Amino-4-hydroxypyrrolidin-1-yl)(5-chloro-6,7-difluoro-1H-indol-2-yl)methanone |
| 23 | 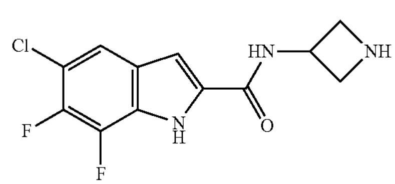 [SMILES: O=C(NC1CNC1)c1cc2cc(Cl)c(F)c(F)c2[nH]1] | N-(Azetidin-3-yl)-5-chloro-6,7-difluoro-1H-indole-2-carboxamide |

TABLE 1-continued

| Synthetic Chemistry Example | Compound Structure | Compound Name |
|---|---|---|
| 24 | 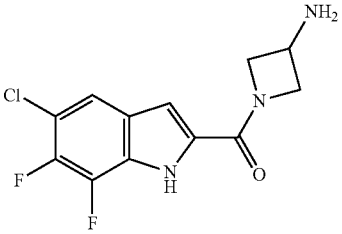 [SMILES: NC1CN(C(=O)c2cc3cc(Cl)c(F)c(F)c3[nH]2)C1] | (3-Aminoazetidin-1-yl)(5-chloro-6,7-difluoro-1H-indol-2-yl)methanone |
| 25 | 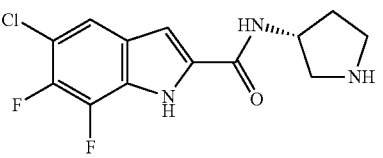 [SMILES: O=C(N[C@@H]1CCNC1)c1cc2cc(Cl)c(F)c(F)c2[nH]1] | (R)-5-Chloro-6,7-difluoro-N-(pyrrolidin-3-yl)-1H-indole-2-carboxamide |
| 26 | 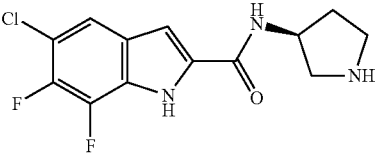 [SMILES: O=C(N[C@H]1CCNC1)c1cc2cc(Cl)c(F)c(F)c2[nH]1] | (S)-5-Chloro-6,7-difluoro-N-(pyrrolidin-3-yl)-1H-indole-2-carboxamide |
| 27 | 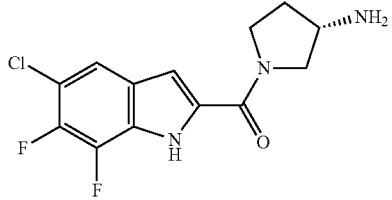 [SMILES: N[C@H]1CCN(C(=O)c2cc3cc(Cl)c(F)c(F)c3[nH]2)C1] | (S)-(3-Aminopyrrolidin-1-yl)(5-chloro-6,7-difluoro-1H-indol-2-yl)methanone |
| 28 | 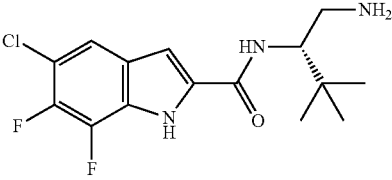 [SMILES: CC(C)(C)[C@@H](CN)NC(=O)c1cc2cc(Cl)c(F)c(F)c2[nH]1] | (S)-N-(1-Amino-3,3-dimethylbutan-2-yl)-5-chloro-6,7-difluoro-1H-indole-2-carboxamide |
| 29 | 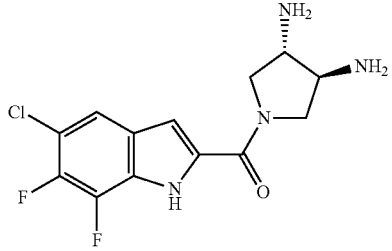 [SMILES: N[C@H]1CN(C(=O)c2cc3cc(Cl)c(F)c(F)c3[nH]2)C[C@@H]1N] | (5-Chloro-6,7-difluoro-1H-indol-2-yl)((3S,4S)-3,4-diaminopyrrolidin-1-yl)methanone |
| 30 | 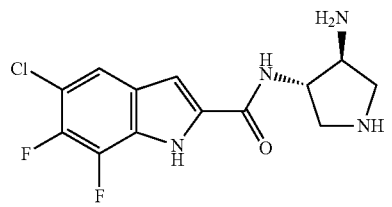 [SMILES: N[C@H]1CNC[C@@H]1NC(=O)c1cc2cc(Cl)c(F)c(F)c2[nH]1] | N-((3S,4S)-4-Aminopyrrolidin-3-yl)-5-chloro-6,7-difluoro-1H-indole-2-carboxamide |

TABLE 1-continued

| Synthetic Chemistry Example | Compound Structure | Compound Name |
|---|---|---|
| 31 | (structure; mixture) | N-((3R,4S)-4-Aminopyrrolidin-3-yl)-5-chloro-6,7-difluoro-1H-indole-2-carboxamide and N-((3S,4R)-4-Aminopyrrolidin-3-yl)-5-chloro-6,7-difluoro-1H-indole-2-carboxamide |
| 32 | (structure) | ((3S,4R)-3-Amino-4-hydroxypyrrolidin-1-yl)(5-chloro-6,7-difluoro-1H-indol-2-yl)methanone |
| 33 | (structure) | 5-Chloro-6,7-difluoro-N-((3S,4S)-4-methoxypyrrolidin-3-yl)-1H-indole-2-carboxamide |
| 34 | (structure) | 5-Chloro-6,7-difluoro-N-((3R,4R)-4-methoxypyrrolidin-3-yl)-1H-indole-2-carboxamide |
| 35 | (structure) | ((3S,4S)-3-Amino-4-methoxypyrrolidin-1-yl)(5-chloro-6,7-difluoro-1H-indol-2-yl)methanone |
| 36 | (structure) | 5-Chloro-6,7-difluoro-N-((3R,4S)-4-methylpyrrolidin-3-yl)-1H-indole-2-carboxamide |

TABLE 1-continued

| Synthetic Chemistry Example | Compound Structure | Compound Name |
|---|---|---|
| 37 | 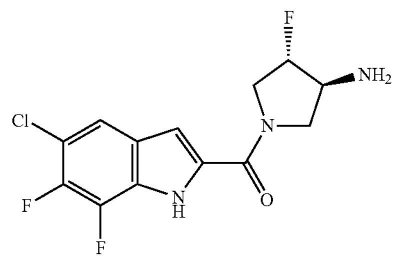 [SMILES: N[C@H]1CN(C(=O)c2cc3cc(Cl)c(F)c(F)c3[nH]2)C[C@@H]1F] | ((3S,4S)-3-Amino-4-fluoropyrrolidin-1-yl)(5-chloro-6,7-difluoro-1H-indol-2-yl)methanone |
| 38 | 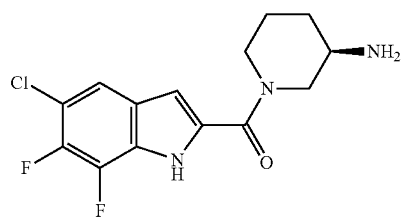 [SMILES: N[C@@H]1CCCN(C(=O)c2cc3cc(Cl)c(F)c(F)c3[nH]2)C1] | (R)-(3-Aminopiperidin-1-yl)(5-chloro-6,7-difluoro-1H-indol-2-yl)methanone |
| 39 | 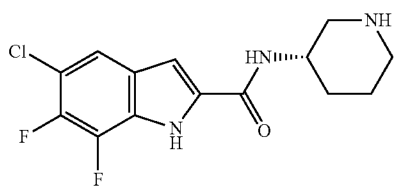 [SMILES: O=C(N[C@H]1CCCNC1)c1cc2cc(Cl)c(F)c(F)c2[nH]1] | (S)-5-Chloro-6,7-difluoro-N-(piperidin-3-yl)-1H-indole-2-carboxamide |
| 40 | 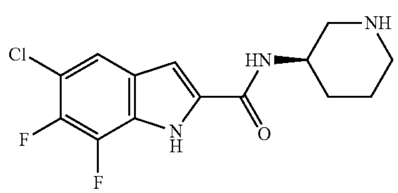 [SMILES: O=C(N[C@@H]1CCCNC1)c1cc2cc(Cl)c(F)c(F)c2[nH]1] | (R)-5-Chloro-6,7-difluoro-N-(piperidin-3-yl)-1H-indole-2-carboxamide |
| 41 | 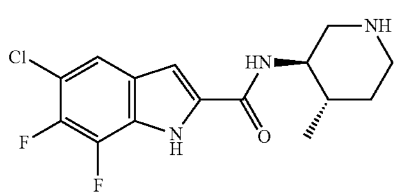 [SMILES: C[C@H]1CCNC[C@@H]1NC(=O)c1cc2cc(Cl)c(F)c(F)c2[nH]1] | 5-Chloro-6,7-difluoro-N-((3R,4S)-4-methylpiperidin-3-yl)-1H-indole-2-carboxamide |
| 42 | 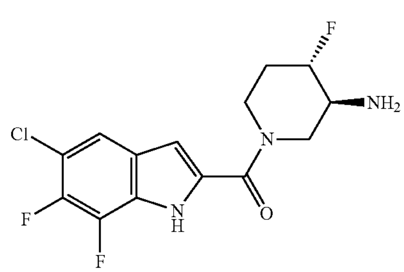 [SMILES: N[C@H]1CN(C(=O)c2cc3cc(Cl)c(F)c(F)c3[nH]2)CC[C@@H]1F] | ((3S,4S)-3-Amino-4-fluoropiperidin-1-yl)(5-chloro-6,7-difluoro-1H-indol-2-yl)methanone |

TABLE 1-continued

| Synthetic Chemistry Example | Compound Name |
|---|---|
| 43 | ((3S,4R)-3-Amino-4-fluoropiperidin-1-yl)(5-chloro-6,7-difluoro-1H-indol-2-yl)methanone |
| 44 | (R)-(3-Aminopyrrolidin-1-yl)(5,6-dichloro-1H-indol-2-yl)methanone |
| 45 | (R)-(3-Aminopyrrolidin-1-yl)(5,7-dichloro-1H-indol-2-yl)methanone |
| 46 | (R)-(3-Aminopyrrolidin-1-yl)(6-chloro-1H-indol-2-yl)methanone |
| 47 | (R)-(3-Aminopyrrolidin-1-yl)(7-bromo-5-chloro-1H-indol-2-yl)methanone |
| 48 | (R)-(3-Aminopyrrolidin-1-yl)(5-bromo-1H-indol-2-yl)methanone |
| 49 | (R)-(3-Aminopyrrolidin-1-yl)(5-fluoro-1H-indol-2-yl)methanone |

TABLE 1-continued

| Synthetic Chemistry Example | Compound Structure | Compound Name |
|---|---|---|
| 50 | 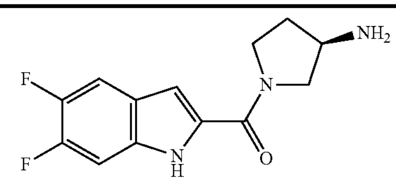 | (R)-(3-Aminopyrrolidin-1-yl)(5,6-difluoro-1H-indol-2-yl)methanone |
| 51 | 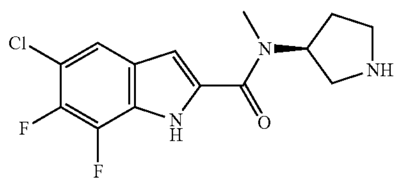 [SMILES: CN(C(=O)c1cc2cc(Cl)c(F)c(F)c2[nH]1)[C@H]1CCNC1] | (S)-5-chloro-6,7-difluoro-N-methyl-N-(pyrrolidin-3-yl)-1H-indole-2-carboxamide |
| 52 | 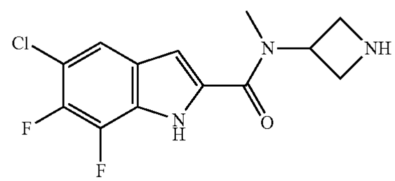 [SMILES: CN(C(=O)c1cc2cc(Cl)c(F)c(F)c2[nH]1)C1CNC1] | N-(azetidin-3-yl)-5-chloro-6,7-difluoro-N-methyl-1H-indole-2-carboxamide |
| 53 | 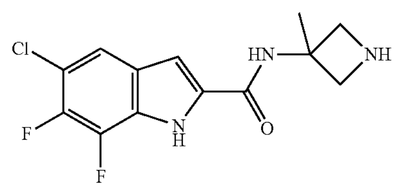 [SMILES: CC1(NC(=O)c2cc3cc(Cl)c(F)c(F)c3[nH]2)CNC1] | 5-chloro-6,7-difluoro-N-(3-methylazetidin-3-yl)-1H-indole-2-carboxamide |
| 54 | 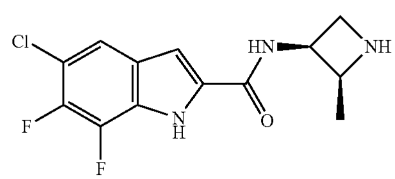 [SMILES: C[C@@H]1NC[C@@H]1NC(=O)c1cc2cc(Cl)c(F)c(F)c2[nH]1] | 5-chloro-6,7-difluoro-N-((2S,3S)-2-methylazetidin-3-yl)-1H-indole-2-carboxamide |
| 55 | 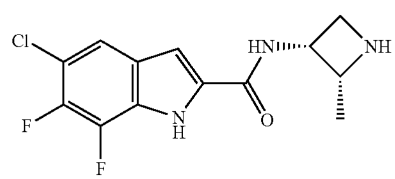 [SMILES: C[C@H]1NC[C@H]1NC(=O)c1cc2cc(Cl)c(F)c(F)c2[nH]1] | 5-chloro-6,7-difluoro-N-((2R,3R)-2-methylazetidin-3-yl)-1H-indole-2-carboxamide |
| 56 | 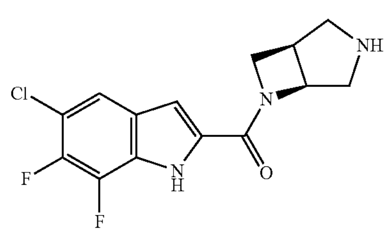 [SMILES: O=C(c1cc2cc(Cl)c(F)c(F)c2[nH]1)N1C[C@H]2CNC[C@H]21] | (1R,5S)-3,6-diazabicyclo[3.2.0]heptan-6-yl(5-chloro-6,7-difluoro-1H-indol-2-yl)methanone |
| 57 | 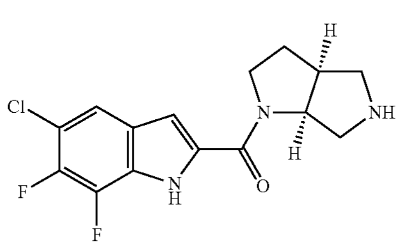 [SMILES: O=C(c1cc2cc(Cl)c(F)c(F)c2[nH]1)N1CC[C@H]2CNC[C@H]21] | (5-chloro-6,7-difluoro-1H-indol-2-yl)((3aS,6aS)-hexahydropyrrolo[3,4-b]pyrrol-1(2H)-yl)methanone |

TABLE 1-continued

| Synthetic Chemistry Example | Compound Structure | Compound Name |
|---|---|---|
| 58 | 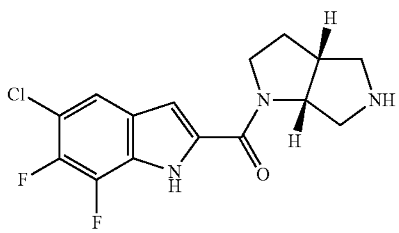 [SMILES: O=C(c1cc2cc(Cl)c(F)c(F)c2[nH]1)N1CC[C@@H]2CNC[C@@H]21] | (5-chloro-6,7-difluoro-1H-indol-2-yl)((3aR,6aR)-hexahydropyrrolo[3,4-b]pyrrol-1(2H)-yl)methanone |
| 59 | 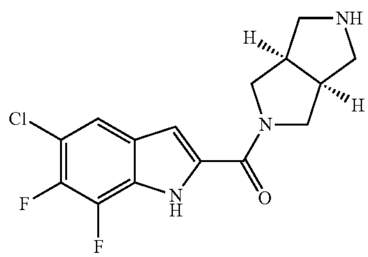 [SMILES: O=C(c1cc2cc(Cl)c(F)c(F)c2[nH]1)N1C[C@H]2CNC[C@H]2C1] | (5-chloro-6,7-difluoro-1H-indol-2-yl)((3aR,6aS)-hexahydropyrrolo[3,4-c]pyrrol-2(1H)-yl)methanone |
| 60 | 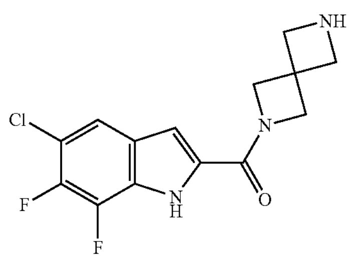 [SMILES: O=C(c1cc2cc(Cl)c(F)c(F)c2[nH]1)N1CC2(CNC2)C1] | (5-chloro-6,7-difluoro-1H-indol-2-yl)(2,6-diazaspiro[3.3]heptan-2-yl)methanone |
| 61 | 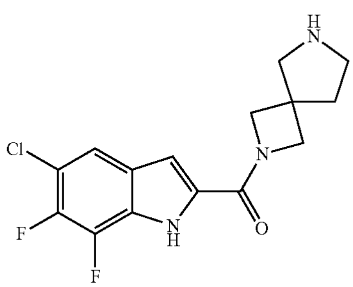 [SMILES: O=C(c1cc2cc(Cl)c(F)c(F)c2[nH]1)N1CC2(CCNC2)C1] | (5-chloro-6,7-difluoro-1H-indol-2-yl)(2,6-diazaspiro[3.4]octan-2-yl)methanone |
| 62 | 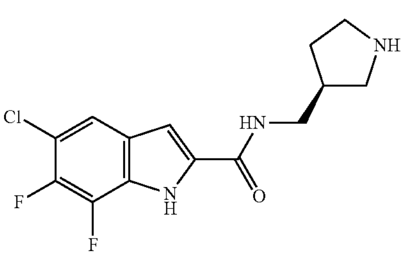 [SMILES: O=C(NC[C@H]1CCNC1)c1cc2cc(Cl)c(F)c(F)c2[nH]1] | (S)-5-chloro-6,7-difluoro-N-(pyrrolidin-3-ylmethyl)-1H-indole-2-carboxamide |
| 63 | 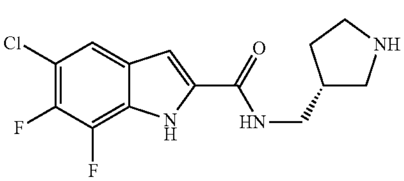 [SMILES: O=C(NC[C@@H]1CCNC1)c1cc2cc(Cl)c(F)c(F)c2[nH]1] | (R)-5-chloro-6,7-difluoro-N-(pyrrolidin-3-ylmethyl)-1H-indole-2-carboxamide |

TABLE 1-continued

| Synthetic Chemistry Example | Compound Structure | Compound Name |
|---|---|---|
| 64 | 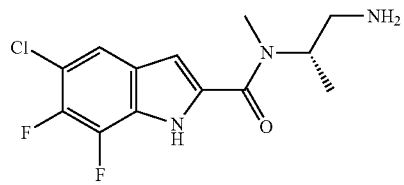 [SMILES: C[C@@H](CN)N(C)C(=O)c1cc2cc(Cl)c(F)c(F)c2[nH]1] | (S)-N-(1-aminopropan-2-yl)-5-chloro-6,7-difluoro-N-methyl-1H-indole-2-carboxamide |
| 65 | 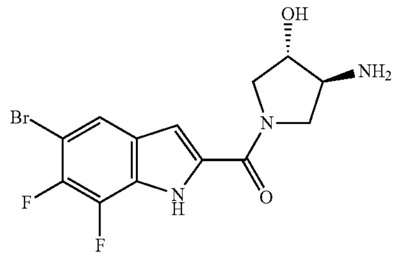 | ((3S,4S)-3-amino-4-hydroxypyrrolidin-1-yl)(5-bromo-6,7-difluoro-1H-indol-2-yl)methanone |
| 66 | 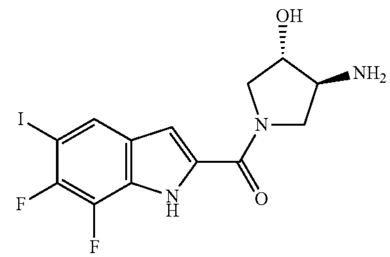 [SMILES: N[C@H]1CN(C(=O)c2cc3cc(I)c(F)c(F)c3[nH]2)C[C@@H]1O] | ((3S,4S)-3-amino-4-hydroxypyrrolidin-1-yl)(6,7-difluoro-5-iodo-1H-indol-2-yl)methanone |
| 67 | 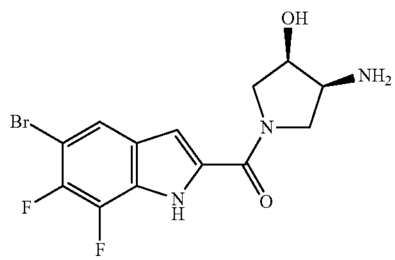 | ((3S,4R)-3-amino-4-hydroxypyrrolidin-1-yl)(5-bromo-6,7-difluoro-1H-indol-2-yl)methanone |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis:

Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the heterocyclic PAD4 inhibitory compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heterocyclic PAD4 inhibitory compound described herein is administered as a pure chemical. In other embodiments, the heterocyclic PAD4 inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one heterocyclic PAD4 inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I), (II), (III) or a compound disclosed in Table 1, or a pharmaceutically acceptable salt thereof.

In certain embodiments, the heterocyclic PAD4 inhibitory compound as described by Formula (I), (II), (III) or a compound disclosed in Table 1, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the heterocyclic PAD4 inhibitory compound as described by Formula (I), (II), (III) or a compound disclosed in Table 1, or pharmaceutically acceptable salt thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heterocyclic PAD4 inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

In some embodiments, described herein is a method of treating rheumatoid arthritis in a patient in need thereof comprising administering to the patient a compound of Formula (I), (II), (III) or a pharmaceutically acceptable salt or solvate thereof. In some embodiments, described herein is a method of treating rheumatoid arthritis in a patient in need thereof comprising administering to the patient a compound disclosed in Table 1, or a pharmaceutically acceptable salt or solvate thereof. In some embodiments, also described herein is a method of treating rheumatoid arthritis in a patient in need thereof comprising administering to the patient a pharmaceutical composition comprising a compound of Formula (I), (II), (III) or a pharmaceutically acceptable salt or solvate thereof, and a pharmaceutically acceptable excipient. In some embodiments, also described herein is a method of treating rheumatoid arthritis in a patient in need thereof comprising administering to the patient a pharmaceutical composition comprising a compound disclosed in Table 1, or a pharmaceutically acceptable salt or solvate thereof, and a pharmaceutically acceptable excipient.

One embodiment provides a method of treating an autoimmune disease or disorder in a patient in need thereof comprising administering to the patient a compound of Formula (I), (II), (III) or pharmaceutically acceptable salt or solvate thereof. Another embodiment provides the method wherein the autoimmune disease or disorder is rheumatoid arthritis.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heterocyclic PAD4 inhibitory compounds disclosed herein are synthesized according to the following examples. As used below, and throughout the description of the invention, the following abbreviations, unless otherwise indicated, shall be understood to have the following meanings:
° C. degrees Celsius
$\delta_H$ chemical shift in parts per million downfield from tetramethylsilane
DABCO 1,4-diazabicyclo[2.2.2]octane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
µ micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
NCS N-chlorosuccinimide
NIS N-iodosuccinimide
nm nanometer(s)
NMR nuclear magnetic resonance
pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran General Scheme 1 for the synthesis of heterocyclic PAD4 inhibitory compounds.

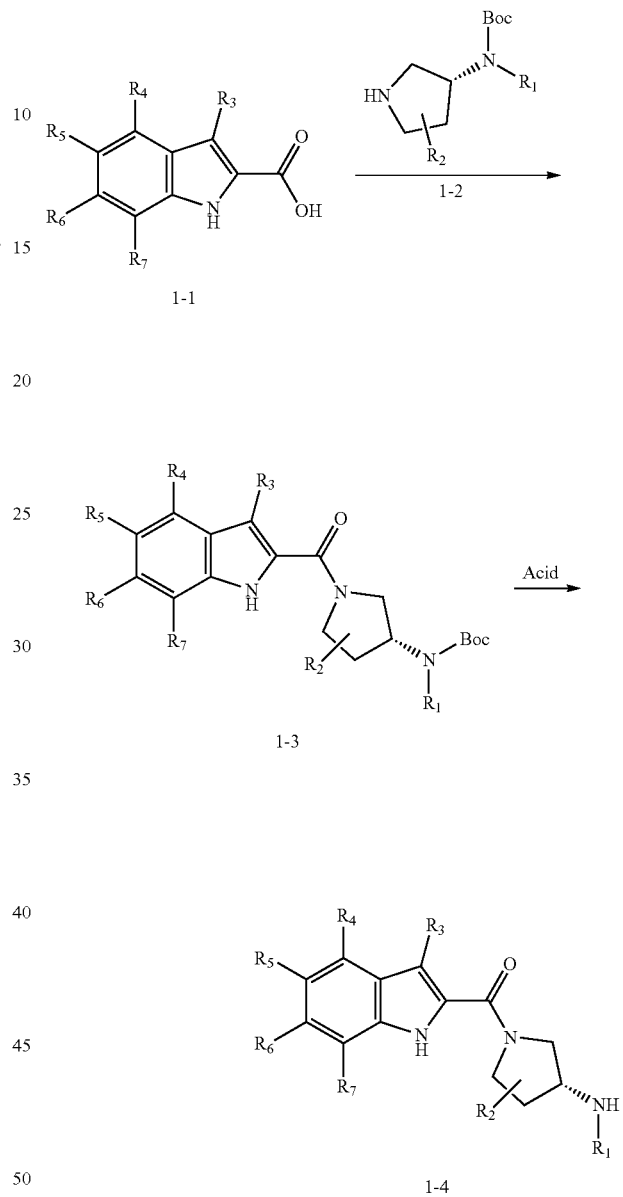

Scheme 1

Compounds of formula 1-3 are prepared by amide bond formation between compounds of formula 1-1 with compounds of formula 1-2. Compounds of formula 1-3 are then be deprotected by acids to give the desired compounds of formula 1-4. For example, compound of formula 1-1 is treated with 1-[bis(dimethylamino)methylene]-1H-1,2,3-triazolo[4,5-b]pyridinium 3-oxid hexafluorophosphate (HATU), compound of formula 1-2 and N,N-diisopropylethylamine (DIEA) in a solvent such as DMF to give a compound of formula 1-3. A compound of formula 1-3 is then deprotected by acidic solutions such as trifluoroacetic acid in dichloromethane to give compounds of formula 1-4.

General Scheme 2 for the synthesis of heterocyclic PAD4 inhibitory compounds.

Scheme 2

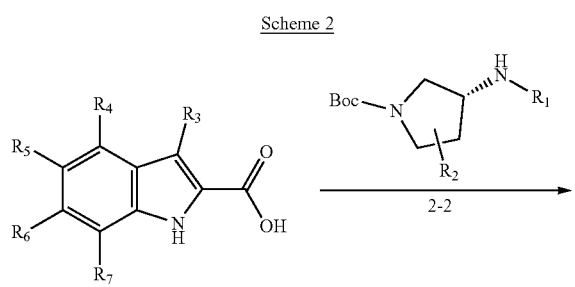

2-1

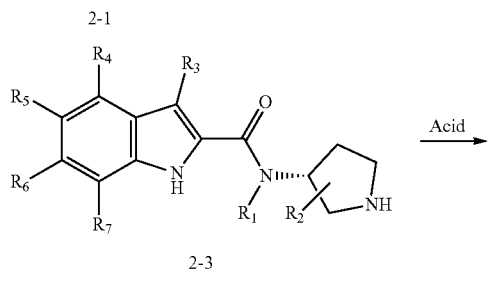

2-3

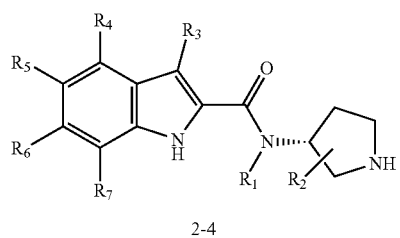

2-4

Compounds of formula 2-3 are prepared by amide bond formation between compounds of formula 2-1 with compounds of formula 2-2. Compounds of formula 2-3 are then deprotected by acids to give the desired compounds of formula 2-4. For example, compound of formula 2-1 is treated with 1-[bis(dimethylamino)methylene]-1H-1,2,3-triazolo[4,5-b]pyridinium 3-oxid hexafluorophosphate (HATU), compound of formula 2-2 and N,N-diisopropylethylamine (DIEA) in a solvent such as DMF to give a compound of formula 2-3. A compound of formula 2-3 is then deprotected by acidic solutions such as trifluoroacetic acid in dichloromethane to give compounds of formula 2-4.

General Scheme 3 for the synthesis of heterocyclic PAD4 inhibitory compounds.

Scheme 3

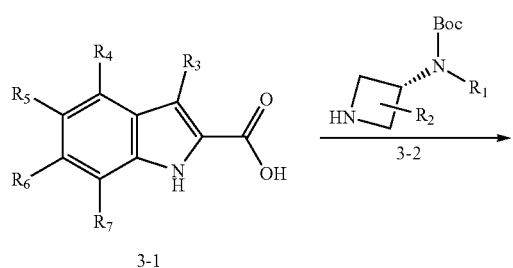

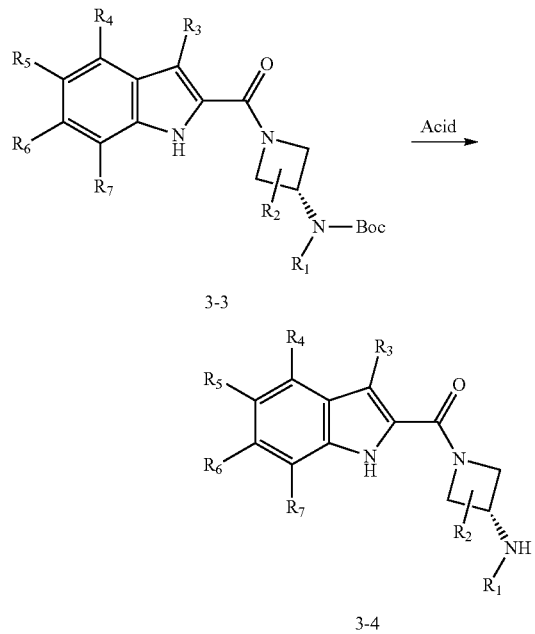

Compounds of formula 3-3 are prepared by amide bond formation between compounds of formula 3-1 with compounds of formula 3-2. Compounds of formula 3-3 are then deprotected by acids to give the desired compounds of formula 3-4. For example, compound of formula 3-1 is treated with 1-[bis(dimethylamino)methylene]-1H-1,2,3-triazolo[4,5-b]pyridinium 3-oxid hexafluorophosphate (HATU), compound of formula 3-2 and N,N-diisopropylethylamine (DIEA) in a solvent such as DMF to give a compound of formula 3-3. A compound of formula 3-3 is then deprotected by acidic solutions such as trifluoroacetic acid in dichloromethane to give compounds of formula 3-4.

General Scheme 4 for the synthesis of heterocyclic PAD4 inhibitory compounds.

Scheme 4

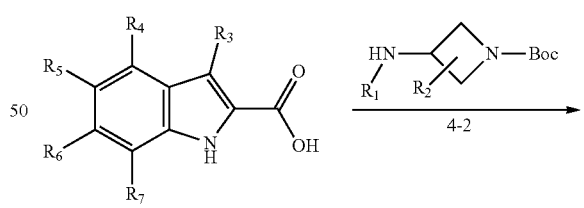

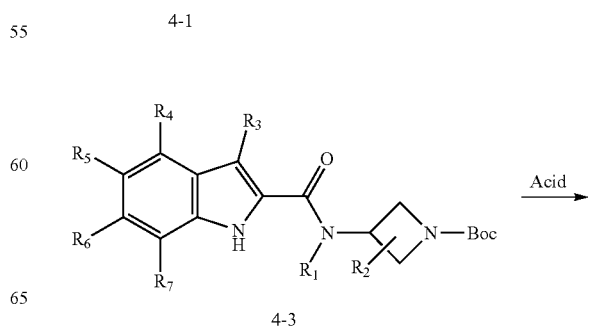

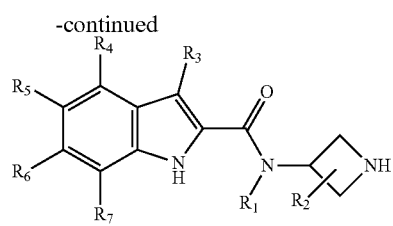

Compounds of formula 4-3 are prepared by amide bond formation between compounds of formula 4-1 with compounds of formula 4-2. Compounds of formula 4-3 are then deprotected by acids to give the desired compounds of formula 4-4. For example, compound of formula 4-1 is treated with 1-[bis(dimethylamino)methylene]-1H-1,2,3-triazolo[4,5-b]pyridinium 3-oxid hexafluorophosphate (HATU), compound of formula 4-2 and N,N-diisopropylethylamine (DIEA) in a solvent such as DMF to give a compound of formula 4-3. A compound of formula 4-3 is then deprotected by acidic solutions such as trifluoroacetic acid in dichloromethane to give compounds of formula 4-4.

General Scheme 5 for the synthesis of heterocyclic PAD4 inhibitory compounds.

Compounds of formula 5-3 are prepared by amide bond formation between compounds of formula 5-1 with compounds of formula 5-2. Compounds of formula 5-3 are then deprotected by acids to give the desired compounds of formula 5-4. For example, compound of formula 5-1 is treated with 1-[bis(dimethylamino)methylene]-1H-1,2,3-triazolo[4,5-b]pyridinium 3-oxid hexafluorophosphate (HATU), compound of formula 5-2 and N,N-diisopropylethylamine (DIEA) in a solvent such as DMF to give a compound of formula 5-3. A compound of formula 5-3 is then deprotected by acidic solutions such as trifluoroacetic acid in dichloromethane to give compounds of formula 5-4.

Example 1: Synthesis of (R)-(3-Aminopyrrolidin-1-yl)(5-chloro-6,7-difluoro-1H-indol-2-yl)methanone

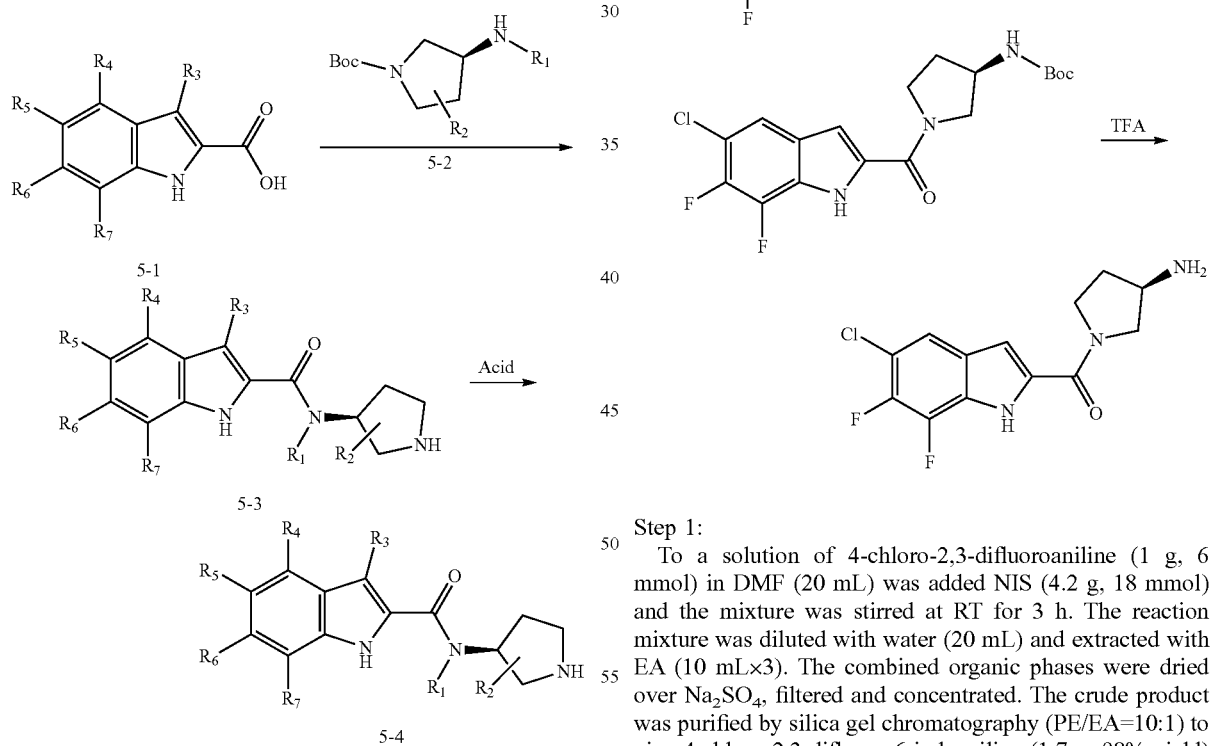

Step 1:
To a solution of 4-chloro-2,3-difluoroaniline (1 g, 6 mmol) in DMF (20 mL) was added NIS (4.2 g, 18 mmol) and the mixture was stirred at RT for 3 h. The reaction mixture was diluted with water (20 mL) and extracted with EA (10 mL×3). The combined organic phases were dried over $Na_2SO_4$, filtered and concentrated. The crude product was purified by silica gel chromatography (PE/EA=10:1) to give 4-chloro-2,3-difluoro-6-iodoaniline (1.7 g, 98% yield) as a yellow oil. $^1$H NMR (400 MHz, DMSO-$d_6$): δ 7.63-7.60 (m, 1H), 5.67 (s, 2H).

Step 2:
4-Chloro-2,3-difluoro-6-iodoaniline (700 mg, 2.4 mmol), pyruvic acid (639 mg, 7.2 mmol) and DABCO (814 mg, 7.2 mmol) were dissolved in DMF (15 mL). The solution was degassed and palladium acetate (200 mg) was added. The reaction mixture was heated at 100° C. for 3 h, cooled to RT and then filtered. The filtrate was diluted with EA (90 mL), washed with 2M HCl (40 mL×3), water (40 mL) and brine (40 mL). The organic phase was dried over MgSO$_4$, filtered and evaporated to give 5-chloro-6,7-difluoro-1H-indole-2-carboxylic acid (880 mg, crude, 100% yield) as a dark solid. $^1$H NMR (400 MHz, DMSO-d$_6$): δ 12.69 (brs, 1H), 7.73 (d, J=1.2 Hz, 1H), 7.16 (s, 1H).

Step 3:

To a solution of 5-chloro-6,7-difluoro-1H-indole-2-carboxylic acid (880 mg, 3.8 mmol) in DMF (10 mL) was added triethylamine (771 mg, 7.6 mmol), HATU (2.9 g, 7.6 mmol) and (R)-3-(Boc-amino)pyrrolidine (1.1 g, 5.7 mmol). The mixture was stirred at RT for 4 h. The reaction mixture was then diluted with water (50 mL) and extracted with EA (30 mL×3). The combined organic phases were dried over Na$_2$SO$_4$, filtered and concentrated. The crude product was purified by silica gel chromatography (PE/EA=1:1) to give tert-butyl (R)-(1-(5-chloro-6,7-difluoro-1H-indole-2-carbonyl)pyrrolidin-3-yl)carbamate (320 mg, 21% yield) as a dark oil. $^1$H NMR (400 MHz, DMSO-d$_6$): δ 12.47 (s, 1H), 7.71 (d, J=2.0 Hz, 1H), 7.23 (br s, 1H), 7.01 (d, J=1.2 Hz, 1H), 4.17-4.04 (m, 1H), 4.01-3.93 (m, 1H), 3.92-3.79 (m, 1H), 3.73-3.63 (m, 1H), 3.62-3.50 (m, 1H), 2.18-2.01 (m, 1H), 1.93-1.77 (m, 1H), 1.41 (s, 9H).

Step 4:

To a solution of tert-butyl (R)-(1-(5-chloro-6,7-difluoro-1H-indole-2-carbonyl)pyrrolidin-3-yl)carbamate (320 mg, 0.8 mmol) in DCM (5 mL) was added trifluoroacetic acid (5 mL). The mixture was stirred at RT for 1 h and then concentrated. The residue was purified by prep-HPLC (CH$_3$CN/H$_2$O/(0.1%) NH$_3$.H$_2$O) to give (R)-(3-aminopyrrolidin-1-yl)(5-chloro-6,7-difluoro-1H-indol-2-yl)methanone (100 mg, 42% yield) as a white solid. $^1$H NMR (400 MHz, CDCl$_3$): δ 9.92 (br s, 1H), 7.44 (d, J=5.6 Hz, 1H), 6.81 (d, J=2.8 Hz, 1H), 4.06 (m, 1H), 3.97-3.74 (m, 3H), 3.59-3.50 (m, 1H), 2.28-2.15 (m, 1H), 1.98-1.75 (m, 1H). MS Calcd.: 299 MS Found: 300 ([M+H]$^+$).

Example 2: Synthesis of (R)-(3-Aminopyrrolidin-1-yl)(5-chloro-7-fluoro-1H-indol-2-yl)methanone

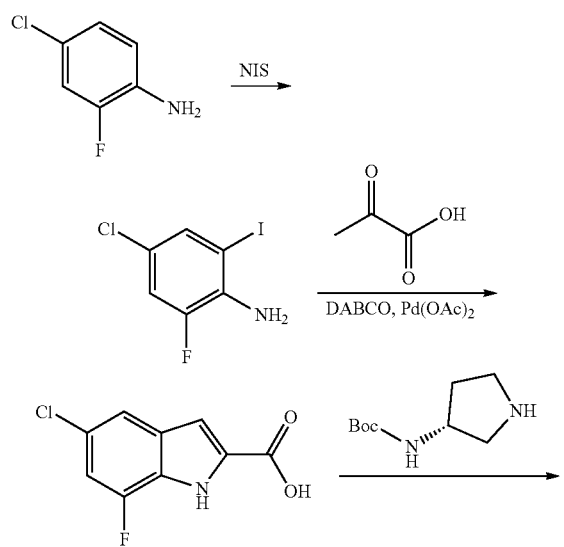

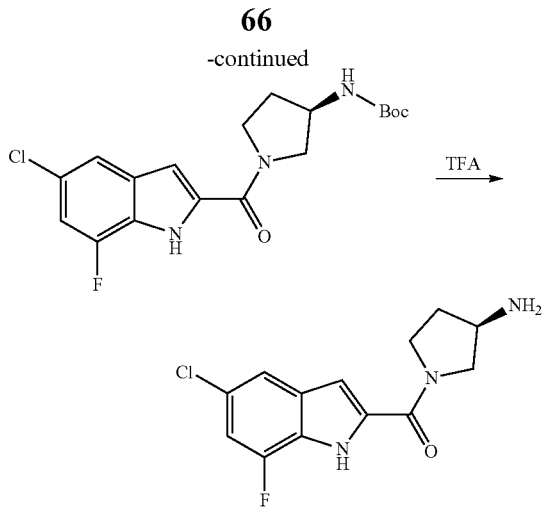

Step 1:

To a solution of 4-chloro-2-fluoroaniline (2 g, 14 mmol) in EtOH (40 mL) was added Ag$_2$SO$_4$ (12.9 g, 42 mmol), followed by the addition of I$_2$ (10.5 g, 42 mmol). The reaction mixture was stirred at RT for 2 h and then filtered through Celite. The filtrate was evaporated to give a dark oil. The residue was dissolved in DCM (70 mL), washed with 2M NaOH (40 mL×2), Na$_2$S$_2$O$_3$ (40 mL×2) and water (40 mL×2). The resulting solution was dried over MgSO$_4$, filtered and concentrated. The residue was purified by column chromatography on silica gel (PE/EA=5/1) to give 4-chloro-2-fluoro-6-iodoaniline (1.5 g, 40% yield) as a dark oil. $^1$H NMR (400 MHz, DMSO-d$_6$): δ 7.47-7.46 (m, 1H), 7.28-7.25 (m, 1H), 5.31 (brs, 2H).

Step 2:

4-Chloro-2-fluoro-6-iodoaniline (2.5 g, 9.2 mmol), pyruvic acid (2.5 g, 27 mmol) and DABCO (3.1 g, 27 mmol) were dissolved in DMF (15 mL). The solution was degassed and palladium acetate (500 mg) was added. The reaction mixture was heated at 100° C. for 3 h, cooled to RT and then filtered. The filtrate was diluted with EA (90 mL), washed with 2M HCl (20 mL×3), water (40 mL) and brine (40 mL). The organic phase was dried over MgSO$_4$, filtered and evaporated to give 5-chloro-7-fluoro-1H-indole-2-carboxylic acid (1.9 g, 97% yield) as a dark solid. $^1$H NMR (400 MHz, DMSO-d$_6$): δ 13.06 (br s, 1H), 12.50 (s, 1H), 7.59 (s, 1H), 7.21 (d, J=1.2 Hz, 1H), 7.16-7.15 (t, J=3.2 Hz, 1H).

Step 3:

To a solution of 5-chloro-7-fluoro-1H-indole-2-carboxylic acid (500 mg, 2.35 mmol) in DMF (10 mL) was added triethylamine (478 mg, 5 mmol), HATU (1.8 g, 5 mmol) and (R)-3-(Boc-amino)pyrrolidine (659 mg, 3.8 mmol). The mixture was stirred at RT for 4 h. The reaction mixture was then diluted with water (50 mL) and extracted with EA (30 mL×3). The combined organic phases were dried over Na$_2$SO$_4$, filtered and concentrated. The crude product was purified by silica gel chromatography (PE/EA=1:1) to give tert-butyl (R)-(1-(5-chloro-7-fluoro-1H-indole-2-carbonyl)pyrrolidin-3-yl)carbamate (475 mg, 53% yield) as a yellow solid. H NMR (400 MHz, DMSO-d$_6$): δ 12.25 (s, 1H), 7.56 (s, 1H), 7.25 (brs, 1H), 7.17 (dd, J=1.6, 1.2 Hz, 1H), 6.701-6.96 (m, 1H), 4.14-4.02 (m, 1H), 4.01-3.93 (m, 1H), 3.92-3.78 (m, 1H), 3.74-3.63 (m, 1H), 3.62-3.53 (m, 1H), 2.20-2.01 (m, 1H), 1.94-1.83 (m, 1H), 1.39 (s, 9H).

Step 4:

To a solution of tert-butyl (R)-(1-(5-chloro-7-fluoro-1H-indole-2-carbonyl)pyrrolidin-3-yl)carbamate (500 mg, 1.3 mmol) in DCM (5 mL) was added trifluoroacetic acid (5 mL). The mixture was stirred at RT for 1 h and then concentrated. The residue was purified by prep-HPLC (CH$_3$CN/H$_2$O/(0.1%) NH$_3$·H$_2$O) to give (R)-(3-aminopyrrolidin-1-yl)(5-chloro-7-fluoro-1H-indol-2-yl)methanone (100 mg, 27% yield) as a white solid. $^1$H NMR (400 MHz, CDCl$_3$): δ 9.75 (br s, 1H), 7.43 (s, 1H), 7.03-7.00 (dd, J=1.2, 1.2 Hz, 1H), 6.83-6.81 (d, J=10.0 Hz, 1H), 4.12-4.03 (m, 1H), 3.98-3.73 (m, 3H), 3.61-3.49 (m, 1H), 2.28-2.13 (m, 1H), 1.98-1.73 (m, 1H). MS Calcd.: 281 MS Found: 282 ([M+H]$^+$).

Example 3: Synthesis of (R)-(3-Aminopyrrolidin-1-yl)(5,6,7-trifluoro-1H-indol-2-yl)methanone

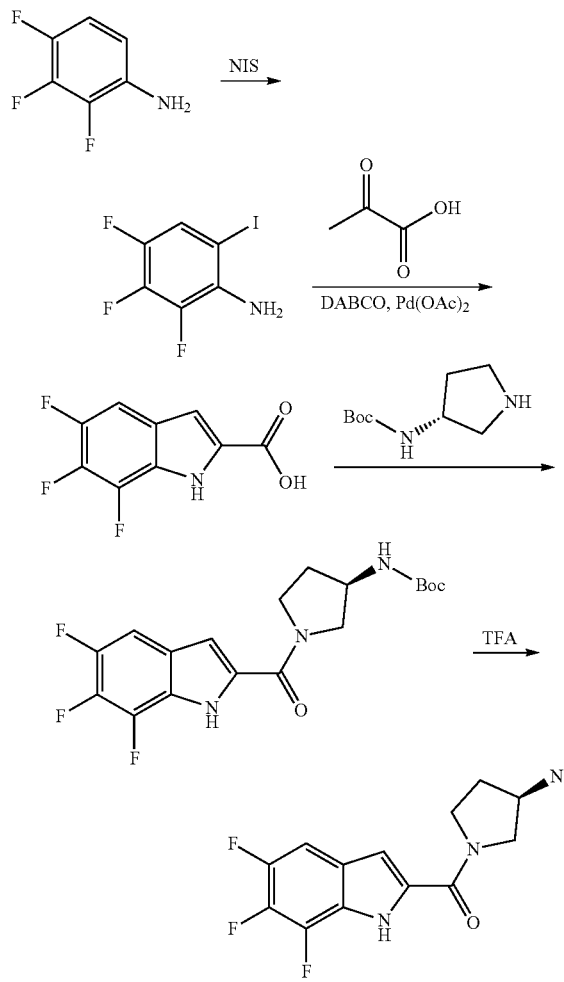

Step 1:
To a solution of 2,3,4-trifluoroaniline (2 g, 13.6 mmol) in DMF (15 mL) was added NIS (3.7 g, 16 mmol) and the mixture was stirred at RT for 3 h. The reaction mixture was diluted with water (50 mL) and extracted with EA (30 mL×3). The combined organic phases were dried over Na$_2$SO$_4$, filtered and concentrated. The crude product was purified by silica gel chromatography (PE/EA=10:1) to give 2,3,4-trifluoro-6-iodoaniline as a black solid (1.4 g, 38% yield). $^1$H NMR (DMSO-d$_6$, 400 MHz): δ 7.63-7.40 (d, J=2.0 Hz, 1H), 5.27-5.22 (m, 2H).

Step 2:
To a solution of 2,3,4-trifluoro-6-iodoaniline (400 mg, 1.5 mmol) in DMF (20 mL) was added pyruvic acid (262 mg, 3.0 mmol), DABCO (333 mg, 3.0 mmol). The solution was degassed and palladium acetate (150 mg) was added. The reaction mixture was heated at 100° C. for 3 h, cooled to RT and then filtered. The filtrate was diluted with EA (150 mL), washed with 2M HCl (30 mL×3), water (40 mL) and brine (40 mL). The organic phase was dried over MgSO$_4$, filtered and evaporated to give 5,6,7-trifluoro-1H-indole-2-carboxylic acid (200 mg, 62% yield) as a dark solid. $^1$H NMR (DMSO-d$_6$, 400 MHz): δ 12.56 (brs, 1H), 7.58-7.52 (m, 1H), 7.17 (m, 1H).

Step 3:
To a solution of 5,6,7-trifluoro-1H-indole-2-carboxylic acid (400 mg, 1.9 mmol) in DMF (20 mL) was added triethylamine (425 mg, 4 mmol), HATU (1.4 g, 4 mmol) and (R)-3-(Boc-amino)pyrrolidine (525 mg, 3 mmol). The mixture was stirred at RT for 4 h. The reaction mixture was diluted with water (50 mL) and extracted with EA (30 mL×3). The combined organic phases were dried over Na$_2$SO$_4$, filtered and concentrated. The crude product was purified by silica gel chromatography (PE/EA=1:1) to give tert-butyl (R)-(1-(5,6,7-trifluoro-1H-indole-2-carbonyl)pyrrolidin-3-yl)carbamate (0.4 g, 55% yield) as a brown oil. $^1$H NMR (DMSO-d$_6$, 400 MHz): δ 12.38 (br s, 1H), 7.55-7.50 (m, 1H), 7.04-6.99 (m, 1H), 4.10-4.08 (m, 1H), 3.96-3.81 (m, 1H), 3.70-3.55 (m, 2H), 3.44-3.41 (m, 1H), 1.41 (s, 9H).

Step 4:
To a solution of tert-butyl (R)-(1-(5,6,7-trifluoro-1H-indole-2-carbonyl)pyrrolidin-3-yl)carbamate (400 mg, 1.04 mmol) in DCM (4 mL) was added TFA (4 mL). The mixture was stirred at RT for 1 h. The reaction mixture was concentrated, and the residue was purified by prep-HPLC (CH$_3$CN/H$_2$O/(0.1%) NH$_3$·H$_2$O) to give (R)-(3-aminopyrrolidin-1-yl)(5,6,7-trifluoro-1H-indol-2-yl)methanone (160 mg, 54% yield) as white solid. $^1$H NMR (CDCl$_3$, 400 MHz): δ 7.36-7.31 (m, 1H), 7.05-7.01 (m, 1H), 4.08-4.03 (m, 1H), 3.92-3.80 (m, 1H), 3.71-3.56 (m, 2H), 3.47-3.13 (m, 1H), 2.25-2.15 (m, 1H), 1.94-1.71 (m, 1H). MS Calcd: 283 MS Found: 284 ([M+H]$^+$).

Example 4: Synthesis of (R)-(3-Aminopyrrolidin-1-yl)(6-chloro-5,7-difluoro-1H-indol-2-yl)methanone

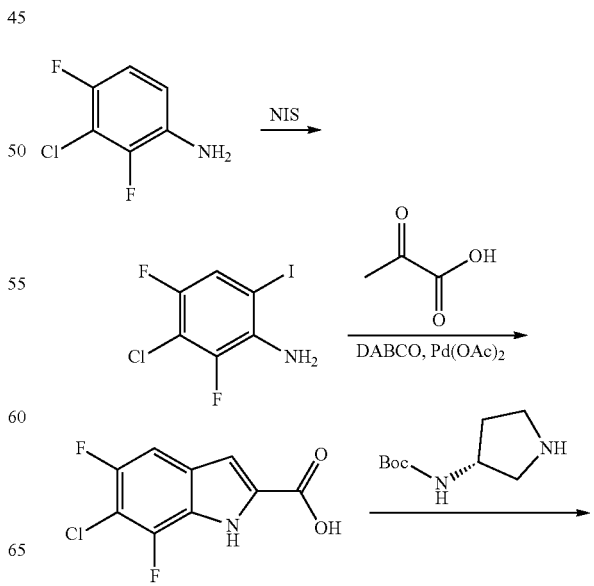

-continued

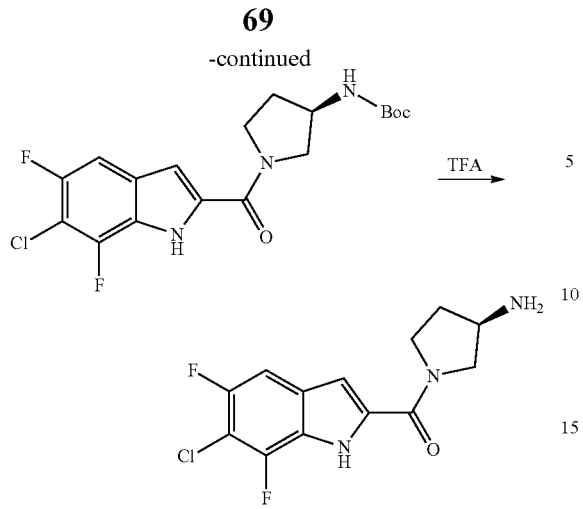

Step 1:
To a solution of 3-chloro-2,4-difluoroaniline (1 g, 6.1 mmol) in DMF (20 mL) was added NIS (1.7 g, 7 mmol) at RT. The mixture was stirred at RT for 3 h. The reaction mixture was diluted with water (20 mL) and extracted with EA (10 mL×3). The combined organic phases were dried over Na$_2$SO$_4$, filtered and concentrated. The crude product was purified by silica gel chromatography (PE/EA=10:1) to give 3-chloro-2,4-difluoro-6-iodoaniline (1.1 g, 62% yield) as a yellow oil. $^1$H NMR (CDCl3, 400 MHz): δ 7.09-7.09 (m, 1H).

Step 2:
To a solution of 3-chloro-2,4-difluoro-6-iodoaniline (0.4 g, 1.4 mmol) in DMF (20 mL) was added pyruvic acid (0.26 g, 2.9 mmol), DABCO (0.30 g, 2.9 mmol) and palladium acetate (150 mg). The solution was degassed and heated at 100° C. for 3 h. The mixture was then cooled and filtered. The filtrate was diluted with EA (150 mL), washed with 2M HCl (30 mL×3), water (40 mL) and brine (40 mL). The solution was dried over Na$_2$SO$_4$, filtered and evaporated to give 6-chloro-5,7-difluoro-1H-indole-2-carboxylic acid (0.3 g, 93% yield) as a dark solid. $^1$H NMR (DMSO-d$_6$, 400 MHz): δ12.63 (s, 1H), 7.63-7.60 (d, J=9.6, Hz, 1H), 5.67 (s, 1H).

Step 3:
To a solution of 6-chloro-5,7-difluoro-1H-indole-2-carboxylic acid (400 mg, 1.7 mmol) in DMF was added triethylamine (344 mg, 3 mmol), HATU (1.29 g, 3 mmol) and (R)-3-(Boc-amino)pyrrolidine (484 mg, 3 mmol). The mixture was stirred at RT for 4 h. The reaction mixture was diluted with water (50 mL) and extracted with EA (30 mL×3). The combined organic phases were dried over Na$_2$SO$_4$, filtered and concentrated. The crude product was purified by silica gel chromatography (PE/EA=1:1) to give tert-butyl (R)-(1-(6-chloro-5,7-difluoro-1H-indole-2-carbonyl)pyrrolidin-3-yl)carbamate as a black solid (450 mg, 66% yield). $^1$H NMR (CDCl$_3$, 400 MHz): δ 12.38 (brs, 1H), 7.55-7.53 (d, J=8.0 Hz, 1H), 7.06-7.01 (m, 1H), 4.11-3.98 (m, 1H), 3.94-3.80 (m, 1H), 3.72-3.53 (m, 2H), 3.45-3.42 (m, 1H), 1.41 (s, 9H).

Step 4:
To a solution of tert-butyl (R)-(1-(6-chloro-5,7-difluoro-1H-indole-2-carbonyl)pyrrolidin-3-yl)carbamate (200 mg, 0.5 mmol) in DCM (4 mL) was added TFA (4 mL). The mixture was stirred at RT for 1 h. The reaction mixture was concentrated, and the residue was purified by prep-HPLC (CH$_3$CN/H$_2$O/(0.1%) NH$_3$.H$_2$O) to give (R)-(3-aminopyrrolidin-1-yl)(6-chloro-5,7-difluoro-1H-indol-2-yl)methanone (94 mg, 62% yield) as white solid. $^1$H NMR (CDCl$_3$, 400 MHz): δ 10.06-10.11 (brs, 1H), 7.27-7.20 (d, J=2.8 Hz, 1H), 6.85-6.82 (m, 1H), 4.08-4.04 (m, 1H), 4.07-4.03 (m, 3H), 3.60-3.52 (m, 1H), 2.26-2.16 (m, 1H), 1.94-1.83 (m, 1H). MS Calcd: 283 MS Found: 300 ([M+H]$^+$).

Example 5: Synthesis of (R)-(3-Aminopyrrolidin-1-yl)(5-bromo-6,7-difluoro-1H-indol-2-yl)methanone

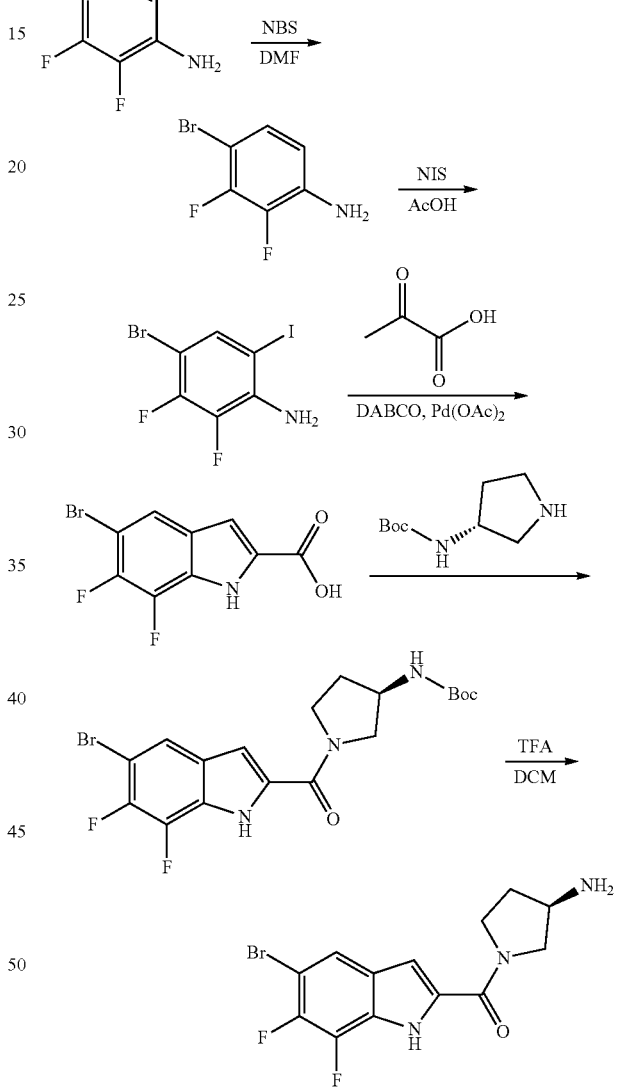

Step 1:
To a solution of 2,3-difluoroaniline (4 g, 31 mmol) in DMF (20 mL) was added NBS (5.5 g, 31 mmol). The mixture was stirred at 0° C. for 1 h. The reaction solution was diluted with water (20 mL) and extracted with EA (30 mL×3). The combined organics were concentrated to give 4-bromo-2,3-difluoroaniline as red oil (6.3 g, 97% yield).

Step 2:
To a solution of 4-bromo-2,3-difluoroaniline (3 g, 14.4 mmol) in AcOH (20 mL) was added NIS (3.3 g, 14.4 mmol). The mixture was stirred at RT for 2 h. The reaction was diluted with saturated sodium carbonate aqueous solution (20 mL) and extracted with EA (30 mL×3). The organics were concentrated to give 4-bromo-2,3-difluoro-6-iodoaniline as a red oil (4.8 g, 94% yield). ¹H NMR (CDCl₃, 400 MHz): δ 7.58 (dd, J=6.4 Hz, 2.4 Hz, 1H), 4.27 (s, 2H).

Step 3:

To a solution of 4-bromo-2,3-difluoro-6-iodoaniline (4.8 g, 14.4 mmol) in DMF (20 mL) was added pyruvic acid (2.6 g, 29 mmol), DABCO (3.2 g, 29 mmol) and Pd(OAc)₂ (300 mg). The mixture reaction was degassed with nitrogen and stirred at 105° C. for 4 h. The mixture solution was filtered through Celite and the filtrate was extracted with EA (40 mL×3). The combined organics were concentrated to give 5-bromo-6,7-difluoro-1H-indole-2-carboxylic acid (502 mg, 13% yield) as a brown solid. MS Calcd.: 275; MS Found: 276 (M+H)⁺.

Step 4:

To a solution of 5-bromo-6,7-difluoro-1H-indole-2-carboxylic acid (2 g, 7.2 mmol) in DMF (15 mL) was added Et₃N (2.7 g, 14.5 mmol), HATU (5.5 g, 14.5 mmol) and (R)-3-(Boc-amino)pyrrolidine (2.7 g, 14.5 mmol). The mixture was stirred at RT for 1 h. The reaction mixture was diluted with water (20 mL) and extracted with EA (30 mL×3). The combined organic phases were dried over Na₂SO₄, filtered and concentrated. The crude product was purified by silica gel chromatography (PE/EA=2:1) to give tert-butyl (R)-(1-(5-bromo-6,7-difluoro-1H-indole-2-carbonyl)pyrrolidin-3-yl)carbamate (400 mg, 13% yield) as yellow solid. MS Calcd.: 443; MS Found: 444 (M+H)⁺.

Step 5:

To a solution of tert-butyl (R)-(1-(5-bromo-6,7-difluoro-1H-indole-2-carbonyl)pyrrolidin-3-yl)carbamate (400 mg, 0.9 mmol) in DCM (5 mL) was added TFA (5 mL). The mixture was stirred at RT for 1 h. The solution was diluted with saturated sodium carbonate aqueous solution (20 mL), and extracted with EA (50 mL×3). The combined organics were dried with Na₂SO₄, filtered and concentrated. The crude product was further purified by prep-HPLC to give (R)-(3-aminopyrrolidin-1-yl)(5-bromo-6,7-difluoro-1H-indol-2-yl)methanone (56 mg, 18% yield) as a white solid (TFA salt). ¹H NMR (CDCl₃, 400 MHz): δ10.31-10.23 (m, 1H), 7.58 (d, J=5.6 Hz, 1H), 6.79 (s, 1H), 4.08-4.02 (m, 1H), 3.9-3.75 (m, 3H), 3.58-3.54 (m, 1H), 2.28-2.15 (m, 1H), 1.97-1.75 (m, 1H). MS Calcd.: 343; MS Found: 344 (M+H)⁺.

Example 6: Synthesis of (R)-(3-Aminopyrrolidin-1-yl)(6-bromo-5,7-difluoro-1H-indol-2-yl)methanone

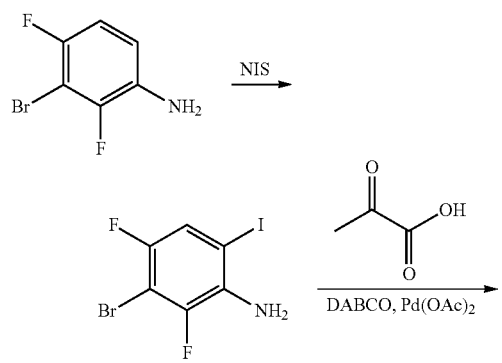

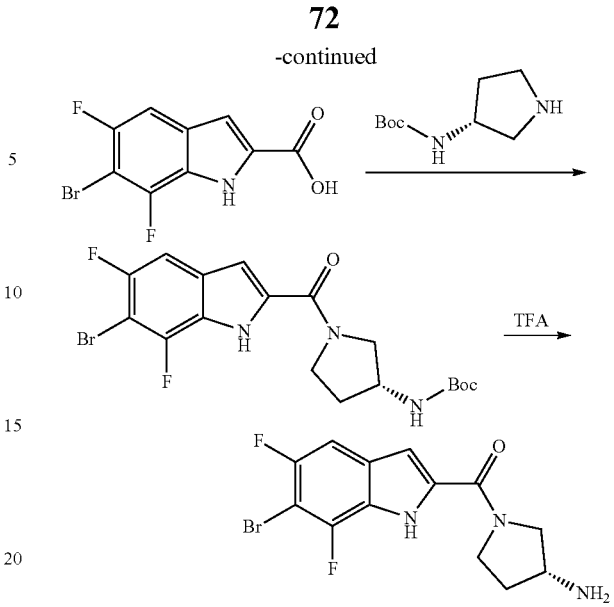

Step 1:

To a solution of 3-bromo-2,4-difluoroaniline (1 g, 4.8 mmol) in DMF (20 mL) was added NIS (1.6 g, 7 mmol) and the mixture was stirred at RT for 3 h. The reaction mixture was diluted with water (20 mL) and extracted with EA (10 mL×3). The combined organics were dried over Na₂SO₄, filtered and concentrated. The crude product was purified by silica gel chromatography (PE/EA=10:1) to give 3-bromo-2,4-difluoro-6-iodoaniline (600 mg, 38% yield) as a black oil.

Step 2:

To a solution of 3-bromo-2,4-difluoro-6-iodoaniline (450 mg, 1.3 mmol) in DMF (20 mL) was added pyruvic acid (237 mg, 2.6 mmol), DABCO (292 mg, 2.8 mmol) and palladium acetate (150 mg) at RT. The solution was degassed and heated at 100° C. for 3 h. The mixture was cooled to RT and filtered. The filtrate was diluted with EA (150 mL), washed with 2M HCl (30 mL×3), water (40 mL) and brine (40 mL). The separated organic phase was dried over MgSO₄ and concentrated to give 6-bromo-5,7-difluoro-1H-indole-2-carboxylic acid (250 mg, 70% yield) as a dark solid.

Step 3:

To a solution of 6-bromo-5,7-difluoro-1H-indole-2-carboxylic acid (250 mg, 0.91 mmol) in DMF was added triethylamine (182 mg, 1.8 mmol), HATU (513 mg, 1.4 mmol) and (R)-3-(Boc-amino)pyrrolidine (332 mg, 1.8 mmol). The mixture was stirred at RT for 4 h. The reaction mixture was diluted with water (50 mL), extracted with EA (30 mL×3). The combined organic phases were dried over Na₂SO₄, filtered and concentrated. The crude product was purified by silica gel chromatography (PE/EA=1:1) to give tert-butyl (R)-(1-(6-bromo-5,7-difluoro-1H-indole-2-carbonyl)pyrrolidin-3-yl)carbamate as a yellow solid (240 mg, 60% yield). ¹H NMR (CDCl₃, 400 MHz): δ 9.82-9.84 (brs, 1H), 7.20-7.22 (d, J=8.0 Hz, 1H), 6.85 (s, 1H), 4.12-4.16 (m, 2H), 3.67-3.85 (m, 3H), 2.08-2.39 (m, 1H), 1.91-1.93 (m, 1H), 1.41 (s, 9H).

Step 4:

To a solution of tert-butyl (R)-(1-(6-bromo-5,7-difluoro-1H-indole-2-carbonyl)pyrrolidin-3-yl)carbamate (100 mg, 0.22 mmol) in DCM (4 mL) was added TFA (4 mL). The mixture was stirred at RT for 1 h. The reaction mixture was concentrated and the residue was purified by prep-HPLC (CH₃CN/H₂O/(0.1%)NH₃.H₂O) to give (R)-(3-aminopyrrolidin-1-yl)(6-bromo-5,7-difluoro-1H-indol-2-yl)methanone (20 mg, 26% yield) as a white solid. H NMR (CDCl₃, 400 MHz): δ 9.54-9.89 (brs, 1H), 7.20-7.22 (m, 1H), 6.84-6.87 (m, 1H), 4.04-4.08 (m, 1H), 3.76-3.96 (m, 3H), 3.50-3.51 (m, 1H), 2.17-2.26 (m, 1H), 1.67-1.97 (m, 1H). MS Calcd.: 343; MS Found: 345 (M+H)⁺.

Example 7: Synthesis of ((3S,4R)-3-Amino-4-fluoro-pyrrolidin-1-yl)-(5-chloro-6,7-difluoro-1H-indol-2-yl)-methanone

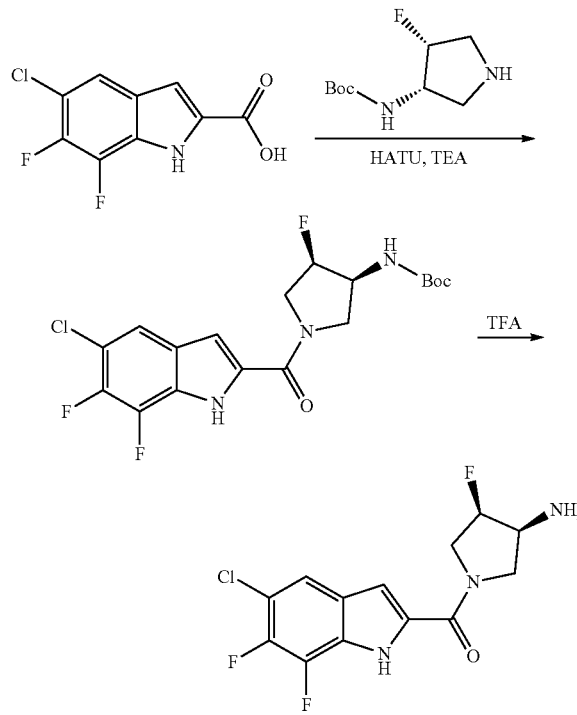

Step 1:
To a solution of 5-chloro-6,7-difluoro-1H-indole-2-carboxylic acid (200 mg, 0.87 mmol) in DMF (8 mL) was added TEA (176 mg, 1.74 mmol), HATU (395 mg, 1.04 mmol) and tert-butyl ((3S,4R)-4-fluoropyrrolidin-3-yl)carbamate (195 mg, 0.96 mmol). The reaction mixture was stirred at RT for 4 h. The mixture was diluted with water (20 mL) and extracted with EA (20 mL×3). The combined organics were dried over Na₂SO₄, filtered and concentrated. The crude product was purified by silica gel chromatography (PE/EA=1/1) to give tert-butyl ((3S,4R)-1-(5-chloro-6,7-difluoro-1H-indole-2-carbonyl)-4-fluoropyrrolidin-3-yl)carbamate (70 mg, 19% yield) as a white solid. H NMR (400 MHz, DMSO-d₆): δ 12.55 (d, J=9.6 Hz, 1H), 7.74-7.69 (m, 1H), 7.36-7.31 (m, 1H), 7.02-7.01 (m, 1H), 5.20 (m, 1H), 4.42-4.25 (m, 1H), 4.23-4.09 (m, 1H), 4.07-3.89 (m, 1H), 3.87-3.70 (m, 1H), 3.69-3.40 (m, 1H), 1.40 (s, 9H). MS Calcd: 231; MS Found: 232 ([M+H]⁺).

Step 2:
To a solution of tert-butyl ((3S,4R)-1-(5-chloro-6,7-difluoro-1H-indole-2-carbonyl)-4-fluoropyrrolidin-3-yl)carbamate (70 mg, 0.17 mmol) in DCM (5 mL) was added TFA (5 mL). The reaction mixture was stirred at RT for 1 h and then concentrated. The residue was triturated in a mixture of PE/EA=5:1 (30 mL), and the solids were filtered, dried in vacuo to give ((3S,4R)-3-amino-4-fluoropyrrolidin-1-yl)(5-chloro-6,7-difluoro-1H-indol-2-yl)methanone (59 mg, 82% yield) as a white solid (TFA salt). ¹H NMR (400 MHz, DMSO-d₆): δ 12.63 (d, J=22 Hz, 1H), 8.65 (s, 2H), 7.78-7.72 (m, 1H), 7.03 (d, J=20.8 Hz, 1H), 5.50 (m, 1H), 4.31-4.21 (m, 1H), 4.18-4.02 (m, 2H), 3.98-3.81 (m, 1H), 3.64-3.53 (m, 1H); MS Calcd: 317, MS Found: 318 ([M+H]⁺).

Example 8: Synthesis of (R)-(3-Aminopyrrolidin-1-yl)(5-chloro-1H-indol-2-yl)methanone

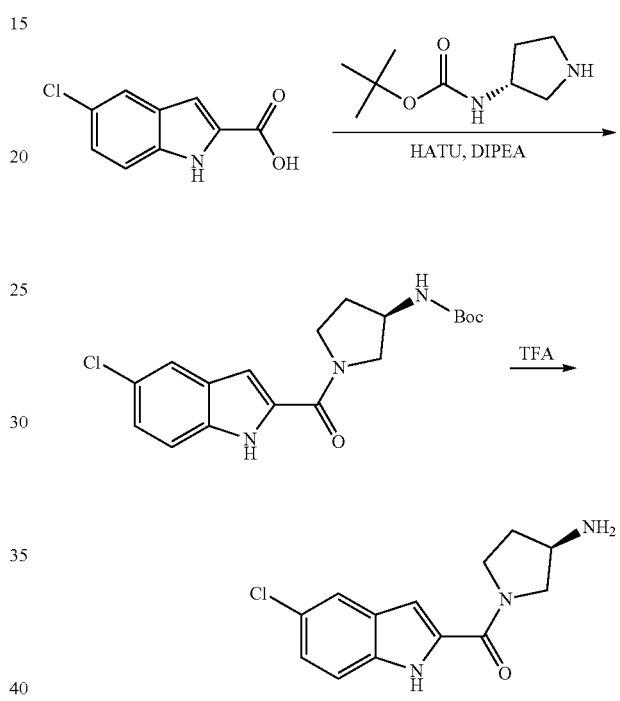

Step 1:
To a mixture of 5-chloro-1H-indole-2-carboxylic acid (196 mg, 1 mmol), (R)-3-(Boc-amino)pyrrolidine (204 mg, 1.1 mmol) and HATU (456 mg, 1.2 mmol) in DMF (3 mL) was added N,N-diisopropylethylamine (0.29 mL, 1.2 mmol). The reaction mixture was stirred at RT for 3 h, quenched with water and extracted with EtOAc (5 mL, 3x). The extracts were washed with saturated sodium bicarbonate, 0.1 M aqueous HCl solution, brine, dried (Na₂SO₄), filtered and concentrated. The residue was purified by silica gel chromatography (EA/Hexanes, 0-100%) to give 287 mg (79%) of tert-butyl (R)-(1-(5-chloro-1H-indole-2-carbonyl)pyrrolidin-3-yl)carbamate. MS Calcd: 363, MS Found: 364 ([M+H]⁺).

Step 2:
To a solution of tert-butyl (R)-(1-(5-chloro-1H-indole-2-carbonyl)pyrrolidin-3-yl)carbamate (287 mg, 0.79 mmol) in DCM (5 mL) was added TFA (5 mL). The reaction mixture was stirred at RT for 1 h and then concentrated. The residue was triturated in a mixture of PE/EA=5:1 (30 mL), and the solids were filtered, dried in vacuo to give 253 mg (99%) of (R)-(3-aminopyrrolidin-1-yl)-(5-chloro-1H-indol-2-yl)methanone as a TFA salt. MS Calcd: 263, MS Found: 264 ([M+H]⁺).

Example 9: Synthesis of (S)—N-(1-Aminopropan-2-yl)-5-chloro-6,7-difluoro-1H-indole-2-carboxamide

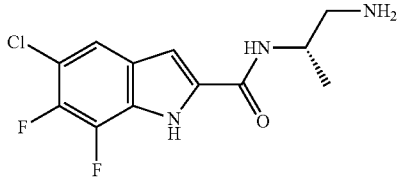 [SMILES: C[C@@H](CN)NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.52 (s, 1H), 8.49 (d, J=8.0 Hz, 1H), 7.91 (s, 2H), 7.78 (d, J=6.4 Hz, 1H), 7.22 (d, J=2.4 Hz, 1H), 4.29-4.26 (m, 1H), 2.97-2.94 (m, 2H), 1.23-1.21 (m, 3H). MS Calcd: 287, MS Found: 288 ([M+H]$^+$).

Example 10: Synthesis of (S)—N-(1-Aminobutan-2-yl)-5-chloro-6,7-difluoro-1H-indole-2-carboxamide

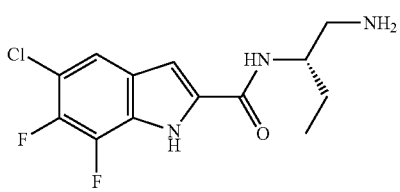 [SMILES: CC[C@@H](CN)NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.52 (s, 1H), 8.40 (d, J=8.8 Hz, 1H), 7.86 (brs, 3H), 7.79 (d, J=5.6 Hz, 1H), 7.21 (s, 1H), 4.14-4.10 (m, 1H), 3.03-2.88 (m, 2H), 1.65-1.48 (m, 2H), 0.89 (t, J=7.2 Hz, 3H). MS Calcd: 301, MS Found: 302 ([M+H]$^+$).

Example 11: Synthesis of N-(2-Amino-1-cyclopropylethyl)-5-chloro-6,7-difluoro-1H-indole-2-carboxamide

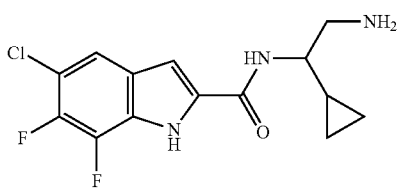 [SMILES: NCC(NC(=O)c1cc2cc(Cl)c(F)c(F)c2[nH]1)C1CC1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.52 (s, 1H), 8.56 (d, J=8.4 Hz, 1H), 7.90 (s, 2H), 7.79 (d, J=5.6 Hz, 1H), 7.23 (s, 1H), 3.66-3.62 (m, 1H), 3.10-3.06 (m, 2H), 1.04-1.02 (m, 1H), 0.56-0.45 (m, 2H), 0.37-0.30 (m, 2H). MS Calcd: 313, MS Found: 314 ([M+H]$^+$).

Example 12: Synthesis of N-(3-(Aminomethyl)oxetan-3-yl)-5-chloro-6,7-difluoro-1H-indole-2-carboxamide

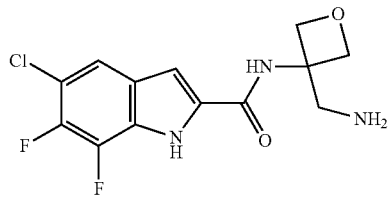 [SMILES: NCC1(NC(=O)c2cc3cc(Cl)c(F)c(F)c3[nH]2)COC1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.74 (s, 1H), 7.92 (s, 2H), 7.72 (d, J=6.0 Hz, 1H), 7.07 (d, J=2.8 Hz, 1H), 5.33 (brs, 1H), 4.45-4.38 (m, 2H), 3.60-3.46 (m, 2H), 3.13 (s, 2H). MS Calcd: 315, MS Found: 316 ([M+H]$^+$).

Example 13: Synthesis of 5-Chloro-6,7-difluoro-N-((3S,4R)-4-methylpyrrolidin-3-yl)-1H-indole-2-carboxamide

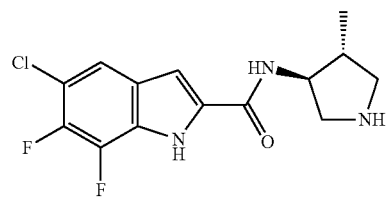 [SMILES: C[C@@H]1CNC[C@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.55 (s, 1H), 9.02-8.98 (m, 1H), 8.73 (d, J=7.6 Hz, 1H), 7.78 (d, J=6.0 Hz, 1H), 7.25 (s, 1H), 4.20-4.16 (m, 1H), 3.55-3.39 (m, 2H), 3.06-3.05 (m, 1H), 2.91-2.86 (m, 1H), 2.35-2.31 (m, 1H), 1.09 (d, J=7.2 Hz, 3H). MS Calcd: 313, MS Found: 314 ([M+H]$^+$).

Example 14: Synthesis of 5-Chloro-6,7-difluoro-N-((3S,4S)-4-methylpyrrolidin-3-yl)-1H-indole-2-carboxamide

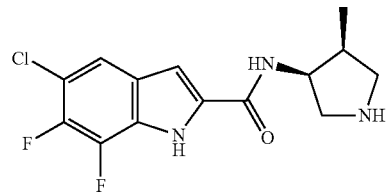 [SMILES: C[C@H]1CNC[C@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.58 (s, 1H), 9.02 (brs, 1H), 8.56 (d, J=8.0 Hz, 1H), 7.76 (d, J=5.6 Hz, 1H), 7.27 (s, 1H), 4.65-4.72 (m, 1H), 3.59-3.55 (m, 2H), 3.44-3.24 (m, 2H), 3.03-2.98 (m, 1H), 0.94 (d, J=6.8 Hz, 3H). MS Calcd: 313, MS Found: 314 ([M+H]⁺).

Example 15: Synthesis of 5-Chloro-6,7-difluoro-N-((3R,4R)-4-hydroxypyrrolidin-3-yl)-1H-indole-2-carboxamide

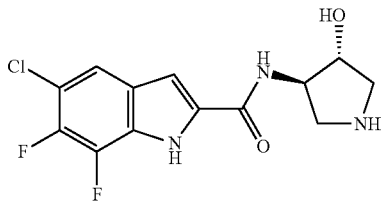 [SMILES: O=C(N[C@@H]1CNC[C@H]1O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.58 (s, 1H), 9.02 (s, 1H), 8.60 (d, J=6.0 Hz, 1H), 7.79 (d, J=5.8 Hz, 1H), 7.21 (s, 1H), 5.90 (d, J=2.4 Hz, 1H), 4.32 (s, 2H), 3.61-3.57 (m, 1H), 3.45-3.41 (m, 1H), 3.29-3.26 (m, 1H), 3.15 (d, J=11.6 Hz, 1H). MS Calcd: 315, MS Found: 316 ([M+H]⁺).

Example 16: Synthesis of 5-Chloro-6,7-difluoro-N-((3R,4S)-4-hydroxypyrrolidin-3-yl)-1H-indole-2-carboxamide

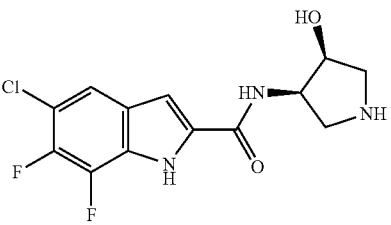 [SMILES: O=C(N[C@@H]1CNC[C@@H]1O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.58 (s, 1H), 9.26 (s, 1H), 8.91 (s, 1H), 8.50 (d, J=7.6 Hz, 1H), 7.79 (d, J=5.2 Hz, 1H), 7.31 (s, 1H), 5.84 (s, 1H), 4.51-3.4.55 (m, 1H), 4.32 (s, 1H), 3.48-3.44 (m, 2H), 3.26-3.18 (m, 2H). MS Calcd: 315, MS Found: 316 ([M+H]⁺).

Example 17: Synthesis of 5-Chloro-6,7-difluoro-N-((3S,4R)-4-hydroxypyrrolidin-3-yl)-1H-indole-2-carboxamide

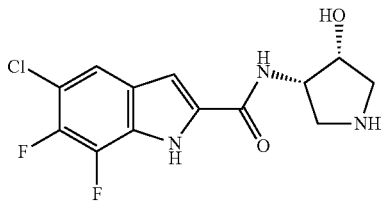 [SMILES: O=C(N[C@H]1CNC[C@H]1O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.58 (s, 1H), 9.20 (brs, 1H), 8.51 (d, J=7.6 Hz, 1H), 7.79 (d, J=5.6 Hz, 1H), 7.31 (s, 1H), 5.84 (s, 1H), 4.56-4.49 (m, 1H), 4.32 (s, 1H), 3.49-3.39 (m, 2H), 3.26-3.19 (m, 2H). MS Calcd: 315, MS Found: 316 ([M+H]⁺).

Example 18: Synthesis of 5-Chloro-6,7-difluoro-N-((3S,4S)-4-hydroxypyrrolidin-3-yl)-1H-indole-2-carboxamide

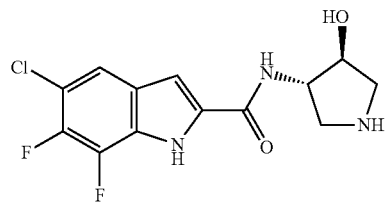 [SMILES: O=C(N[C@H]1CNC[C@@H]1O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.58 (s, 1H), 9.19-9.12 (m, 2H), 8.68 (d, J=6.0 Hz, 1H), 7.78 (d, J=6.0 Hz, 1H), 7.23 (d, J=2.4 Hz, 1H), 5.91 (s, 1H), 4.35 (s, 2H), 3.62-3.57 (m, 1H), 3.46-3.43 (m, 2H), 3.18-3.15 (m, 1H). MS Calcd: 315, MS Found: 316 ([M+H]⁺).

Example 19: Synthesis of (S)—N-(1-Amino-4-methylpentan-2-yl)-5-chloro-6,7-difluoro-1H-indole-2-carboxamide

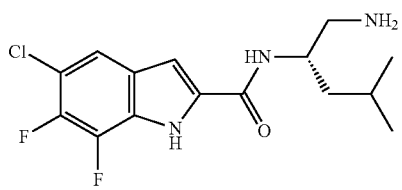 [SMILES: CC(C)C[C@@H](CN)NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.51 (s, 1H), 8.40 (d, J=9.2 Hz, 1H), 7.88-7.84 (m, 2H), 7.78 (d, J=6.0 Hz, 1H), 7.23 (s, 1H), 4.33-4.29 (m, 1H), 3.00-2.98 (m, 1H), 2.86 (s, 1H), 1.66-1.61 (m, 1H), 1.56-1.49 (m, 1H), 1.38-1.31 (m, 1H), 0.92-0.89 (m, 6H). MS Calcd: 329, MS Found: 330 ([M+H]⁺).

Example 20: Synthesis of 5-Chloro-6,7-difluoro-N-((3R,4R)-4-methylpyrrolidin-3-yl)-1H-indole-2-carboxamide

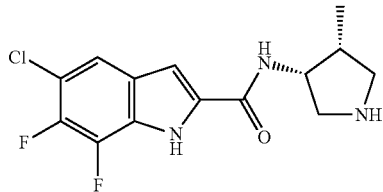 [SMILES: C[C@@H]1CNC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-$d_6$): δ 12.59 (s, 1H), 8.90-8.83 (m, 2H), 8.54 (dd, J=12.4 Hz, 4.4 Hz, 1H), 7.79 (d, J=5.2 Hz, 1H), 7.26 (s, 1H), 4.71-4.66 (m, 1H), 3.57-3.51 (m, 2H), 3.28-3.23 (m, 2H), 3.05-2.96 (m, 1H), 1.00-0.93 (m, 3H). MS Calcd: 313, MS Found: 314 ([M+H]$^+$).

Example 21: Synthesis of (R)—N-(1-Aminopropan-2-yl)-5-chloro-6,7-difluoro-1H-indole-2-carboxamide

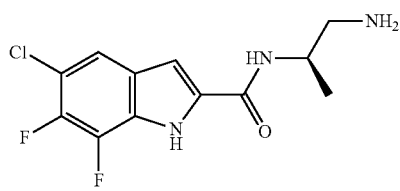 [SMILES: C[C@H](CN)NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). H NMR (400 MHz, DMSO-$d_6$): δ 12.51 (s, 1H), 8.47 (d, J=8.4 Hz, 1H), 7.88 (s, 2H), 7.81 (dd, J=12.8 Hz, 1.2 Hz, 1H), 7.22 (s, 1H), 4.31-4.24 (m, 1H), 2.96-2.91 (m, 2H), 1.22 (d, J=6.8 Hz, 3H). MS Calcd: 287, MS Found: 288 ([M+H]$^+$).

Example 22: Synthesis of ((3S,4S)-3-Amino-4-hydroxypyrrolidin-1-yl)(5-chloro-6,7-difluoro-1H-indol-2-yl)methanone

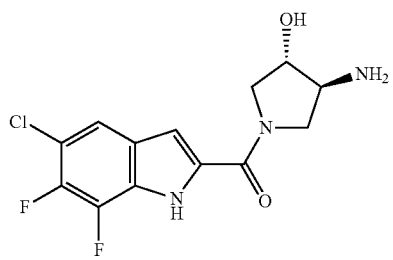 [SMILES: N[C@H]1CN(C(=O)c2cc3cc(Cl)c(F)c(F)c3[nH]2)C[C@@H]1O]

The title compound was prepared using general procedure of ((3S,4R)-3-Amino-4-fluoro-pyrrolidin-1-yl)-(5-chloro-6,7-difluoro-1H-indol-2-yl)-methanone (Example 7). H NMR (400 MHz, DMSO-$d_6$): δ 12.58 (d, J=5.0 Hz, 1H), 8.21 (d, J=15.8 Hz, 3H), 7.75 (s, 1H), 7.05 (s, 1H), 5.88 (t, J=8.8 Hz, 1H), 4.35 (t, J=11.2 Hz, 1H), 4.21 (m, 1H), 3.90 (d, J=6.0 Hz, 1H), 3.73 (d, J=5.6 Hz, 1H), 3.65 (d, J=10.8 Hz, 1H), 3.51 (d, J=6.8 Hz, 1H). MS Calcd: 315, MS Found: 316 ([M+H]$^+$).

Example 23: Synthesis of N-(Azetidin-3-yl)-5-chloro-6,7-difluoro-1H-indole-2-carboxamide

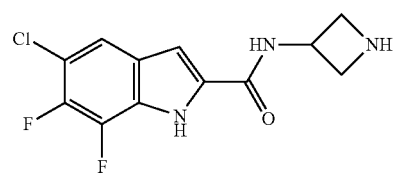 [SMILES: O=C(NC1CNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). H NMR (400 MHz, DMSO-$d_6$): δ 13.00 (s, 1H), 9.23 (d, J=3.6 Hz, 1H), 8.77 (d, J=11.2 Hz, 2H), 7.82 (d, J=3.0 Hz, 1H), 7.23 (s, 1H), 4.85 (d, J=8.0 Hz, 1H), 4.19 (d, J=9.6 Hz, 4H). MS Calcd: 285, MS Found: 286 ([M+H]$^+$).

Example 24: Synthesis of (3-Aminoazetidin-1-yl)(5-chloro-6,7-difluoro-1H-indol-2-yl)methanone

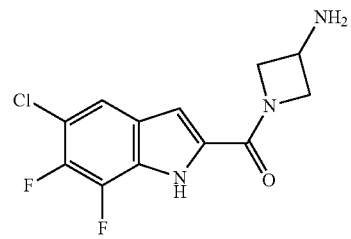 [SMILES: NC1CN(C(=O)c2cc3cc(Cl)c(F)c(F)c3[nH]2)C1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-$d_6$): δ 12.65 (d, J=2.0 Hz, 1H), 8.36 (m, 2H), 7.72 (d, J=4.0 Hz, 1H), 6.95 (d, J=1.2 Hz, 1H), 4.80 (d, J=2.0 Hz, 1H), 4.38 (m, 2H), 4.13 (m, 2H). MS Calcd: 285, MS Found: 286 ([M+H]$^+$).

Example 25: Synthesis of (R)-5-Chloro-6,7-difluoro-N-(pyrrolidin-3-yl)-1H-indole-2-carboxamide

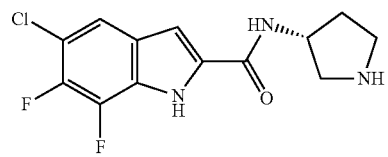 [SMILES: O=C(N[C@@H]1CCNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-$d_6$): δ 12.58 (s, 1H), 8.91-8.83 (m, 1H), 8.73 (d, J=6.4 Hz, 1H), 7.79 (d, J=6.0 Hz, 1H), 7.24 (d, J=2.0 Hz, 1H), 4.56-4.52 (m, 1H), 3.50-3.46 (m, 1H), 3.46-3.40 (m, 2H), 3.20-3.15 (m, 1H), 2.28-2.19 (m, 1H), 2.07-2.00 (m, 1H). MS Calcd: 299, MS Found: 300 ([M+H]+).

Example 26: Synthesis of (S)-5-Chloro-6,7-difluoro-N-(pyrrolidin-3-yl)-1H-indole-2-carboxamide

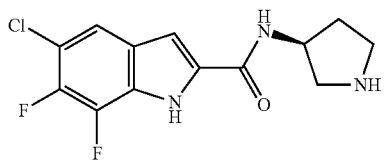 [SMILES: O=C(N[C@H]1CCNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.54 (s, 1H), 8.99 (d, J=1.2 Hz, 2H), 8.74 (d, J=3.0 Hz, 1H), 7.77 (d, J=3.2 Hz, 1H), 7.23 (s, 1H), 4.53 (d, J=6.0 Hz, 1H), 3.47 (m, 1H), 3.29 (m, 2H), 3.27 (m, 1H), 2.21 (m, 1H), 2.02 (m, 1H). MS Calcd: 299, MS Found: 300 ([M+H]+).

Example 27: Synthesis of (S)-(3-Aminopyrrolidin-1-yl)(5-chloro-6,7-difluoro-1H-indol-2-yl)methanone

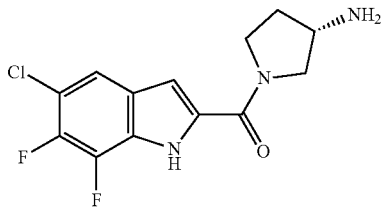 [SMILES: N[C@H]1CCN(C(=O)c2cc3cc(Cl)c(F)c(F)c3[nH]2)C1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.59-12.51 (m, 1H), 8.19-8.01 (m, 3H), 7.75-7.72 (m, 1H), 7.07-6.96 (m, 1H), 4.11-3.73 (m, 5H), 2.41-2.22 (m, 1H), 2.14-1.98 (m, 1H). MS Calcd: 299, MS Found: 300 ([M+H]+).

Example 28: Synthesis of (S)—N-(1-Amino-3,3-dimethylbutan-2-yl)-5-chloro-6,7-difluoro-1H-indole-2-carboxamide

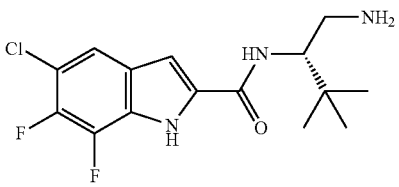 [SMILES: CC(C)(C)[C@@H](CN)NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.53 (s, 1H), 8.26 (d, J=1.2 Hz, 1H), 7.87-7.83 (m, 2H), 7.80 (dd, J=6.4 Hz, 1.2 Hz, 1H), 7.31 (d, J=3.2 Hz, 1H), 4.10 (t, J=9.6 Hz, 1H), 3.15 (d, J=11.2 Hz, 1H), 2.89 (t, J=11.6 Hz, 1H), 0.94 (s, 9H). MS Calcd: 329, MS Found: 330 ([M+H]+).

Example 29: Synthesis of (5-Chloro-6,7-difluoro-1H-indol-2-yl)((3S,4S)-3,4-diaminopyrrolidin-1-yl)methanone

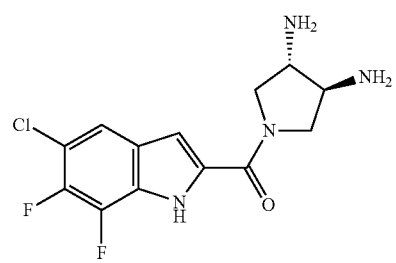 [SMILES: N[C@H]1CN(C(=O)c2cc3cc(Cl)c(F)c(F)c3[nH]2)C[C@@H]1N]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.66 (s, 1H), 8.45 (brs, 5H), 7.78 (d, J=2.8 Hz, 1H), 7.00 (s, 1H), 4.34 (d, J=2.0 Hz, 1H), 4.07-3.96 (m, 4H), 3.78-3.74 (m, 1H). MS Calcd: 314, MS Found: 315 ([M+H]+).

Example 30: Synthesis of N-((3S,4S)-4-Aminopyrrolidin-3-yl)-5-chloro-6,7-difluoro-1H-indole-2-carboxamide

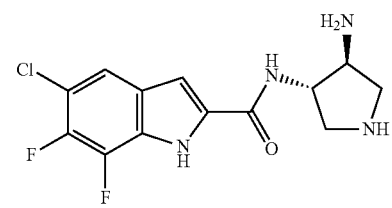 [SMILES: N[C@H]1CNC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.61 (s, 1H), 9.32 (brs, 1H), 8.73 (d, J=7.2 Hz, 1H), 8.38 (brs, 2H), 7.80 (d, J=10.4 Hz, 1H), 7.28 (s, 1H), 4.85-4.82 (m, 1H), 4.05-4.02 (m, 1H), 3.72-3.61 (m, 2H), 3.45-3.31 (m, 2H). MS Calcd: 314, MS Found: 315 ([M+H]+).

Example 31: Synthesis of N-((3R,4S)-4-Aminopyrrolidin-3-yl)-5-chloro-6,7-difluoro-1H-indole-2-carboxamide and N-((3S,4R)-4-Aminopyrrolidin-3-yl)-5-chloro-6,7-difluoro-1H-indole-2-carboxamide

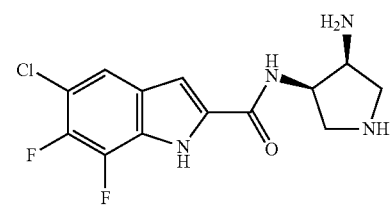

-continued

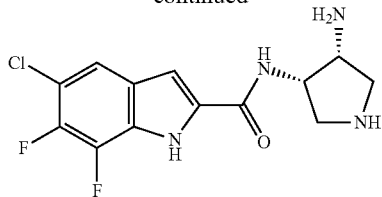

The title compounds were prepared as a mixture using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.64 (s, 1H), 9.47 (brs, 1H), 8.96 (d, J=7.2 Hz, 1H), 8.53 (brs, 2H), 7.83 (d, J=6.4 Hz, 1H), 7.24 (s, 1H), 4.70-4.63 (m, 1H), 3.98-3.91 (m, 1H), 3.76-3.66 (m, 2H), 3.32-3.25 (m, 2H). MS Calcd: 314, MS Found: 315 ([M+H]$^+$).

Example 32: Synthesis of ((3S,4R)-3-Amino-4-hydroxypyrrolidin-1-yl)(5-chloro-6,7-difluoro-1H-indol-2-yl)methanone

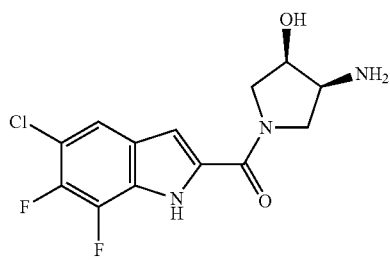 [SMILES: N[C@H]1CN(C(=O)c2cc3cc(Cl)c(F)c(F)c3[nH]2)C[C@H]1O]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.57 (d, J=10.8 Hz, 1H), 8.23 (s, 3H), 7.77-7.73 (m, 1H), 7.01 (d, J=17.6 Hz, 1H), 6.21 (s, 1H), 4.46-4.41 (m, 1H), 4.15-4.05 (m, 1H), 3.85-3.73 (m, 3H), 3.64-3.61 (m, 1H). MS Calcd: 315, MS Found: 316 ([M+H]$^+$).

Example 33: Synthesis of 5-Chloro-6,7-difluoro-N-((3S,4S)-4-methoxypyrrolidin-3-yl)-1H-indole-2-carboxamide

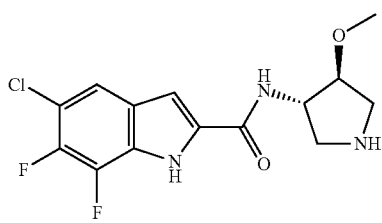 [SMILES: CO[C@H]1CNC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.61 (s, 1H), 9.15 (brs, 2H), 8.72 (d, J=6.8 Hz, 1H), 7.80 (d, J=6.0 Hz, 1H), 7.21 (t, J=2.4 Hz, 1H), 4.53 (t, J=2.0 Hz, 1H), 4.05 (t, J=2.4 Hz, 1H), 3.60-3.56 (m, 1H), 3.48-3.44 (m, 1H), 3.39 (s, 3H), 3.31-3.28 (m, 2H). MS Calcd: 329, MS Found: 330 ([M+H]$^+$).

Example 34: Synthesis of 5-Chloro-6,7-difluoro-N-((3R,4R)-4-methoxypyrrolidin-3-yl)-1H-indole-2-carboxamide

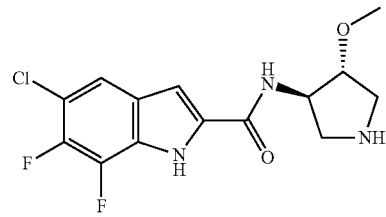 [SMILES: CO[C@@H]1CNC[C@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.61 (d, J=0.8 Hz, 1H), 9.22 (brs, 2H), 8.73 (d, J=6.4 Hz, 1H), 7.80 (d, J=6.4 Hz, 1H), 7.21 (t, J=2.4 Hz, 1H), 4.53 (t, J=3.2 Hz, 1H), 4.05 (t, J=2.4 Hz, 1H), 3.60-3.56 (m, 1H), 3.48-3.45 (m, 1H), 3.38 (m, 3H), 3.31-3.28 (m, 2H). MS Calcd: 329, MS Found: 330 ([M+H]$^+$).

Example 35: Synthesis of ((3S,4S)-3-Amino-4-methoxypyrrolidin-1-yl)(5-chloro-6,7-difluoro-1H-indol-2-yl)methanone

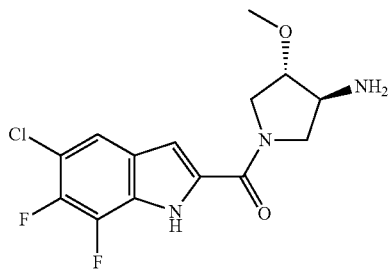 [SMILES: CO[C@H]1CN(C(=O)c2cc3cc(Cl)c(F)c(F)c3[nH]2)C[C@@H]1N]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 7.70 (d, J=5.6 Hz, 1H), 7.05 (d, J=23.2 Hz, 1H), 3.96-3.83 (m, 1H), 3.68-3.60 (m, 2H), 3.59-3.53 (m, 3H), 3.47 (s, 3H), 3.19 (s, 1H). MS Calcd: 329, MS Found: 330 ([M+H]$^+$).

Example 36: Synthesis of 5-Chloro-6,7-difluoro-N-((3R,4S)-4-methylpyrrolidin-3-yl)-1H-indole-2-carboxamide

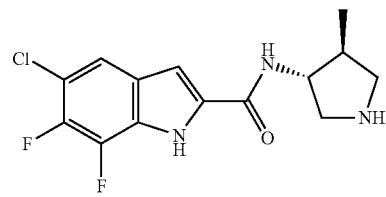 [SMILES: C[C@H]1CNC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.57 (s, 1H), 9.02 (brs, 2H), 8.90 (t, J=7.2 Hz, 1H), 7.79 (d, J=6.0 Hz, 1H), 7.25 (t, J=2.4 Hz, 1H), 4.25-4.16 (m, 1H), 3.58-3.47 (m, 2H), 3.08-3.05 (m, 1H), 2.96-2.87 (m, 1H), 2.45-2.31 (m, 1H), 1.08 (d, J=7.2 Hz, 3H). MS Calcd: 313, MS Found: 314 ([M+H]⁺).

Example 37: Synthesis of ((3S,4S)-3-Amino-4-fluoropyrrolidin-1-yl)(5-chloro-6,7-difluoro-1H-indol-2-yl)methanone

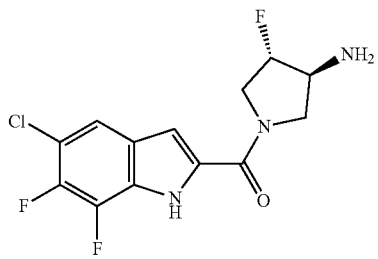 [SMILES: N[C@H]1CN(C(=O)c2cc3cc(Cl)c(F)c(F)c3[nH]2)C[C@@H]1F]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.60 (s, 1H), 8.17 (brs, 2H), 7.75 (d, J=5.6 Hz, 1H), 7.07 (s, 1H), 5.49-5.30 (m, 1H), 4.34-3.81 (m, 5H). MS Calcd: 317, MS Found: 318 ([M+H]⁺).

Example 38: Synthesis of (R)-(3-Aminopiperidin-1-yl)(5-chloro-6,7-difluoro-1H-indol-2-yl)methanone

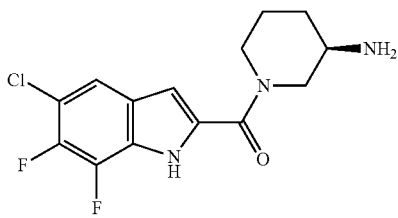 [SMILES: N[C@@H]1CCCN(C(=O)c2cc3cc(Cl)c(F)c(F)c3[nH]2)C1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.51 (s, 1H), 7.96-7.89 (m, 3H), 7.71-7.68 (m, 1H), 6.87 (s, 1H), 4.34-4.30 (m, 1H), 4.06-4.02 (m, 1H), 3.27-3.07 (m, 3H), 2.07-1.99 (m, 1H), 1.84-1.78 (m, 1H), 1.64-1.51 (m, 2H). MS Calcd: 313, MS Found: 314 ([M+H]⁺).

Example 39: Synthesis of (S)-5-Chloro-6,7-difluoro-N-(piperidin-3-yl)-1H-indole-2-carboxamide

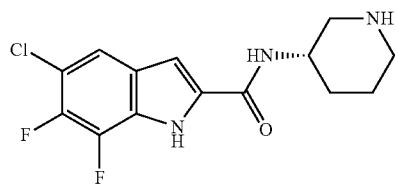 [SMILES: O=C(N[C@H]1CCCNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.56 (s, 1H), 8.77-8.68 (m, 2H), 8.59 (d, J=8.0 Hz, 1H), 7.78 (d, J=5.2 Hz, 1H), 7.25 (s, 1H), 4.20-4.13 (m, 1H), 3.38-3.35 (m, 1H), 3.25-3.21 (m, 1H), 2.90-2.80 (m, 2H), 1.97-1.90 (m, 2H), 1.73-1.57 (m, 2H). MS Calcd: 313, MS Found: 314 ([M+H]⁺).

Example 40: Synthesis of (R)-5-Chloro-6,7-difluoro-N-(piperidin-3-yl)-1H-indole-2-carboxamide

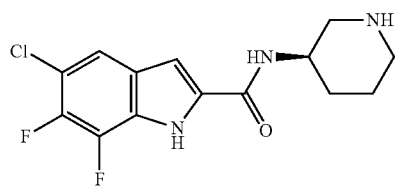 [SMILES: O=C(N[C@@H]1CCCNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.55 (s, 1H), 8.80 (brs, 2H), 8.59 (d, J=7.2 Hz, 1H), 7.78 (d, J=6.0 Hz, 1H), 7.24 (s, 1H), 4.18-4.15 (m, 1H), 3.38-3.32 (m, 1H), 3.24-3.21 (m, 1H), 2.90-2.80 (m, 2H), 1.99-1.89 (m, 2H), 1.73-1.59 (m, 2H). MS Calcd: 313, MS Found: 314 ([M+H]⁺).

Example 41: Synthesis of 5-Chloro-6,7-difluoro-N-((3R,4S)-4-methylpiperidin-3-yl)-1H-indole-2-carboxamide

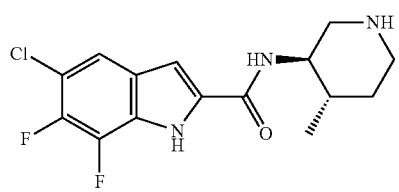 [SMILES: C[C@H]1CCNC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d$_6$): δ 12.31 (s, 1H), 8.71 (brs, 1H), 8.38 (brs, 1H), 8.16 (d, J=8.0 Hz, 1H), 7.64 (d, J=6.4 Hz, 1H), 7.20 (s, 1H), 3.27-3.13 (m, 3H), 2.11-2.07 (m, 1H), 1.76-1.67 (m, 2H), 0.92 (d, J=6.4 Hz, 3H). MS Calcd: 327, MS Found: 328 ([M+H]⁺).

Example 42: Synthesis of ((3S,4S)-3-Amino-4-fluoropiperidin-1-yl)(5-chloro-6,7-difluoro-1H-indol-2-yl)methanone

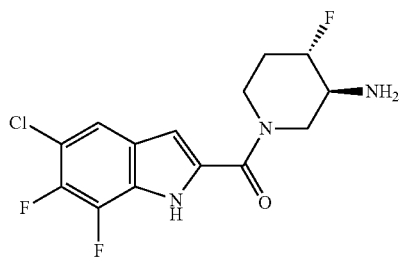 [SMILES: N[C@H]1CN(C(=O)c2cc3cc(Cl)c(F)c(F)c3[nH]2)CC[C@@H]1F]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-$d_6$): δ 12.54 (brs, 1H), 8.47 (s, 3H), 7.70 (d, J=6.0 Hz, 1H), 6.93 (d, J=2.8 Hz, 1H), 4.96-4.77 (m, 1H), 4.55 (brs, 1H), 4.30 (brs, 1H), 3.43 (s, 3H), 2.25 (s, 1H), 1.81 (s, 1H). MS Calcd: 331, MS Found: 332 ([M+H]$^+$).

Example 43: Synthesis of ((3S,4R)-3-Amino-4-fluoropiperidin-1-yl)(5-chloro-6,7-difluoro-1H-indol-2-yl)methanone

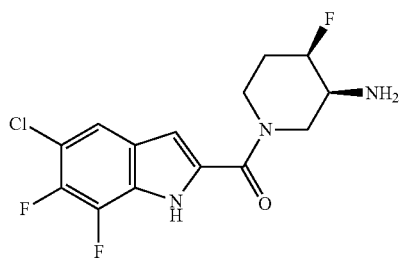 [SMILES: N[C@H]1CN(C(=O)c2cc3cc(Cl)c(F)c(F)c3[nH]2)CC[C@H]1F]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-$d_6$): δ 12.55 (s, 1H), 8.44 (s, 3H), 7.70 (d, J=5.2 Hz, 1H), 6.92 (s, 1H), 5.10 (d, J=49.6 Hz, 1H), 4.36 (brs, 1H), 4.11 (brs, 1H), 3.50-3.36 (s, 2H), 2.16-1.91 (m, 2H). MS Calcd: 331, MS Found: 332 ([M+H]$^+$).

Example 44: Synthesis of (R)-(3-Aminopyrrolidin-1-yl)(5,6-dichloro-1H-indol-2-yl)methanone

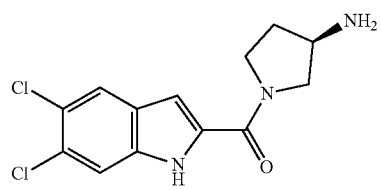 [SMILES: N[C@@H]1CCN(C(=O)c2cc3cc(Cl)c(Cl)cc3[nH]2)C1]

The title compound was prepared using general procedure of (R)-(3-aminopyrrolidin-1-yl)(5-chloro-1H-indol-2-yl)methanone (Example 8). MS Calcd: 297, MS Found: 298 ([M+H]$^+$).

Example 45: Synthesis of (R)-(3-Aminopyrrolidin-1-yl)(5,7-dichloro-1H-indol-2-yl)methanone

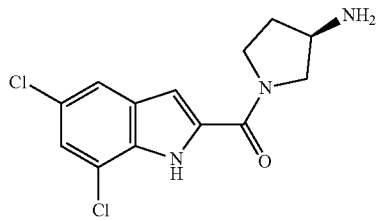

The title compound was prepared using general procedure of (R)-(3-aminopyrrolidin-1-yl)(5-chloro-1H-indol-2-yl)methanone (Example 8). MS Calcd: 297, MS Found: 298 ([M+H]$^+$).

Example 46: Synthesis of (R)-(3-Aminopyrrolidin-1-yl)(6-chloro-1H-indol-2-yl)methanone

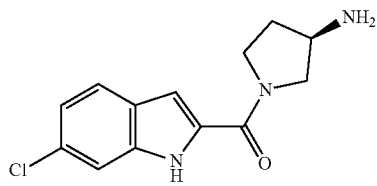 [SMILES: N[C@@H]1CCN(C(=O)c2cc3ccc(Cl)cc3[nH]2)C1]

The title compound was prepared using general procedure of (R)-(3-aminopyrrolidin-1-yl)(5-chloro-1H-indol-2-yl)methanone (Example 8). MS Calcd: 263, MS Found: 264 ([M+H]$^+$).

Example 47: Synthesis of (R)-(3-Aminopyrrolidin-1-yl)(7-bromo-5-chloro-1H-indol-2-yl)methanone

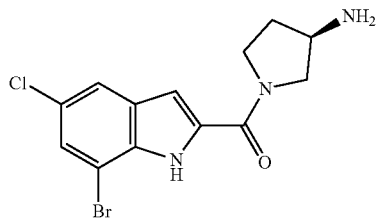 [SMILES: N[C@@H]1CCN(C(=O)c2cc3cc(Cl)cc(Br)c3[nH]2)C1]

The title compound was prepared using general procedure of (R)-(3-aminopyrrolidin-1-yl)(5-chloro-1H-indol-2-yl)methanone (Example 8). MS Calcd: 341, MS Found: 342 ([M+H]$^+$).

Example 48: Synthesis of (R)-(3-Aminopyrrolidin-1-yl)(5-bromo-1H-indol-2-yl)methanone

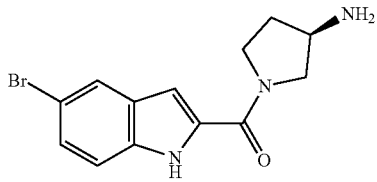 [SMILES: N[C@@H]1CCN(C(=O)c2cc3cc(Br)ccc3[nH]2)C1]

The title compound was prepared using general procedure of (R)-(3-aminopyrrolidin-1-yl)(5-chloro-1H-indol-2-yl)methanone (Example 8). MS Calcd: 307, MS Found: 308 ([M+H]$^+$).

Example 49: Synthesis of (R)-(3-Aminopyrrolidin-1-yl)(5-fluoro-1H-indol-2-yl)methanone

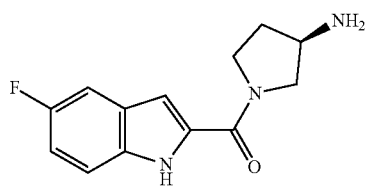 [SMILES: N[C@@H]1CCN(C(=O)c2cc3cc(F)ccc3[nH]2)C1]

The title compound was prepared using general procedure of (R)-(3-aminopyrrolidin-1-yl)(5-chloro-1H-indol-2-yl)methanone (Example 8). MS Calcd: 247, MS Found: 248 ([M+H]$^+$).

Example 50: Synthesis of (R)-(3-Aminopyrrolidin-1-yl)(5,6-difluoro-1H-indol-2-yl)methanone

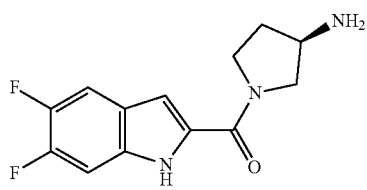 [SMILES: N[C@@H]1CCN(C(=O)c2cc3cc(F)c(F)cc3[nH]2)C1]

The title compound was prepared using general procedure of (R)-(3-aminopyrrolidin-1-yl)(5-chloro-1H-indol-2-yl)methanone (Example 8). MS Calcd: 265, MS Found: 266 ([M+H]$^+$).

Example 51: Synthesis of (S)-5-chloro-6,7-difluoro-N-methyl-N-(pyrrolidin-3-yl)-1H-indole-2-carboxamide

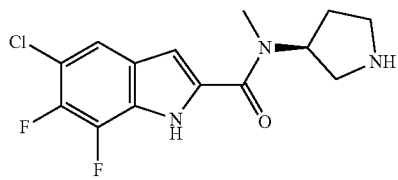 [SMILES: CN(C(=O)c1cc2cc(Cl)c(F)c(F)c2[nH]1)[C@H]1CCNC1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.54 (s, 1H), 9.04 (br s, 2H), 7.69 (d, J=5.6 Hz, 1H), 6.94 (s, 1H), 5.06 (t, J=8.4 Hz, 1H), 3.48-3.43 (m, 2H), 3.38-3.18 (m, 3H), 3.10 (s, 3H), 2.22-2.06 (m, 2H). MS Calcd: 313.8, MS Found: 313.8 ([M+H]$^+$).

Example 52: Synthesis of N-(azetidin-3-yl)-5-chloro-6,7-difluoro-N-methyl-1H-indole-2-carboxamide

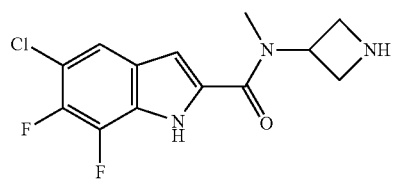 [SMILES: CN(C(=O)c1cc2cc(Cl)c(F)c(F)c2[nH]1)C1CNC1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 7.56 (d, J=6.0 Hz, 1H), 7.08 (d, J=3.2 Hz, 1H), 4.05 (s, 1H), 3.94-3.80 (m, 1H), 3.77 (t, J=4.0 Hz, 1H), 3.66-3.53 (m, 2H), 3.37 (s, 3H). MS Calcd: 299, MS Found: 300 ([M+H]$^+$).

Example 53: Synthesis of 5-chloro-6,7-difluoro-N-(3-methylazetidin-3-yl)-1H-indole-2-carboxamide

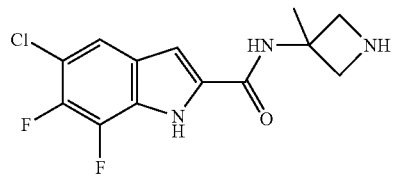 [SMILES: CC1(NC(=O)c2cc3cc(Cl)c(F)c(F)c3[nH]2)CNC1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). $^1$H NMR (400 MHz, DMSO-d$_6$): δ 12.55 (s, 1H), 9.04 (s, 1H), 8.93-8.79 (m, 2H), 7.82 (d, J=6.0 Hz, 1H), 7.24 (t, J=2.4 Hz, 1H), 4.32-4.27 (m, 2H), 3.90 (t, J=7.2 Hz, 2H), 1.62 (s, 3H). MS Calcd: 299, MS Found: 300([M+H]$^+$).

Example 54: Synthesis of 5-chloro-6,7-difluoro-N-((2S,3S)-2-methylazetidin-3-yl)-1H-indole-2-carboxamide

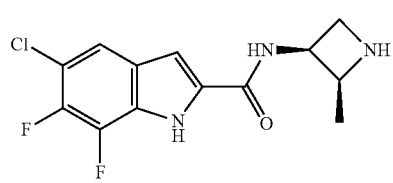 [SMILES: C[C@@H]1NC[C@@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 9.13 (s, 1H), 7.80 (d, J=6.0 Hz, 1H), 7.48-7.32 (m, 5H), 4.96 (s, 1H), 4.58 (s, 1H), 4.17 (d, J=7.6 Hz, 1H), 1.36 (d, J=6.8 Hz, 3H). MS Calcd: 299, MS Found: 300 ([M+H]⁺).

Example 55: Synthesis of 5-chloro-6,7-difluoro-N-((2R,3R)-2-methylazetidin-3-yl)-1H-indole-2-carboxamide

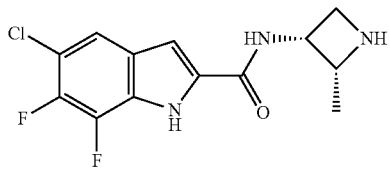 [SMILES: C[C@H]1NC[C@H]1NC(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 9.15-9.10 (m, 1H), 8.70 (brs, 1H), 7.80 (d, J=6.4 Hz, 1H), 7.31 (s, 1H), 4.96 (t, J=8.0 Hz, 1H), 4.59 (t, J=6.8 Hz, 1H), 4.18 (d, J=8.0 Hz, 1H), 1.36 (d, J=6.4 Hz, 3H). MS Calcd: 299, MS Found: 300 ([M+H]⁺).

Example 56: Synthesis of (1R,5S)-3,6-diazabicyclo[3.2.0]heptan-6-yl(5-chloro-6,7-difluoro-1H-indol-2-yl)methanone

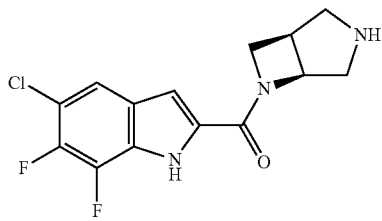 [SMILES: O=C(c1cc2cc(Cl)c(F)c(F)c2[nH]1)N1C[C@H]2CNC[C@H]21]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.64 (s, 1H), 9.51 (d, J=1.6 Hz, 2H), 7.75 (d, J=4.0 Hz, 1H), 6.88 (s, 1H), 5.08 (s, 1H), 4.60 (d, J=8.8 Hz, 1H), 4.20 (d, J=4.8 Hz, 1H), 3.77 (d, J=12.4 Hz, 1H), 3.60 (d, J=12.0 Hz, 1H), 3.44 (s, 1H), 3.19 (d, J=2.4 Hz, 2H). MS Calcd: 311, MS Found: 311.8 ([M+H]⁺).

Example 57: Synthesis of (5-chloro-6,7-difluoro-1H-indol-2-yl)((3aS,6aS)-hexahydropyrrolo[3,4-b]pyrrol-1(2H)-yl)methanone

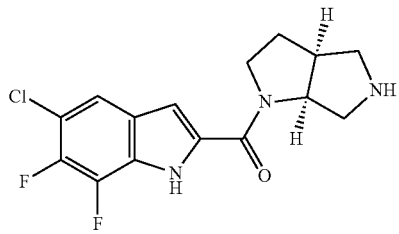 [SMILES: O=C(c1cc2cc(Cl)c(F)c(F)c2[nH]1)N1CC[C@H]2CNC[C@H]21]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.54 (s, 1H), 9.04 (s, 2H), 7.76 (d, J=8.0 Hz, 1H), 7.04 (s, 1H), 4.67 (s, 1H), 3.95-3.94 (m, 2H), 3.49-3.39 (m, 3H), 3.15-3.07 (m, 2H), 2.11-1.97 (m, 2H). MS Calcd.: 325 MS Found: 326 ([M+H]⁺).

Example 58: Synthesis of (5-chloro-6,7-difluoro-1H-indol-2-yl)((3aR,6aR)-hexahydropyrrolo[3,4-b]pyrrol-1(2H)-yl)methanone

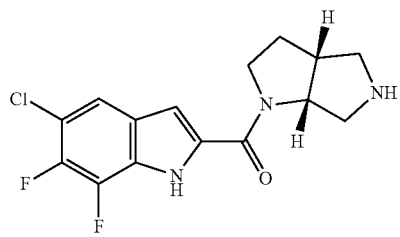 [SMILES: O=C(c1cc2cc(Cl)c(F)c(F)c2[nH]1)N1CC[C@@H]2CNC[C@@H]21]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.54 (s, 1H), 9.04 (s, 2H), 7.76 (d, J=8.0 Hz, 1H), 7.04 (s, 1H), 4.67 (s, 1H), 3.95-3.92 (m, 2H), 3.53-3.38 (m, 3H), 3.15-3.07 (m, 2H), 2.11-1.95 (m, 2H). MS Calcd.: 325 MS Found: 326 ([M+H]⁺).

Example 59: Synthesis of (5-chloro-6,7-difluoro-1H-indol-2-yl)((3aR,6aS)-hexahydropyrrolo[3,4-c]pyrrol-2(1H)-yl)methanone

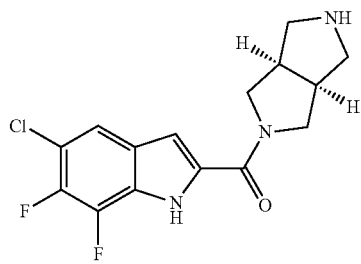 [SMILES: O=C(c1cc2cc(Cl)c(F)c(F)c2[nH]1)N1C[C@H]2CNC[C@H]2C1]

The title compound was prepared using general procedure of ((3S,4R)-3-Amino-4-fluoro-pyrrolidin-1-yl)-(5-chloro-6, 7-difluoro-1H-indol-2-yl)-methanone (Example 7). ¹H NMR (400 MHz, DMSO-d₆): δ 12.51 (s, 1H), 8.88 (s, 1H), 7.72 (d, J=6.4 Hz, 1H), 7.00 (d, J=2.4 Hz, 1H), 4.09-4.01 (m, 2H), 3.87-3.62 (m, 3H), 3.45-3.39 (m, 2H), 3.19-3.04 (m, 4H). MS Calcd.: 325 MS Found: 326 ([M+H]⁺).

Example 60: Synthesis of (5-chloro-6,7-difluoro-1H-indol-2-yl)(2,6-diazaspiro[3.3]heptan-2-yl)methanone

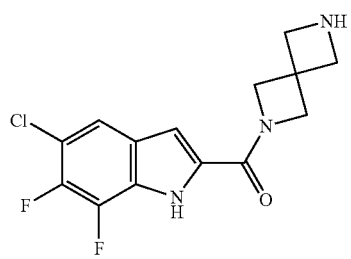

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.60 (s, 1H), 8.57 (d, J=10.8 Hz, 2H), 7.74 (d, J=6.0 Hz, 1H), 6.86 (s, 1H), 4.67 (s, 2H), 4.27 (s, 2H), 4.17 (s, 4H). MS Calcd: 311, MS Found: 312([M+H]⁺).

Example 61: Synthesis of (5-chloro-6,7-difluoro-1H-indol-2-yl)(2,6-diazaspiro[3.4]octan-2-yl)methanone

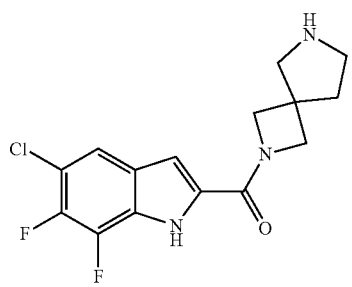 [SMILES: O=C(c1cc2cc(Cl)c(F)c(F)c2[nH]1)N1CC2(CCNC2)C1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.61 (s, 1H), 8.83 (s, 1H), 7.74 (d, J=6.0 Hz, 1H), 6.85 (d, J=2.8 Hz, 1H), 4.54-4.47 (m, 2H), 4.16-4.04 (m, 2H), 3.43 (s, 2H), 3.25-3.21 (m, 2H), 2.25-2.21 (m, 2H). MS Calcd.: 325 MS Found: 326 ([M+H]⁺).

Example 62: Synthesis of (S)-5-chloro-6,7-difluoro-N-(pyrrolidin-3-ylmethyl)-1H-indole-2-carboxamide

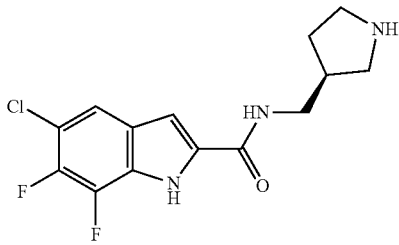 [SMILES: O=C(NC[C@H]1CCNC1)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.53 (s, 1H), 8.77-8.65 (m, 3H), 7.78 (d, J=6.4 Hz, 1H), 7.20 (s, 1H), 3.21-3.38 (m, 4H), 3.15-3.12 (m, 1H), 2.93-2.89 (m, 1H), 2.55-2.51 (m, 1H), 2.05-2.01 (m, 1H), 1.69-1.64 (m, 1H). MS Calcd: 313, MS Found: 314 ([M+H]⁺).

Example 63: Synthesis of (R)-5-chloro-6,7-difluoro-N-(pyrrolidin-3-ylmethyl)-1H-indole-2-carboxamide

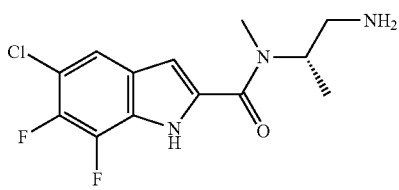 [SMILES: C[C@@H](CN)N(C)C(=O)c1cc2cc(Cl)c(F)c(F)c2[nH]1]

The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, DMSO-d₆): δ 12.53 (s, 1H), 8.87-8.77 (m, 3H), 7.77 (d, J=6.4 Hz, 1H), 7.21 (d, J=2.8 Hz, 1H), 3.43-3.37 (m, 2H), 3.32-3.29 (m, 1H), 3.27-3.22 (m, 1H), 3.18-3.11 (m, 1H), 2.94-2.90 (m, 1H), 2.58-2.52 (m, 1H), 2.08-2.00 (m, 1H), 1.73-1.63 (m, 1H). MS Calcd.: 313 MS Found: 314 ([M+H]⁺).

Example 64: Synthesis of (S)—N-(1-aminopropan-2-yl)-5-chloro-6,7-difluoro-N-methyl-1H-indole-2-carboxamide The title compound was prepared using general procedure of ((3S,4R)-3-Amino-4-fluoro-pyrrolidin-1-yl)-(5-chloro-6,7-difluoro-1H-indol-2-yl)-methanone (Example 7). ¹H NMR (400 MHz, CD₃OD): δ 7.59-7.57 (m, 1H), 7.01 (s, 1H), 4.95-4.92 (m, 1H), 3.31-3.30 (m, 2H), 3.24 (s, 3H), 3.12-3.08 (m, 1H), 1.37 (d, J=6.8 Hz, 3H). MS Calcd.: 301 MS Found: 302 ([M+H]$^+$).

Example 65: Synthesis of ((3S,4S)-3-amino-4-hydroxypyrrolidin-1-yl)(5-bromo-6,7-difluoro-1H-indol-2-yl)methanone

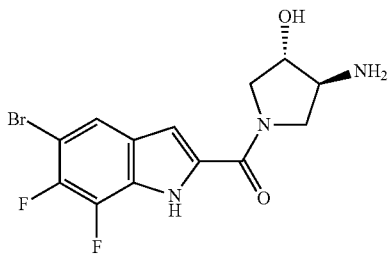

The title compound was prepared using general procedure of (R)-(3-Aminopyrrolidin-1-yl)(5-bromo-6,7-difluoro-1H-indol-2-yl)methanone (Example 5). $^1$H NMR (400 MHz, DMSO-d$_6$): δ 12.56 (s, 1H), 8.17 (s, 2H), 7.85 (d, J=5.6 Hz, 1H), 7.04 (s, 1H), 5.90-5.85 (m, 1H), 4.36-4.13 (m, 2H), 3.91-3.88 (m, 1H), 3.73-3.48 (m, 3H). MS Calcd.: 359 MS Found: 360 ([M+H]$^+$).

Example 66: Synthesis of ((3S,4S)-3-amino-4-hydroxypyrrolidin-1-yl)(6,7-difluoro-5-iodo-1H-indol-2-yl)methanone

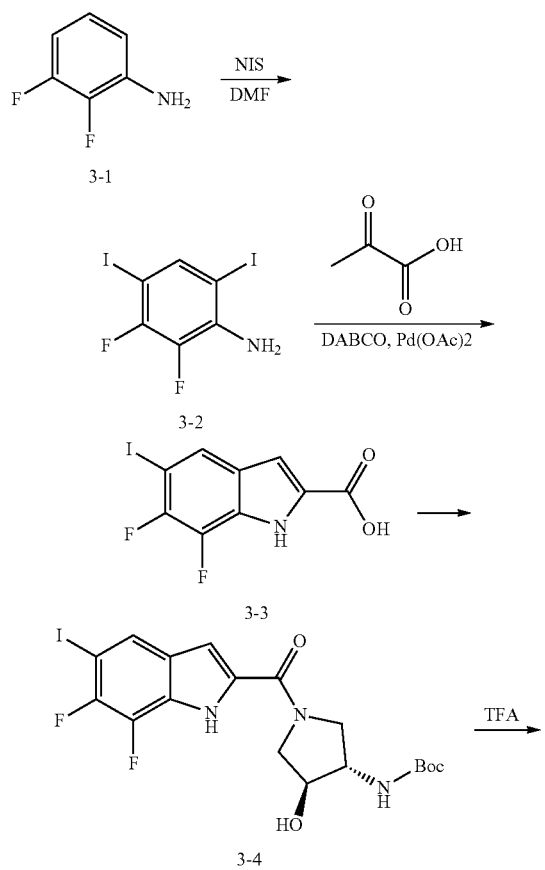

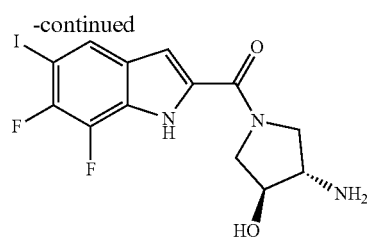

Step 1:

To a solution of 2,4-difluoroaniline (10 g, 77.5 mmol) in DMF (150 mL) was added NIS (34.8 g, 155 mmol) at RT. The mixture was stirred at RT for 3 h. The reaction mixture was diluted with water (2 L) and extracted with EA (500 mL×3). The combined organic phases were dried over Na$_2$SO$_4$, filtered and concentrated. The residue was purified by silica gel chromatography (PE/EA=10:1) to give 2,3-difluoro-4,6-diiodoaniline (17 g, 58% yield) as yellow oil. $^1$H NMR (400 MHz, CDCl$_3$): δ 7.72 (dd, J=6.0 Hz, 2.4 Hz, 1H), 4.30 (br s, 2H).

Step 2:

To a solution of 2,3-difluoro-4,6-diiodoaniline (10 g, 26.3 mmol) in 100 mL of DMF was added 2-oxopropanoic acid (4.6 g, 52.6 mmol), DABCO (5.8 g, 52.6 mmol) and palladium acetate (2.0 g). The solution was degassed and heated at 100° C. for 3 h. The mixture was then cooled to room temperature and filtered. The filtrate was diluted with 300 mL of water and extracted with of EA (600 mL). The organic phase was dried over Na$_2$SO$_4$, filtered and concentrated. The residue was washed with petroleum ether and dried to give (0.50 g, 6% yield) as a brown solid. $^1$H NMR (400 MHz, DMSO-d$_6$): δ 12.18 (br s, 1H), 7.86 (d, J=5.2 Hz, 1H), 6.87 (d, J=10.0 Hz, 1H). 6,7-difluoro-5-iodo-1H-indole-2-carboxylic acid Step 3:

To a solution of 6,7-difluoro-5-iodo-1H-indole-2-carboxylic acid (33 mg, 0.102 mmol) in DMF (1 mL) was added HATU (58 mg, 0.153 mmol) and tert-butyl ((3S,4S)-4-hydroxypyrrolidin-3-yl)carbamate (25 mg, 0.122 mmol). The mixture was stirred at RT for 4 h. The reaction mixture was diluted with water (20 mL) and extracted with EA (20 mL×3). The combined organic phases were dried over Na$_2$SO$_4$, filtered and concentrated. The residue was purified by silica gel chromatography (PE/EA=1:1) to give tert-butyl ((3S,4S)-1-(6,7-difluoro-5-iodo-1H-indole-2-carbonyl)-4-hydroxypyrrolidin-3-yl)carbamate (38 mg, 75% yield) as a white solid. MS Calcd.: 508 MS Found: 508 ([M+H]$^+$).

Step 4:

To a solution of tert-butyl ((3S,4S)-1-(6,7-difluoro-5-iodo-1H-indole-2-carbonyl)-4-hydroxypyrrolidin-3-yl)carbamate (38 mg, 0.076 mmol) in DCM (1 mL) was added trifluoroacetic acid (1 mL). The reaction mixture was stirred at room temperature for 1 h. The reaction mixture was then concentrated to give ((3S,4S)-3-amino-4-hydroxypyrrolidin-1-yl)(6,7-difluoro-5-iodo-1H-indol-2-yl)methanone (35 mg, 94% yield) as a white solid. $^1$H NMR (400 MHz, DMSO-d$_6$): δ 12.45 (br s, 1H), 8.30 (br s, 2H), 7.95 (d, J=4.4 Hz, 1H), 7.00 (s, 1H), 4.36-4.10 (m, 2H), 3.90-3.81 (m, 1H), 3.65-3.51 (m, 3H), 3.51-3.44 (m, 1H). Calcd.: 406.9 MS Found: 408 ([M+H]$^+$).

Example 67: Synthesis of ((3S,4R)-3-amino-4-hydroxypyrrolidin-1-yl)(5-bromo-6,7-difluoro-1H-indol-2-yl)methanone

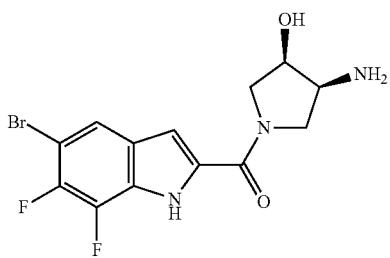

The title compound was prepared using general procedure of (R)-(3-Aminopyrrolidin-1-yl)(5-bromo-6,7-difluoro-1H-indol-2-yl)methanone (Example 5). MS Calcd.: 359 MS Found: 360 ([M+H]$^+$).

I. Biological Evaluation

Example 1: PAD4 Protein for Assay

Protein: Recombinant human PAD4 (2-663) was expressed in E. coli as an N-terminal Strep-tag and C-terminal 6-his tag fusion protein. Protein was purified using Strep-tactin resin followed by size exclusion chromatography. Tags were not removed during purification. Activity of the protein was determined using ammonia quantification assay.

Example 2: PAD4 Inhibition Assay

PAD4 enzyme (10 μL) was diluted to concentration of 75 nM in assay buffer A (100 mM HEPES, pH 8, 50 mM NaCl, 2 mM DTT, 0.6 mg/mL BSA and 0.5% DMSO) and added to wells containing 10 μL of various concentrations of test compound, or DMSO vehicle in buffer A with 1.5% final DMSO concentration in a Corning high volume 384 well black plate. Following 60 mins pre-incubation at RT with gentle shaking, the reaction was initiated by the addition of 10 μL of substrate buffer containing 3 mM N-a-benzoyl-L-arginine ethyl ester (BAEE) and 600 μM CaCl$_2$ in assay buffer A. The reaction was stopped after 60 mins with the addition of 15 μL stop/detection buffer containing 7.5 mM phthalaldehyde, 50 mM EDTA and 7.5 mM DTT in assay buffer A. Quenched reactions were incubated at RT for 45 mins before measuring fluorescent signal ($\lambda_{ex}$ 405/$\lambda_{em}$ 460) on an Envision plate reader (Perkin Elmer Life Sciences, Waltham, Mass., USA).

Representative data for exemplary compounds disclosed in Table 1 are presented in the following Table 2.

TABLE 2

| Compound Name | PAD4 IC$_{50}$ |
| --- | --- |
| (R)-(3-Aminopyrrolidin-1-yl)(5-chloro-6,7-difluoro-1H-indol-2-yl)methanone | A |
| (R)-(3-Aminopyrrolidin-1-yl)(5-chloro-7-fluoro-1H-indol-2-yl)methanone | A |
| (R)-(3-Aminopyrrolidin-1-yl)(5,6,7-trifluoro-1H-indol-2-yl)methanone | B |
| (R)-(3-Aminopyrrolidin-1-yl)(6-chloro-5,7-difluoro-1H-indol-2-yl)methanone | B |
| (R)-(3-Aminopyrrolidin-1-yl)(5-bromo-6,7-difluoro-1H-indol-2-yl)methanone | A |
| (R)-(3-Aminopyrrolidin-1-yl)(6-bromo-5,7-difluoro-1H-indol-2-yl)methanone | C |
| ((3S,4R)-3-Amino-4-fluoro-pyrrolidin-1-yl)-(5-chloro-6,7-difluoro-1H-indol-2-yl)-methanone | C |
| (R)-(3-Aminopyrrolidin-1-yl)(5-chloro-1H-indol-2-yl)methanone | B |
| (S)-N-(1-Aminopropan-2-yl)-5-chloro-6,7-difluoro-1H-indole-2-carboxamide | A |
| (S)-N-(1-Aminobutan-2-yl)-5-chloro-6,7-difluoro-1H-indole-2-carboxamide | B |
| Synthesis of N-(2-Amino-1-cyclopropylethyl)-5-chloro-6,7-difluoro-1H-indole-2-carboxamide | C |
| N-(3-(Aminomethyl)oxetan-3-yl)-5-chloro-6,7-difluoro-1H-indole-2-carboxamide | C |
| 5-Chloro-6,7-difluoro-N-((3S,4R)-4-methylpyrrolidin-3-yl)-1H-indole-2-carboxamide | B |
| 5-Chloro-6,7-difluoro-N-((3S,4S)-4-methylpyrrolidin-3-yl)-1H-indole-2-carboxamide | A |
| 5-Chloro-6,7-difluoro-N-((3R,4R)-4-hydroxypyrrolidin-3-yl)-1H-indole-2-carboxamide | B |
| 5-Chloro-6,7-difluoro-N-((3R,4S)-4-hydroxypyrrolidin-3-yl)-1H-indole-2-carboxamide | B |
| 5-Chloro-6,7-difluoro-N-((3S,4R)-4-hydroxypyrrolidin-3-yl)-1H-indole-2-carboxamide | C |
| 5-Chloro-6,7-difluoro-N-((3S,4S)-4-hydroxypyrrolidin-3-yl)-1H-indole-2-carboxamide | C |
| (S)-N-(1-Amino-4-methylpentan-2-yl)-5-chloro-6,7-difluoro-1H-indole-2-carboxamide | C |
| 5-Chloro-6,7-difluoro-N-((3R,4R)-4-methylpyrrolidin-3-yl)-1H-indole-2-carboxamide | A |
| (R)-N-(1-Aminopropan-2-yl)-5-chloro-6,7-difluoro-1H-indole-2-carboxamide | C |
| ((3S,4S)-3-Amino-4-hydroxypyrrolidin-1-yl)(5-chloro-6,7-difluoro-1H-indol-2-yl)methanone | A |
| N-(Azetidin-3-yl)-5-chloro-6,7-difluoro-1H-indole-2-carboxamide | A |
| (3-Aminoazetidin-1-yl)(5-chloro-6,7-difluoro-1H-indol-2-yl)methanone | B |
| (R)-5-Chloro-6,7-difluoro-N-(pyrrolidin-3-yl)-1H-indole-2-carboxamide | C |
| (S)-5-Chloro-6,7-difluoro-N-(pyrrolidin-3-yl)-1H-indole-2-carboxamide | B |
| (S)-(3-Aminopyrrolidin-1-yl)(5-chloro-6,7-difluoro-1H-indol-2-yl)methanone | A |
| (S)-N-(1-Amino-3,3-dimethylbutan-2-yl)-5-chloro-6,7-difluoro-1H-indole-2-carboxamide | C |
| (5-Chloro-6,7-difluoro-1H-indol-2-yl)((3S,4S)-3,4-diaminopyrrolidin-1-yl)methanone | B |
| N-((3S,4S)-4-Aminopyrrolidin-3-yl)-5-chloro-6,7-difluoro-1H-indole-2-carboxamide | C |
| N-((3R,4S)-4-Aminopyrrolidin-3-yl)-5-chloro-6,7-difluoro-1H-indole-2-carboxamide; N-((3S,4R)-4-Aminopyrrolidin-3-yl)-5-chloro-6,7-difluoro-1H-indole-2-carboxamide | |
| ((3S,4R)-3-Amino-4-hydroxypyrrolidin-1-yl)(5-chloro-6,7-difluoro-1H-indol-2-yl)methanone | B |
| 5-Chloro-6,7-difluoro-N-((3S,4S)-4-methoxypyrrolidin-3-yl)-1H-indole-2-carboxamide | C |
| 5-Chloro-6,7-difluoro-N-((3R,4R)-4-methoxypyrrolidin-3-yl)-1H-indole-2-carboxamide | C |
| ((3S,4S)-3-Amino-4-methoxypyrrolidin-1-yl)(5-chloro-6,7-difluoro-1H-indol-2-yl)methanone | D |
| 5-Chloro-6,7-difluoro-N-((3R,4S)-4-methylpyrrolidin-3-yl)-1H-indole-2-carboxamide | C |
| ((3S,4S)-3-Amino-4-fluoropyrrolidin-1-yl)(5-chloro-6,7-difluoro-1H-indol-2-yl)methanone | B |
| (R)-(3-Aminopiperidin-1-yl)(5-chloro-6,7-difluoro-1H-indol-2-yl)methanone | C |
| (S)-5-Chloro-6,7-difluoro-N-(piperidin-3-yl)-1H-indole-2-carboxamide | C |
| (R)-5-Chloro-6,7-difluoro-N-(piperidin-3-yl)-1H-indole-2-carboxamide | C |
| 5-Chloro-6,7-difluoro-N-((3R,4S)-4-methylpiperidin-3-yl)-1H-indole-2-carboxamide | C |
| ((3S,4S)-3-Amino-4-fluoropiperidin-1-yl)(5-chloro-6,7-difluoro-1H-indol-2-yl)methanone | C |

TABLE 2-continued

| Compound Name | PAD4 IC$_{50}$ |
|---|---|
| ((3S,4R)-3-Amino-4-fluoropiperidin-1-yl)(5-chloro-6,7-difluoro-1H-indol-2-yl)methanone | D |
| (R)-(3-Aminopyrrolidin-1-yl)(5,6-dichloro-1H-indol-2-yl)methanone | B |
| (R)-(3-Aminopyrrolidin-1-yl)(5,7-dichloro-1H-indol-2-yl)methanone | C |
| (R)-(3-Aminopyrrolidin-1-yl)(6-chloro-1H-indol-2-yl)methanone | B |
| (R)-(3-Aminopyrrolidin-1-yl)(7-bromo-5-chloro-1H-indol-2-yl)methanone | C |
| (R)-(3-Aminopyrrolidin-1-yl)(5-bromo-1H-indol-2-yl)methanone | B |
| (R)-(3-Aminopyrrolidin-1-yl)(5-fluoro-1H-indol-2-yl)methanone | C |
| (R)-(3-Aminopyrrolidin-1-yl)(5,6-difluoro-1H-indol-2-yl)methanone | C |
| (S)-5-chloro-6,7-difluoro-N-methyl-N-(pyrrolidin-3-yl)-1H-indole-2-carboxamide | C |
| N-(azetidin-3-yl)-5-chloro-6,7-difluoro-N-methyl-1H-indole-2-carboxamide | C |
| 5-chloro-6,7-difluoro-N-(3-methylazetidin-3-yl)-1H-indole-2-carboxamide | C |
| 5-chloro-6,7-difluoro-N-((2S,3S)-2-methylazetidin-3-yl)-1H-indole-2-carboxamide | B |
| 5-chloro-6,7-difluoro-N-((2R,3R)-2-methylazetidin-3-yl)-1H-indole-2-carboxamide | B |
| (1R,5S)-3,6-diazabicyclo[3.2.0]heptan-6-yl(5-chloro-6,7-difluoro-1H-indol-2-yl)methanone | B |
| (5-chloro-6,7-difluoro-1H-indol-2-yl)((3aS,6aS)-hexahydropyrrolo[3,4-b]pyrrol-1(2H)-yl)methanone | B |
| (5-chloro-6,7-difluoro-1H-indol-2-yl)((3aR,6aR)-hexahydropyrrolo[3,4-b]pyrrol-1(2H)-yl)methanone | C |
| (5-chloro-6,7-difluoro-1H-indol-2-yl)((3aR,6aS)-hexahydropyrrolo[3,4-c]pyrrol-2(1H)-yl)methanone | C |
| (5-chloro-6,7-difluoro-1H-indol-2-yl)(2,6-diazaspiro[3.3]heptan-2-yl)methanone | C |
| (5-chloro-6,7-difluoro-1H-indol-2-yl)(2,6-diazaspiro[3.4]octan-2-yl)methanone | C |
| (S)-5-chloro-6,7-difluoro-N-(pyrrolidin-3-ylmethyl)-1H-indole-2-carboxamide | C |
| (R)-5-chloro-6,7-difluoro-N-(pyrrolidin-3-ylmethyl)-1H-indole-2-carboxamide | C |
| (S)-N-(1-aminopropan-2-yl)-5-chloro-6,7-difluoro-N-methyl-1H-indole-2-carboxamide | B |
| ((3S,4S)-3-amino-4-hydroxypyrrolidin-1-yl)(5-bromo-6,7-difluoro-1H-indol-2-yl)methanone | B |
| ((3S,4S)-3-amino-4-hydroxypyrrolidin-1-yl)(6,7-difluoro-5-iodo-1H-indol-2-yl)methanone | B |
| ((3S,4R)-3-amino-4-hydroxypyrrolidin-1-yl)(5-bromo-6,7-difluoro-1H-indol-2-yl)methanone | B |

Where A = ≤1 μM; B = >1 μM-≤10 μM; C = >10 μM-≤100 μM; D = >100 μM.

III. Preparation of Pharmaceutical Dosage Forms

Example 1: Oral Capsule

The active ingredient is a compound of Table 1, or a pharmaceutically acceptable salt thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

I claim:

1. A compound, or pharmaceutically acceptable salt or solvate thereof, having the structure of Formula (I):

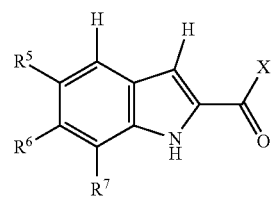

wherein,
$R^5$ is selected from halogen;
$R^6$ is selected from fluoro;
$R^7$ is selected from fluoro;
X is selected from:

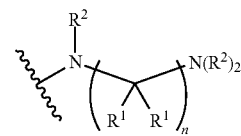

wherein n is 2, 3, or 4; each $R^1$ is independently selected from hydrogen, optionally substituted alkyl, optionally substituted cycloalkyl, or optionally substituted cycloalkylalkyl; and each $R^2$ is independently hydrogen or optionally substituted alkyl;

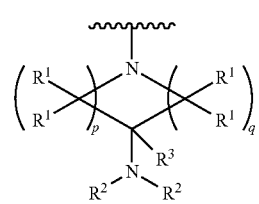

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl;

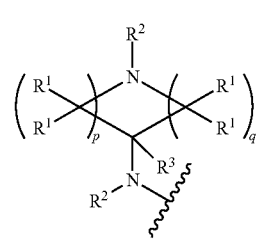

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl.

2. The compound of claim 1, or pharmaceutically acceptable salt or solvate thereof, wherein X is:

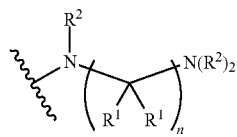

wherein n is 2, 3, or 4; each $R^1$ is independently selected from hydrogen, optionally substituted alkyl, optionally substituted cycloalkyl, or optionally substituted cycloalkylalkyl; and each $R^2$ is independently hydrogen or optionally substituted alkyl.

3. The compound of claim 2, or pharmaceutically acceptable salt or solvate thereof, wherein each $R^1$ is independently selected from hydrogen, optionally substituted alkyl; each $R^2$ is hydrogen; and n is 2 or 3.

4. The compound of claim 1, or pharmaceutically acceptable salt or solvate thereof, wherein X is:

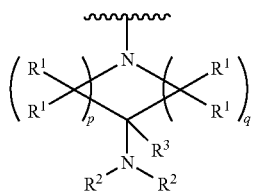

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl.

5. The compound of claim 4, or pharmaceutically acceptable salt or solvate thereof, wherein $R^2$ is hydrogen, and $R^3$ is hydrogen.

6. The compound of claim 4, or pharmaceutically acceptable salt or solvate thereof, wherein each $R^1$ is independently selected from hydrogen or optionally substituted alkyl.

7. The compound of claim 4, or pharmaceutically acceptable salt or solvate thereof, wherein p is 2, and q is 1.

8. The compound of claim 4, or pharmaceutically acceptable salt or solvate thereof, wherein X is 3-amino-4-hydroxypyrrolidin-1-yl.

9. The compound of claim 1, or pharmaceutically acceptable salt or solvate thereof, wherein X is:

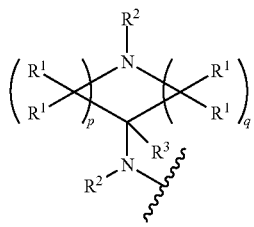

wherein p is 1, 2, 3, or 4; q is 1, 2, 3, or 4; each $R^1$ is independently selected from hydrogen, halogen, —OH, —NH$_2$, optionally substituted alkyl, or optionally substituted alkoxy; each $R^2$ is hydrogen or optionally substituted alkyl; and $R^3$ is hydrogen or optionally substituted alkyl.

10. The compound of claim 9, or pharmaceutically acceptable salt or solvate thereof, wherein $R^2$ is hydrogen, $R^3$ is hydrogen, p is 2, q is 1, and each $R^1$ is independently selected from hydrogen or optionally substituted alkyl.

11. The compound of claim 1, or pharmaceutically acceptable salt or solvate thereof, wherein $R^5$ is chloro, $R^6$ is fluoro, and $R^7$ is fluoro.

12. A compound, or pharmaceutically acceptable salt or solvate thereof, selected from:
(R)-(3-Aminopyrrolidin-1-yl)(5-chloro-6,7-difluoro-1H-indol-2-yl)methanone,
(R)-(3-Aminopyrrolidin-1-yl)(5,6,7-trifluoro-1H-indol-2-yl)methanone,
(R)-(3-Aminopyrrolidin-1-yl)(5-bromo-6,7-difluoro-1H-indol-2-yl)methanone,
((3 S,4R)-3-Amino-4-fluoro-pyrrolidin-1-yl)-(5-chloro-6,7-difluoro-1H-indol-2-yl)-methanone,
(S)-N-(1-Aminopropan-2-yl)-5-chloro-6,7-difluoro-1H-indole-2-carboxamide,
(S)-N-(1-Aminobutan-2-yl)-5-chloro-6,7-difluoro-1H-indole-2-carboxamide,
N-(2-Amino-1-cyclopropylethyl)-5-chloro-6,7-difluoro-1H-indole-2-carboxamide,
N-(3-(Aminomethyl)oxetan-3-yl)-5-chloro-6,7-difluoro-1H-indole-2-carboxamide,
5-Chloro-6,7-difluoro-N-((3 S,4R)-4-methylpyrrolidin-3-yl)-1H-indole-2-carboxamide,
5-Chloro-6,7-difluoro-N-((3 S,4S)-4-methylpyrrolidin-3-yl)-1H-indole-2-carboxamide,
5-Chloro-6,7-difluoro-N-((3R,4R)-4-hydroxypyrrolidin-3-yl)-1H-indole-2-carboxamide,
5-Chloro-6,7-difluoro-N-((3R,4S)-4-hydroxypyrrolidin-3-yl)-1H-indole-2-carboxamide,
5-Chloro-6,7-difluoro-N-((3 S,4R)-4-hydroxypyrrolidin-3-yl)-1H-indole-2-carboxamide,
5-Chloro-6,7-difluoro-N-((3 S,4S)-4-hydroxypyrrolidin-3-yl)-1H-indole-2-carboxamide,
(S)-N-(1-Amino-4-methylpentan-2-yl)-5-chloro-6,7-difluoro-1H-indole-2-carboxamide,
5-Chloro-6,7-difluoro-N-((3R,4R)-4-methylpyrrolidin-3-yl)-1H-indole-2-carboxamide,
(R)-N-(1-Aminopropan-2-yl)-5-chloro-6,7-difluoro-1H-indole-2-carboxamide, ((3 S,4S)-3-Amino-4-hydroxypyrrolidin-1-yl)(5-chloro-6,7-difluoro-1H-indol-2-yl)methanone,
N-(Azetidin-3-yl)-5-chloro-6,7-difluoro-1H-indole-2-carboxamide,
(3-Aminoazetidin-1-yl)(5-chloro-6,7-difluoro-1H-indol-2-yl)methanone,
(R)-5-Chloro-6,7-difluoro-N-(pyrrolidin-3-yl)-1H-indole-2-carboxamide,
(S)-5-Chloro-6,7-difluoro-N-(pyrrolidin-3-yl)-1H-indole-2-carboxamide,
(S)-(3-Aminopyrrolidin-1-yl)(5-chloro-6,7-difluoro-1H-indol-2-yl)methanone,
(S)-N-(1-Amino-3,3-dimethylbutan-2-yl)-5-chloro-6,7-difluoro-1H-indole-2-carboxamide,
(5-Chloro-6,7-difluoro-1H-indol-2-yl)((3 S,4S)-3,4-diaminopyrrolidin-1-yl)methanone,
N-((3 S,4S)-4-Aminopyrrolidin-3-yl)-5-chloro-6,7-difluoro-1H-indole-2-carboxamide, N-((3R,4S)-4-Aminopyrrolidin-3-yl)-5-chloro-6,7-difluoro-1H-indole-2-carboxamide,
((3 S,4R)-3-Amino-4-hydroxypyrrolidin-1-yl)(5-chloro-6,7-difluoro-1H-indol-2-yl)methanone,
5-Chloro-6,7-difluoro-N-((3 S,4S)-4-methoxypyrrolidin-3-yl)-1H-indole-2-carboxamide,
5-Chloro-6,7-difluoro-N-((3R,4R)-4-methoxypyrrolidin-3-yl)-1H-indole-2-carboxamide,
((3 S,4S)-3-Amino-4-methoxypyrrolidin-1-yl)(5-chloro-6,7-difluoro-1H-indol-2-yl)methanone,
5-Chloro-6,7-difluoro-N-((3R,4 S)-4-methylpyrrolidin-3-yl)-1H-indole-2-carboxamide,
((3 S,4S)-3-Amino-4-fluoropyrrolidin-1-yl)(5-chloro-6,7-difluoro-1H-indol-2-yl)methanone,
(R)-(3-Aminopiperidin-1-yl)(5-chloro-6,7-difluoro-1H-indol-2-yl)methanone,
(S)-5-Chloro-6,7-difluoro-N-(piperidin-3-yl)-1H-indole-2-carboxamide,
(R)-5-Chloro-6,7-difluoro-N-(piperidin-3-yl)-1H-indole-2-carboxamide,
5-Chloro-6,7-difluoro-N-((3R,4 S)-4-methylpiperidin-3-yl)-1H-indole-2-carboxamide,
((3 S,4S)-3-Amino-4-fluoropiperidin-1-yl)(5-chloro-6,7-difluoro-1H-indol-2-yl)methanone, and
((3 S,4R)-3-Amino-4-fluoropiperidin-1-yl)(5-chloro-6,7-difluoro-1H-indol-2-yl)methanone.

13. A compound, or pharmaceutically acceptable salt or solvate thereof, selected from:
(S)-5-chloro-6,7-difluoro-N-methyl-N-(pyrrolidin-3-yl)-1H-indole-2-carboxamide,
N-(azetidin-3-yl)-5-chloro-6,7-difluoro-N-methyl-1H-indole-2-carboxamide,
5-chloro-6,7-difluoro-N-(3-methylazetidin-3-yl)-1H-indole-2-carboxamide,
5-chloro-6,7-difluoro-N-((2 S, 3 S)-2-methylazetidin-3-yl)-1H-indole-2-carboxamide,
5-chloro-6,7-difluoro-N-((2R,3R)-2-methylazetidin-3-yl)-1H-indole-2-carboxamide,
(1R,5S)-3,6-diazabicyclo[3.2.0]heptan-6-yl(5-chloro-6,7-difluoro-1H-indol-2-yl)methanone,
(5-chloro-6,7-difluoro-1H-indol-2-yl)((3aS,6aS)-hexahydropyrrolo[3,4-b]pyrrol-1(2H)-yl)methanone,
(5-chloro-6,7-difluoro-1H-indol-2-yl)((3aR,6aR)-hexahydropyrrolo[3,4-b]pyrrol-1(2H)-yl)methanone,
(5-chloro-6,7-difluoro-1H-indol-2-yl)((3aR,6aS)-hexahydropyrrolo[3,4-c]pyrrol-2(1H)-yl)methanone,
(5-chloro-6,7-difluoro-1H-indol-2-yl)(2,6-diazaspiro[3.3]heptan-2-yl)methanone,
(5-chloro-6,7-difluoro-1H-indol-2-yl)(2,6-diazaspiro[3.4]octan-2-yl)methanone,
(S)-5-chloro-6,7-difluoro-N-(pyrrolidin-3-ylmethyl)-1H-indole-2-carboxamide,
(R)-5-chloro-6,7-difluoro-N-(pyrrolidin-3-ylmethyl)-1H-indole-2-carboxamide,
(S)-N-(1-aminopropan-2-yl)-5-chloro-6,7-difluoro-N-methyl-1H-indole-2-carboxamide,
((3 S,4S)-3-amino-4-hydroxypyrrolidin-1-yl)(5-bromo-6,7-difluoro-1H-indol-2-yl)methanone,
((3 S,4S)-3-amino-4-hydroxypyrrolidin-1-yl)(6,7-difluoro-5-iodo-1H-indol-2-yl)methanone, and
((3 S,4R)-3-amino-4-hydroxypyrrolidin-1-yl)(5-bromo-6,7-difluoro-1H-indol-2-yl)methanone.

14. The compound of claim 12, or pharmaceutically acceptable salt or solvate thereof, wherein the compound is selected from:
(S)-N-(1-Aminopropan-2-yl)-5-chloro-6,7-difluoro-1H-indole-2-carboxamide; or
5-Chloro-6,7-difluoro-N-((3 S,4S)-4-methylpyrrolidin-3-yl)-1H-indole-2-carboxamide.

15. The compound of claim 12, or pharmaceutically acceptable salt or solvate thereof, wherein the compound is selected from:
((3 S,4S)-3-Amino-4-hydroxypyrrolidin-1-yl)(5-chloro-6,7-difluoro-1H-indol-2-yl)methanone; or
((3 S,4R)-3-Amino-4-hydroxypyrrolidin-1-yl)(5-chloro-6,7-difluoro-1H-indol-2-yl)methanone.

16. The compound of claim 13, or pharmaceutically acceptable salt or solvate thereof, wherein the compound is selected from:
((3 S,4S)-3-amino-4-hydroxypyrrolidin-1-yl)(5-bromo-6,7-difluoro-1H-indol-2-yl)methanone; or
((3 S,4R)-3-amino-4-hydroxypyrrolidin-1-yl)(5-bromo-6,7-difluoro-1H-indol-2-yl)methanone.

17. A pharmaceutical composition comprising a compound of Formula (I), or pharmaceutically acceptable salt or solvate thereof, as described in claim 1, and at least one pharmaceutically acceptable excipient.

* * * * *